(12) United States Patent
Tanabe et al.

(10) Patent No.: US 9,040,722 B2
(45) Date of Patent: May 26, 2015

(54) PHOTOELECTRIC CONVERSION DEVICE AND PHOTOELECTRIC CONVERSION DEVICE DYE, AND COMPOUND

(75) Inventors: Junji Tanabe, Tokyo (JP); Atsushi Monden, Tokyo (JP); Masahiro Shinkai, Tokyo (JP); Yohei Aoyama, Tokyo (JP); Kensaku Akimoto, Tokyo (JP); Tatsuya Ishida, Tokyo (JP); Toru Yano, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 34 days.

(21) Appl. No.: 13/876,618

(22) PCT Filed: Sep. 27, 2011

(86) PCT No.: PCT/JP2011/072053
§ 371 (c)(1),
(2), (4) Date: Mar. 28, 2013

(87) PCT Pub. No.: WO2012/046592
PCT Pub. Date: Apr. 12, 2012

(65) Prior Publication Data
US 2013/0186468 A1 Jul. 25, 2013

(30) Foreign Application Priority Data
Oct. 6, 2010 (JP) ................. 2010-226588

(51) Int. Cl.
| | | |
|---|---|---|
| C07D 405/12 | (2006.01) | |
| C07D 209/08 | (2006.01) | |
| C07D 417/14 | (2006.01) | |
| C07D 409/14 | (2006.01) | |
| C07D 403/06 | (2006.01) | |
| C07D 413/14 | (2006.01) | |
| H01L 51/00 | (2006.01) | |
| C09B 23/12 | (2006.01) | |
| C09B 23/01 | (2006.01) | |
| C07D 209/60 | (2006.01) | |
| C07D 405/14 | (2006.01) | |
| C09B 23/04 | (2006.01) | |
| C09B 23/06 | (2006.01) | |
| C09B 23/08 | (2006.01) | |
| C09B 23/10 | (2006.01) | |

(Continued)

(52) U.S. Cl.
CPC .......... *H01L 51/0032* (2013.01); *C07D 403/06* (2013.01); *C07D 409/14* (2013.01); *C09B 23/12* (2013.01); *C09B 23/0016* (2013.01); *C09B 23/0066* (2013.01); *C07D 209/60* (2013.01); *C07D 405/14* (2013.01); *C07D 413/14* (2013.01); *C07D 417/14* (2013.01); *C09B 23/0058* (2013.01); *C09B 23/04* (2013.01); *C09B 23/06* (2013.01); *C09B 23/083* (2013.01); *C09B 23/105* (2013.01); *C09B 23/107* (2013.01); *C09B 23/164* (2013.01); *H01G 9/2031* (2013.01); *H01G 9/204* (2013.01); *H01G 9/2059* (2013.01); *H01L 51/0064* (2013.01); *Y02E 10/542* (2013.01); *C07D 405/12* (2013.01); *C07D 209/08* (2013.01); *H01G 9/2063* (2013.01); *C09B 23/0075* (2013.01); *C09B 23/0083* (2013.01)

(58) Field of Classification Search
USPC ......................................... 548/490, 491, 455
See application file for complete search history.

(56) References Cited

U.S. PATENT DOCUMENTS 3,989,522 A * 11/1976 Poot et al. ..................... 430/264
2006/0237059 A1 10/2006 Kurihara et al.

FOREIGN PATENT DOCUMENTS

| JP | A 2004-363096 | 12/2004 |
| JP | A 2008-166119 | 7/2008 |

(Continued)

OTHER PUBLICATIONS

Irikura et al., CA 62:15337, 1965.*

(Continued)

*Primary Examiner* — Laura L. Stockton
(74) *Attorney, Agent, or Firm* — Oliff PLC

(57) ABSTRACT

The photoelectric conversion device described herein includes a working electrode having a dye-supported metal oxide electrode in which a dye is supported on a metal oxide layer. The dye includes a structure represented by general formula (I)

[Formula 1]

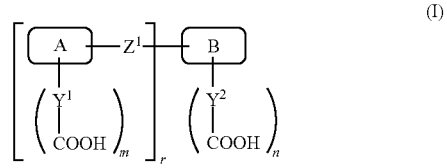

(I)

wherein A is a structure having a maximum absorption wavelength λmax of 350 to 500 nm in a methanol solution; B is a cyanine skeleton having a maximum absorption wavelength λmax of 500 to 700 nm in a methanol solution; $Z^1$ is any one divalent linking group selected from —CONR—, —NRCO—, —$SO_2$NR—, and —NR$SO_2$—; R in $Z^1$ is a hydrogen atom, an alkyl group having 1 to 8 carbon atoms, or an arylalkyl group having 7 to 20 carbon atoms; $Y^1$ and $Y^2$ are each independently an alkylene group having 1 to 8 carbon atoms, or a single bond, and may be the same or different; r is 1 or 2; m and n are each independently an integer of 0 to 2; and (m+n) is 1 or more.

8 Claims, 6 Drawing Sheets

(51) Int. Cl.
*C09B 23/16* (2006.01)
*H01G 9/20* (2006.01)

(56) References Cited

FOREIGN PATENT DOCUMENTS

| JP | A 2010-135281 | 6/2010 |
| TW | 200849618 A | 12/2008 |

OTHER PUBLICATIONS

Mar. 25, 2014 Office Action issued in Taiwanese Patent Application No. 100135929.

Jan. 10, 2012 Search Report issued in International Patent Application No. PCT/JP2011/072053 (with translation).

* cited by examiner

PHOTOELECTRIC CONVERSION DEVICE AND PHOTOELECTRIC CONVERSION DEVICE DYE, AND COMPOUND

TECHNICAL FIELD

The present invention relates to a photoelectric conversion device and a photoelectric conversion device dye, and a compound.

BACKGROUND ART

Conventionally, dyes have been widely used in various technical fields. As one example, in the field of photoelectric conversion devices, for example, a dye having photosensitization action is used in the working electrode of a dye-sensitized solar cell.

A dye-sensitized solar cell generally has an electrode having an oxide semiconductor as a support for a dye. Such a dye absorbs incident light and is excited, and this excited dye injects electrons into the support to perform photoelectric conversion. In this type of dye-sensitized solar cell, high energy conversion efficiency can be theoretically expected among organic solar cells. In addition, this type of dye-sensitized solar cell can be produced at lower cost than conventional solar cells using a silicon semiconductor, and therefore is considered to be very advantageous in terms of cost.

On the other hand, as dyes used in photoelectric conversion devices, organic dyes, such as ruthenium complex dyes and cyanine dyes, are widely known. Particularly, cyanine dyes have relatively high stability, and can be easily synthesized, and therefore, various studies have been made.

For example, Patent Document 1 discloses a cyanine dye that has a structure in which an indolenine skeleton is bonded to both ends of a methine chain skeleton, and further has a carboxylic acid group as an anchor group to be adsorbed on an oxide semiconductor electrode.

In addition, Patent Document 2 discloses a composite dye in which a plurality of component dyes having different excitation levels from each other are chemically bonded to each other, thereby forming a linear or branched structure for electron transfer, the linear or branched structure is held at one end by an n-type semiconductor, the other end is a free end, and in the linear or branched structure, the plurality of component dyes are arranged in the order in which the excitation level decreases from the end of the linear or branched structure held by the above n-type semiconductor toward the above free end.

Further, Patent Document 3 discloses a sensitizing dye in which a dye having an absorption maximum at 400 to 700 nm is bonded to a dye having an absorption maximum at 700 to 1500 nm by a divalent linking group.

CITATION LIST

Patent Document

Patent Document 1: Japanese Patent Laid-Open No. 2008-166119
Patent Document 2: Japanese Patent Laid-Open No. 2004-363096
Patent Document 3: Japanese Patent Laid-Open No. 2010-135281

SUMMARY OF INVENTION

Technical Problem

However, it cannot be said that conventional (uncombined) dyes, typified by the cyanine dye described in the above Patent Document 1, and the like, have a sufficiently wide absorption wavelength region, and it cannot be said that photoelectric conversion devices using these exhibit sufficient energy conversion efficiency.

Therefore, the widening of the absorption wavelength region has been studied, and for example, attempts to combine a plurality of dyes, as in the technique described in the above Patent Document 2, have been made. But, the combined dye described in the above Patent Document 2 sensitizes by two-photon excitation, and therefore, in a photoelectric conversion device using this, the current decreases to half, and high energy conversion efficiency is not obtained.

On the other hand, the combined dye described in the above Patent Document 3 has an absorption maximum at 700 to 1500 nm, and therefore, the LUMO of the dye is low, and it is difficult for the dye to exceed the conductor of a metal oxide. Therefore, electrons cannot be efficiently injected from the dye into a metal oxide semiconductor. Therefore, in a photoelectric conversion device using the combined dye described in the above Patent Document 3, high energy conversion efficiency is not obtained.

The present invention has been made in view of such circumstances, and it is an object of the present invention to provide a photoelectric conversion device that has excellent energy conversion efficiency and high durability, and a new dye that can implement such a photoelectric conversion device, and a compound that can be used as a precursor (intermediate) of such a new dye.

Solution to Problem

The present inventors have diligently studied over and over and, as a result, found that the above problems are solved by using a dye having a specific structure newly synthesized by the present inventors, leading to the completion of the present invention.

Specifically, the present invention provides the following <1> to <11>.

<1>
A photoelectric conversion device comprising a working electrode having a dye-supported metal oxide electrode in which a dye is supported on a metal oxide layer, wherein the dye has a structure represented by the following general formula (I):

[Formula 1]

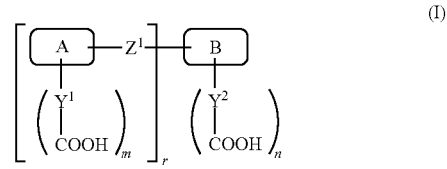

wherein A is a structure having a maximum absorption wavelength λmax of 350 to 500 nm in a methanol solution; B is a cyanine skeleton having a maximum absorption wavelength λmax of 500 to 700 nm in a methanol solution; $Z^1$ is any one divalent linking group selected from —CONR—, —NRCO—, —SO$_2$NR—, and —NRSO$_2$—; R in $Z^1$ is a hydrogen atom, an alkyl group having 1 to 8 carbon atoms, or an arylalkyl group having 7 to 20 carbon atoms; $Y^1$ and $Y^2$ are each independently an alkylene group having 1 to 8 carbon atoms, or a single bond, and may be the same or different; r is 1 or 2; m and n are each independently an integer of 0 to 2; and (m+n) is 1 or more.

<2>
The photoelectric conversion device according to <1>, wherein the dye has a structure represented by the following general formula (II):

[Formula 2]

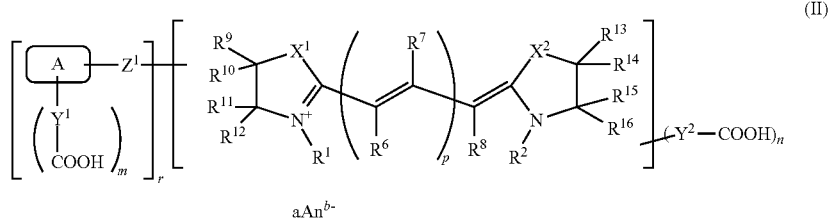

wherein $X^1$ and $X^2$ are each independently an oxygen atom, a sulfur atom, a selenium atom, $CR^3R^4$, or $NR^5$, and may be the same or different; $R^1$ to $R^5$ are each independently a hydrogen atom, an alkyl group having 1 to 20 carbon atoms, an alkenyl group having 2 to 8 carbon atoms, or an alkynyl group having 2 to 8 carbon atoms, and may be the same or different, where $R^1$ to $R^5$ may each be independently substituted by a halogen atom, a nitro group, a cyano group, an amino group, a hydroxyl group, an ether group, a carbonyl group, an aromatic ring, a heterocyclic ring, or a metallocenyl group, and $R^3$ and $R^4$ may be linked to form an alicyclic group having a 3- to 6-membered ring; $R^6$ to $R^8$ are each independently a hydrogen atom, an alkyl group having 1 to 8 carbon atoms, an aryl group having 6 to 12 carbon atoms, a halogen atom, or a cyano group, and may be the same or different; $R^9$ to $R^{16}$ are each independently a hydrogen atom, a halogen atom, an alkyl group having 1 to 20 carbon atoms, or an aryl group having 6 to 12 carbon atoms, and may be the same or different; in $R^9$ to $R^{16}$, $R^9$ and $R^{11}$ may be eliminated or $R^{13}$ and $R^{15}$ may be eliminated to each form an unsaturated bond, or $R^{10}$ and $R^{12}$ may be linked or $R^{14}$ and $R^{16}$ may be linked to each form a benzene ring which may have a substituent, a naphthalene ring which may have a substituent, or a phenanthrene ring which may have a substituent; p is 1 or 2; $Z^1$ in the formula replaces $R^1$ to $R^{16}$ or a hydrogen atom contained in $R^1$ to $R^{16}$; a substituent —$Y^2$—COOH in the formula replaces $R^1$ to $R^{16}$ or a hydrogen atom contained in $R^1$ to $R^{16}$; $An^{b-}$ is a b-valent anion; a is 1 or 2, and is a coefficient for keeping a charge of the entire dye neutral; b is 1 or 2; and m, n, r, $Z^1$, A, $Y^1$, and $Y^2$ are the same as described in general formula (I).
<3>
The photoelectric conversion device according to <2>, wherein the dye has a structure represented by the following general formula (III):

[Formula 3]

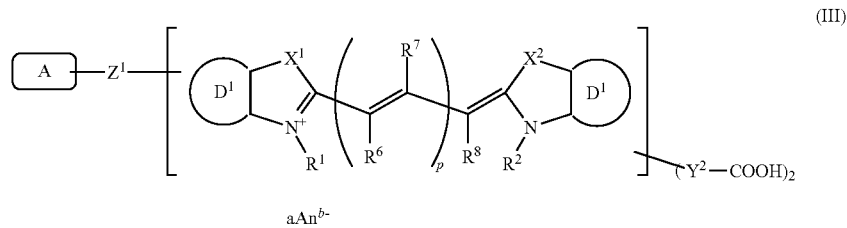

wherein $D^1$ and $D^2$ are each independently a benzene ring which may have a substituent, a naphthalene ring which may have a substituent, or a phenanthrene ring which may have a substituent, and may be the same or different; and two substituents —$Y^2$—COOH in the formula each replace $R^1$ to $R^8$ or a hydrogen atom contained in $R^1$ to $R^8$, or substitute the benzene ring, the naphthalene ring, or the phenanthrene ring represented by $D^1$ and $D^2$.
<4>
The photoelectric conversion device according to any one of items <1> to <3>, wherein the A is one selected from the group consisting of the following formulas (IV) to (VII):

[Formula 4]

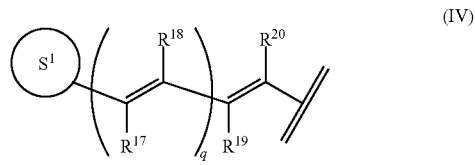

wherein $S^1$ is an aromatic ring which may have a substituent, or a heterocyclic ring which may have a substituent; $R^{17}$ to $R^{20}$ are each independently a hydrogen atom, an alkyl group having 1 to 8 carbon atoms, a halogen atom, or a cyano group, and may be the same or different; q is 0 or 1; and the substituent —$Y^1$—COOH substitutes $S^1$;

[Formula 5]

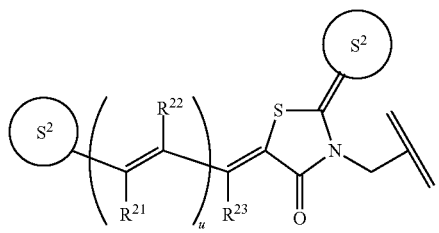

(V)

wherein $S^2$ is an aromatic ring which may have a substituent, or a heterocyclic ring which may have a substituent; $S^3$ is a sulfur atom or a structure represented by the following formula (Va); $R^{21}$ to $R^{23}$ are each independently a hydrogen atom, an alkyl group having 1 to 8 carbon atoms, a halogen atom, or a cyano group, and may be the same or different; $R^{24}$ is a hydrogen atom, an alkyl group having 1 to 20 carbon atoms, an aryl group having 6 to 30 carbon atoms, an arylalkyl group having 7 to 30 carbon atoms, or an anchor group; u is 0 or 1; and the substituent —$Y^1$—COOH substitutes $S^2$ and/or $S^3$:

[Formula 6]

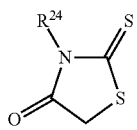

(Va)

[Formula 7]

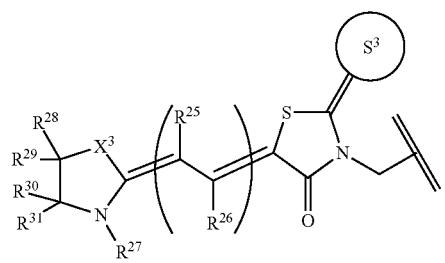

(VI)

wherein $R^{25}$ to $R^{26}$ are each independently a hydrogen atom, an alkyl group having 1 to 8 carbon atoms, a halogen atom, or a cyano group, and may be the same or different; $R^{27}$ is a hydrogen atom, an alkyl group having 1 to 20 carbon atoms, an aryl group having 6 to 30 carbon atoms, an arylalkyl group having 7 to 30 carbon atoms, or an anchor group; $R^{28}$ to $R^{31}$ are each independently a hydrogen atom, a halogen atom, an alkyl group having 1 to 20 carbon atoms, or an aryl group having 6 to 12 carbon atoms, and may be the same or different, where $R^{28}$ and $R^{30}$ may each be eliminated to form an unsaturated bond, or $R^{29}$ and $R^{31}$ may be linked to form a benzene ring which may have a substituent, a naphthalene ring which may have a substituent, or a phenanthrene ring which may have a substituent; t is 0 or 1; and the substituent —$Y^1$—COOH substitutes $S^3$; and

[Formula 8]

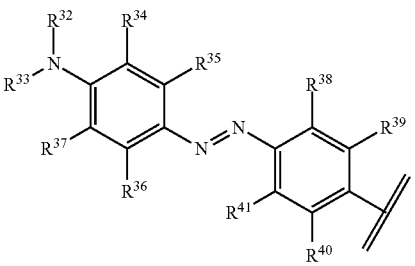

(VII)

wherein $R^{32}$ to $R^{33}$ are each independently a hydrogen atom, an alkyl group having 1 to 20 carbon atoms, or an arylalkyl group having 7 to 30 carbon atoms, and may be the same or different; and $R^{34}$ to $R^{41}$ are each independently a hydrogen atom, a halogen atom, a hydroxyl group, a cyano group, a nitro group, an alkyl group having 1 to 20 carbon atoms, an aryl group having 6 to 30 carbon atoms, or an arylalkyl group having 7 to 30 carbon atoms, and may be the same or different.

<5>

A photoelectric conversion device dye having a structure represented by the following general formula (I):

[Formula 9]

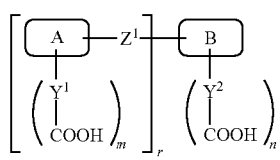

(I)

1p;3p wherein A is a structure having a maximum absorption wavelength λmax of 350 to 500 nm in a methanol solution; B is a cyanine skeleton having a maximum absorption wavelength λmax of 500 to 700 nm in a methanol solution; $Z^1$ is any one divalent linking group selected from —CONR—, —NRCO—, —$SO_2$NR—, and —NR$SO_2$—; R in $Z^1$ is a hydrogen atom, an alkyl group having 1 to 8 carbon atoms, or an arylalkyl group having 7 to 20 carbon atoms; $Y^1$ and $Y^2$ are each independently an alkylene group having 1 to 8 carbon atoms, or a single bond, and may be the same or different; r is 1 or 2; m and n are each independently an integer of 0 to 2; and (m+n) is 1 or more.

<6>

The photoelectric conversion device dye according to <5>, having a structure represented by the following general formula (II):

[Formula 10]

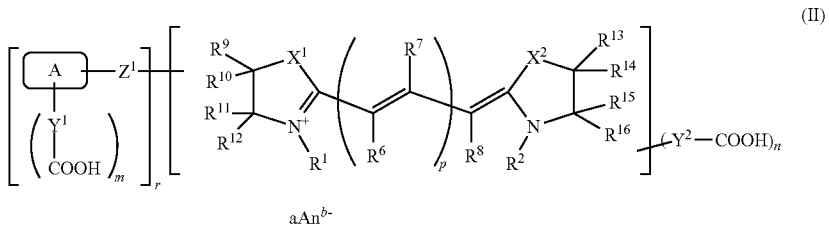

(II)

wherein $X^1$ and $X^2$ are each independently an oxygen atom, a sulfur atom, a selenium atom, $CR^3R^4$, or $NR^5$, and may be the same or different; $R^1$ to $R^5$ are each independently a hydrogen atom, an alkyl group having 1 to 20 carbon atoms, an alkenyl group having 2 to 8 carbon atoms, or an alkynyl group having 2 to 8 carbon atoms, and may be the same or different, where $R^1$ to $R^5$ may each be independently substituted by a halogen atom, a nitro group, a cyano group, an amino group, a hydroxyl group, an ether group, a carbonyl group, an aromatic ring, a heterocyclic ring, or a metallocenyl group, and $R^3$ and $R^4$ may be linked to form an alicyclic group having a 3- to 6-membered ring; $R^6$ to $R^8$ are each independently a hydrogen atom, an alkyl group having 1 to 8 carbon atoms, an aryl group having 6 to 12 carbon atoms, a halogen atom, or a cyano group, and may be the same or different; $R^9$ to $R^{16}$ are each independently a hydrogen atom, a halogen atom, an alkyl group having 1 to 20 carbon atoms, or an aryl group having 6 to 12 carbon atoms, and may be the same or different; in $R^9$ to $R^{16}$, $R^9$ and $R^{11}$ may be eliminated or $R^{13}$ and $R^{15}$ may be eliminated to each form an unsaturated bond, or $R^{10}$ and $R^{12}$ may be linked or $R^{14}$ and $R^{16}$ may be linked to each form a benzene ring which may have a substituent, a naphthalene ring which may have a substituent, or a phenanthrene ring which may have a substituent; p is 1 or 2; $Z^1$ in the formula replaces $R^1$ to $R^{16}$ or a hydrogen atom contained in $R^1$ to $R^{16}$; a substituent —$Y^2$—COOH in the formula replaces $R^1$ to $R^{16}$ or a hydrogen atom contained in $R^1$ to $R^{16}$; $An^{b-}$ is a b-valent anion; a is 1 or 2, and is a coefficient for keeping a charge of the entire dye neutral; b is 1 or 2; and m, n, r, $Z^1$, A, $Y^1$, and $Y^2$ are the same as described in general formula (I).

<7>

The photoelectric conversion device dye according to <6>, having a structure represented by the following general formula (III):

wherein $D^1$ and $D^2$ are each independently a benzene ring which may have a substituent, a naphthalene ring which may have a substituent, or a phenanthrene ring which may have a substituent, and may be the same or different; and two substituents —$Y^2$—COOH in the formula each replace $R^1$ to $R^8$ or a hydrogen atom contained in $R^1$ to $R^8$, or substitute the benzene ring, the naphthalene ring, or the phenanthrene ring represented by $D^1$ and $D^2$.

<8>

The photoelectric conversion device dye according to any one of items <5> to <7>, wherein the A is one selected from the group consisting of the following formulas (IV) to (VII):

[Formula 12]

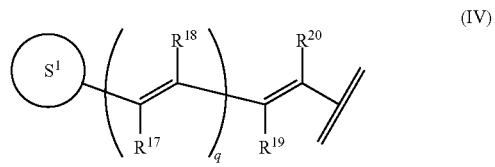

(IV)

wherein $S^1$ is an aromatic ring which may have a substituent, or a heterocyclic ring which may have a substituent; $R^{17}$ to $R^{20}$ are each independently a hydrogen atom, an alkyl group having 1 to 8 carbon atoms, a halogen atom, or a cyano group, and may be the same or different; q is 0 or 1; and the substituent —$Y^1$—COOH substitutes $S^1$;

[Formula 11]

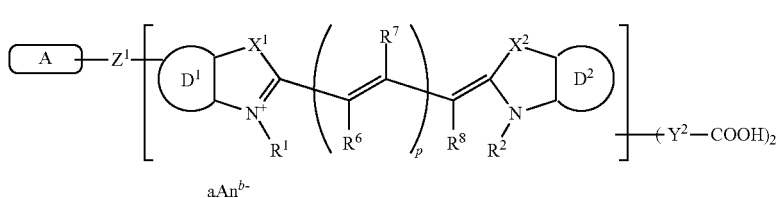

(III)

[Formula 13]

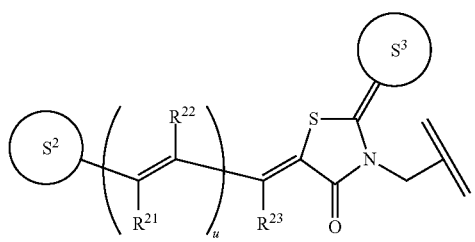

(V)

wherein $S^2$ is an aromatic ring which may have a substituent, or a heterocyclic ring which may have a substituent; $S^3$ is a sulfur atom or a structure represented by the following formula (Va); $R^{21}$ to $R^{23}$ are each independently a hydrogen atom, an alkyl group having 1 to 8 carbon atoms, a halogen atom, or a cyano group, and may be the same or different; $R^{24}$ is a hydrogen atom, an alkyl group having 1 to 20 carbon atoms, an aryl group having 6 to 30 carbon atoms, an arylalkyl group having 7 to 30 carbon atoms, or an anchor group, u is 0 or 1; and the substituent —$Y^1$—COOH substitutes $S^2$ and/or $S^3$:

[Formula 14]

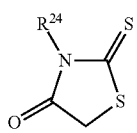

(Va)

[Formula 15]

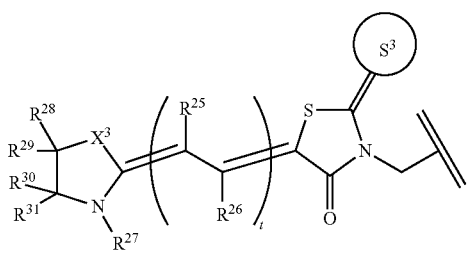

(VI)

wherein $R^{25}$ to $R^{26}$ are each independently a hydrogen atom, an alkyl group having 1 to 8 carbon atoms, a halogen atom, or a cyano group, and may be the same or different, $R^{27}$ is a hydrogen atom, an alkyl group having 1 to 20 carbon atoms, an aryl group having 6 to 30 carbon atoms, an arylalkyl group having 7 to 30 carbon atoms, or an anchor group; $R^{28}$ to $R^{31}$ are each independently a hydrogen atom, a halogen atom, an alkyl group having 1 to 20 carbon atoms, or an aryl group having 6 to 12 carbon atoms, and may be the same or different, where $R^{28}$ and $R^{30}$ may each be eliminated to form an unsaturated bond, or $R^{29}$ and $R^{31}$ may be linked to form a benzene ring which may have a substituent, a naphthalene ring which may have a substituent, or a phenanthrene ring which may have a substituent; t is 0 or 1; and the substituent —$Y^1$—COOH substitutes $S^3$; and

[Formula 16]

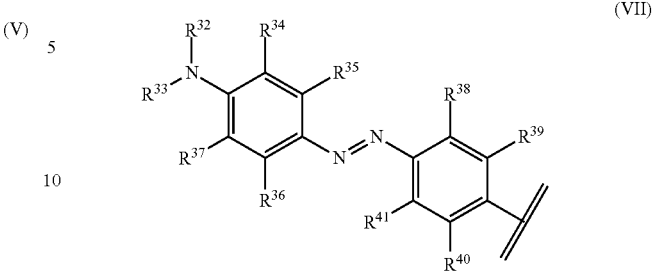

(VII)

wherein $R^{32}$ to $R^{33}$ are each independently a hydrogen atom, an alkyl group having 1 to 20 carbon atoms, or an arylalkyl group having 7 to 30 carbon atoms, and may be the same or different; and $R^{34}$ to $R^{41}$ are each independently a hydrogen atom, a halogen atom, a hydroxyl group, a cyano group, a nitro group, an alkyl group having 1 to 20 carbon atoms, an aryl group having 6 to 30 carbon atoms, or an arylalkyl group having 7 to 30 carbon atoms, and may be the same or different.

<9>

A compound having a structure represented by the following formula (IX):

[Formula 17]

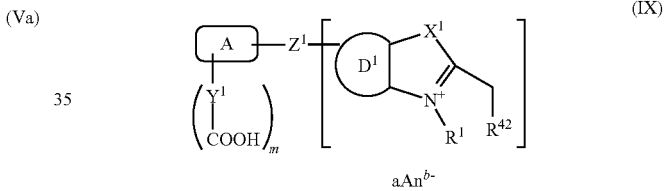

(IX)

$aAn^{b-}$ wherein A is a structure having a maximum absorption wavelength λmax of 350 to 500 nm in a methanol solution, $Z^1$ is any one divalent linking group selected from —CONR—, —NRCO—, —SO$_2$NR—, and —NRSO$_2$—; R in $Z^1$ is a hydrogen atom, an alkyl group having 1 to 8 carbon atoms, or an arylalkyl group having 7 to 20 carbon atoms; $D^1$ is a benzene ring which may have a substituent, a naphthalene ring which may have a substituent, or a phenanthrene ring which may have a substituent; $R^1$ is a hydrogen atom, an alkyl group having 1 to 20 carbon atoms, an alkenyl group having 2 to 8 carbon atoms, or an alkynyl group having 2 to 8 carbon atoms, each of which may be substituted by a halogen atom, a nitro group, a cyano group, an amino group, a hydroxyl group, an ether group, a carbonyl group, an aromatic ring, a heterocyclic ring, or a metallocenyl group; $R^{42}$ are each independently a hydrogen atom, an alkyl group having 1 to 8 carbon atoms, an aryl group having 6 to 12 carbon atoms, a halogen atom, or a cyano group, and may be the same or different; $X^1$ is an oxygen atom, a sulfur atom, a selenium atom, $CR^3R^4$, or $NR^5$; $R^3$ to $R^5$ are each independently a hydrogen atom, an alkyl group having 1 to 20 carbon atoms, an alkenyl group having 2 to 8 carbon atoms, or an alkynyl group having 2 to 8 carbon atoms, and may be the same or different; $R^3$ to $R^5$ may each be independently substituted by a halogen atom, a nitro group, a cyano group, an amino group, a hydroxyl group, an ether group, a carbonyl group, an aromatic ring, a heterocyclic ring, or a metallocenyl group, and $R^3$ and $R^4$ may be linked to form an alicyclic group having a 3- to 6-membered ring; $Y^1$ is an alkylene group having 1 to 8 carbon atoms, or a single bond; m is 0 to 2; $An^{b-}$ is a b-valent anion; a is 1 or 2, and is a coefficient for keeping a charge of the entire dye neutral; and b is 1 or 2.

The compound having the structure represented by the above formula (IX) is equivalent to a compound having a structure represented by the following formula (IX)' in terms of synthesis.

[Formula 18]

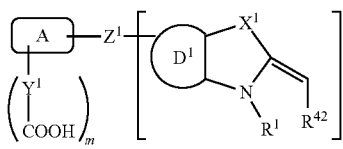

(IX)' wherein A, $Z^1$, $D^1$, $R^1$, $R^{42}$, $X^1$, $Y^1$, and m are the same as described in the above formula (IX).

<10>

The compound according to <9>, having a structure represented by the following formula (X):

[Formula 19]

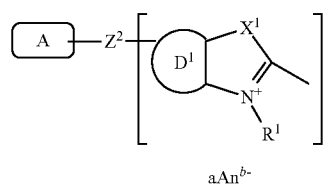

(X)

wherein A is a structure having a maximum absorption wavelength λmax of 350 to 500 nm in a methanol solution; $Z^2$ is any one divalent linking group selected from —CONR—, —NRCO—, —SO$_2$NR—, and —NRSO$_2$—, R in $Z^2$ is a hydrogen atom, an alkyl group having 1 to 8 carbon atoms, or an arylalkyl group having 7 to 20 carbon atoms; $D^1$ is a benzene ring which may have a substituent, a naphthalene ring which may have a substituent, or a phenanthrene ring which may have a substituent; $R^1$ is a hydrogen atom, an alkyl group having 1 to 20 carbon atoms, an alkenyl group having 2 to 8 carbon atoms, or an alkynyl group having 2 to 8 carbon atoms, each of which may be substituted by a halogen atom, a nitro group, a cyano group, an amino group, a hydroxyl group, an ether group, a carbonyl group, an aromatic ring, a heterocyclic ring, or a metallocenyl group, $X^1$ is an oxygen atom, a sulfur atom, a selenium atom, $CR^3R^4$, or $NR^5$; $R^3$ to $R^5$ are each independently a hydrogen atom, an alkyl group having 1 to 20 carbon atoms, an alkenyl group having 2 to 8 carbon atoms, or an alkynyl group having 2 to 8 carbon atoms, and may be the same or different, where $R^3$ to $R^5$ may each be independently substituted by a halogen atom, a nitro group, a cyano group, an amino group, a hydroxyl group, an ether group, a carbonyl group, an aromatic ring, a heterocyclic ring, or a metallocenyl group, and $R^3$ and $R^4$ may be linked to form an alicyclic group having a 3- to 6-membered ring; $An^{b-}$ is a b-valent anion; a is 1 or 2, and is a coefficient for keeping the charge of the entire dye neutral; and b is 1 or 2.

<11>

The compound according to item <9> or <10>, wherein the A is one selected from the group consisting of the following formulas (IV) to (VII):

[Formula 20]

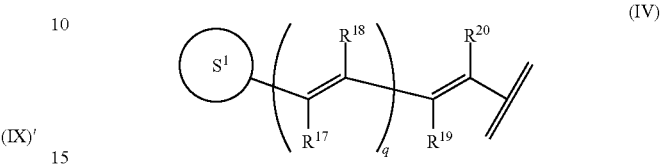

(IV)

wherein $S^1$ is an aromatic ring which may have a substituent, or a heterocyclic ring which may have a substituent; $R^{17}$ to $R^{20}$ are each independently a hydrogen atom, an alkyl group having 1 to 8 carbon atoms, a halogen atom, or a cyano group, and may be the same or different; q is 0 or 1, and the substituent —$Y^1$—COOH substitutes $S^1$;

[Formula 21]

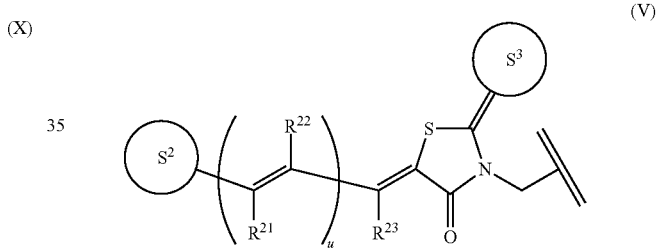

(V)

wherein $S^2$ is an aromatic ring which may have a substituent, or a heterocyclic ring which may have a substituent; $S^3$ is a sulfur atom or a structure represented by the following formula (Va); $R^{21}$ to $R^{23}$ are each independently a hydrogen atom, an alkyl group having 1 to 8 carbon atoms, a halogen atom, or a cyano group, and may be the same or different; $R^{24}$ is a hydrogen atom, an alkyl group having 1 to 20 carbon atoms, an aryl group having 6 to 30 carbon atoms, an arylalkyl group having 7 to 30 carbon atoms, or an anchor group; u is 0 or 1; and the substituent —$Y^1$—COOH substitutes $S^2$ and/or $S^3$:

[Formula 22]

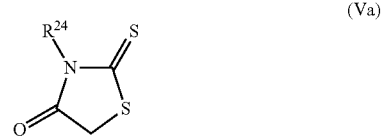

(Va)

13
-continued

[Formula 23]

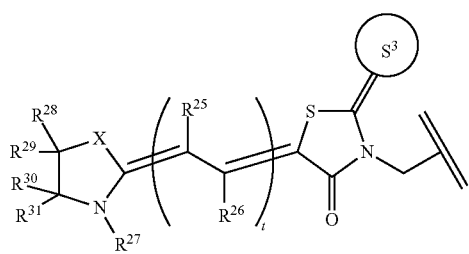

(VI)

wherein $R^{25}$ to $R^{26}$ are each independently a hydrogen atom, an alkyl group having 1 to 8 carbon atoms, a halogen atom, or a cyano group, and may be the same or different; $R^{27}$ is a hydrogen atom, an alkyl group having 1 to 20 carbon atoms, an aryl group having 6 to 30 carbon atoms, an arylalkyl group having 7 to 30 carbon atoms, or an anchor group; $R^{28}$ to $R^{31}$ are each independently a hydrogen atom, a halogen atom, an alkyl group having 1 to 20 carbon atoms, or an aryl group having 6 to 12 carbon atoms, and may be the same or different, where $R^{28}$ and $R^{30}$ may each be eliminated to form an unsaturated bond, or $R^{29}$ and $R^{31}$ may be linked to form a benzene ring which may have a substituent, a naphthalene ring which may have a substituent, or a phenanthrene ring which may have a substituent; t is 0 or 1; and the substituent —$Y^1$—COOH substitutes $S^3$; and

[Formula 24]

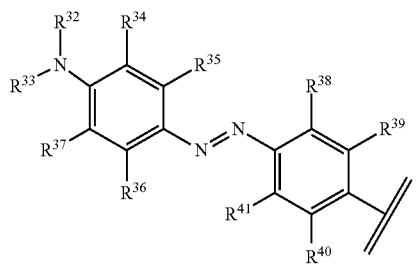

(VII)

wherein $R^{32}$ to $R^{33}$ are each independently a hydrogen atom, an alkyl group having 1 to 20 carbon atoms, or an arylalkyl group having 7 to 30 carbon atoms, and may be the same or different; and $R^{34}$ to $R^{41}$ are each independently a hydrogen atom, a halogen atom, a hydroxyl group, a cyano group, a nitro group, an alkyl group having 1 to 20 carbon atoms, an aryl group having 6 to 30 carbon atoms, or an arylalkyl group having 7 to 30 carbon atoms, and may be the same or different.

Advantageous Effects of Invention

According to the present invention, a photoelectric conversion device dye that has a wide absorption wavelength region, and has not only excellent adsorption properties (adhesiveness) on a metal oxide layer but also excellent energy transfer efficiency is implemented. Therefore, by using this photoelectric conversion device dye, a photoelectric conversion device that has enhanced photoelectric conversion characteristics and durability can be easily and reliably implemented.

14
BRIEF DESCRIPTION OF DRAWINGS

DESCRIPTION OF EMBODIMENT

Figure 1:
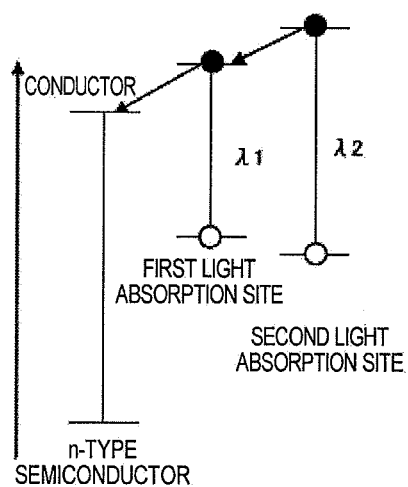
FIG. 1 is an explanatory diagram showing the presumed mechanism of the excitation and sensitization action of a dye in this embodiment.

An embodiment of the present invention will be described below. Like numerals refer to like elements, and redundant description is omitted. In addition, positional relationships, such as top, bottom, left, and right, are based on the positional relationships shown in the drawings unless otherwise specified. Further, the dimensional ratios in the drawings are not limited to the ratios shown. In addition, the following embodiment is illustration for explaining the present invention, and the present invention is not limited only to the embodiment.

A dye in this embodiment can be preferably used for a photoelectric conversion device, such as a dye-sensitized solar cell, and is a compound having a structure represented by general formula (I). The compound having the structure represented by general formula (1) has adsorption properties (bonding properties) on a metal oxide layer (support) comprising a metal oxide semiconductor material, and absorbs light, is excited, and injects electrons into the support.

[Formula 25]

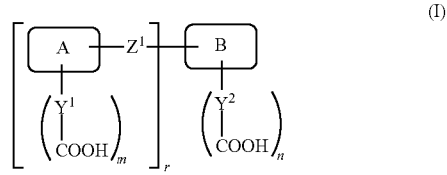

(I)

wherein A is a structure having a maximum absorption wavelength λmax of 350 to 500 nm in a methanol solution; B is a cyanine skeleton having a maximum absorption wavelength λmax of 500 to 700 nm in a methanol solution; $Z^1$ is any one divalent linking group selected from —CONR—, —NRCO—, —$SO_2$NR—, and —NR$SO_2$—; R in $Z^1$ is a hydrogen atom, an alkyl group having 1 to 8 carbon atoms, or an arylalkyl group having 7 to 20 carbon atoms; $Y^1$ and $Y^2$ are each independently an alkylene group having 1 to 8 carbon atoms, or a single bond, and may be the same or different; r is 1 or 2; m and n are each independently an integer of 0 to 2; and (m+n) is 1 or more.

In general formula (I), the structure having a maximum absorption wavelength λmax of 350 to 500 nm in a methanol solution, which is A, is not particularly limited, and examples thereof include a structure in which m+1 hydrogen atoms or monovalent substituents are abstracted from a yellow dye having a maximum absorption wavelength λmax of 350 to 500 nm. Examples of such a yellow dye include, but are not particularly limited to, fluorescein, rhodamine, cyanine, merocyanine, hemicyanine, azo, polycyclic quinone, indigo, diphenylmethane, benzophenone, pyrene, perylene, semi-squarylium, metal-free porphyrin, and metal porphyrin.

In general formula (I), the cyanine skeleton having a maximum absorption wavelength λmax of 500 to 700 nm in a methanol solution, which is B, is not particularly limited, and examples thereof include a structure in which n+r+1 hydrogen atoms or monovalent substituents are abstracted from a cyanine dye having a maximum absorption wavelength λmax of 500 to 700 nm in a methanol solution.

In general formula (I), the alkyl group having 1 to 8 carbon atoms is not particularly limited, and may be any of linear, branched, or cyclic. Specific examples thereof include methyl, ethyl, propyl, isopropyl, n-butyl, isobutyl, s-butyl, t-butyl, pentyl, isopentyl, neopentyl, n-hexyl, 1-methylbutyl, isohexyl, 2-ethylhexyl, 2-methylhexyl, cyclohexyl, cyclopentyl, cyclohexylmethyl, n-heptyl, and n-octyl.

In general formula (I), the arylalkyl group having 7 to 20 carbon atoms is not particularly limited, and may be any of linear, branched, or cyclic. Specific examples thereof include benzyl, phenylethyl, phenylpropyl, p-methylbenzyl, and naphthylmethyl.

In general formula (I), the alkylene group having 1 to 8 carbon atoms is not particularly limited, and may be any of linear, branched, or cyclic. Specific examples thereof include methylene, ethylene, propylene, butylene, pentylene, and hexylene.

The detailed mechanism of action for the fact that the dye in this embodiment has a wide absorption wavelength region, and has not only excellent adsorption properties (adhesiveness) on a metal oxide layer but also excellent energy transfer efficiency is uncertain, but is presumed as follows.

In the dye in this embodiment, the structure having a maximum absorption wavelength λmax of 350 to 500 nm in a methanol solution (second light absorption site) and the cyanine skeleton having a maximum absorption wavelength λmax of 500 to 700 nm in a methanol solution (first light absorption site) are linked by the linking group $Z^1$, and thus, the absorption wavelength region is widened. Moreover, an amide bond or a sulfonamide bond is used as the linking group, and therefore, energy transfer from the second light absorption site B to the first light absorption site A is efficiently performed. For example, it has become clear from the findings of the present inventors that in the comparison of a dye of the following formula (A) and a dye of the following formula (B), the fluorescence quantum yield of cyanine when the second light absorption site is excited is higher in the dye of the following formula (A) (5.1% in the dye of the following formula (A), and 0.1% in the dye of the following formula (B)).

[Formula 26]

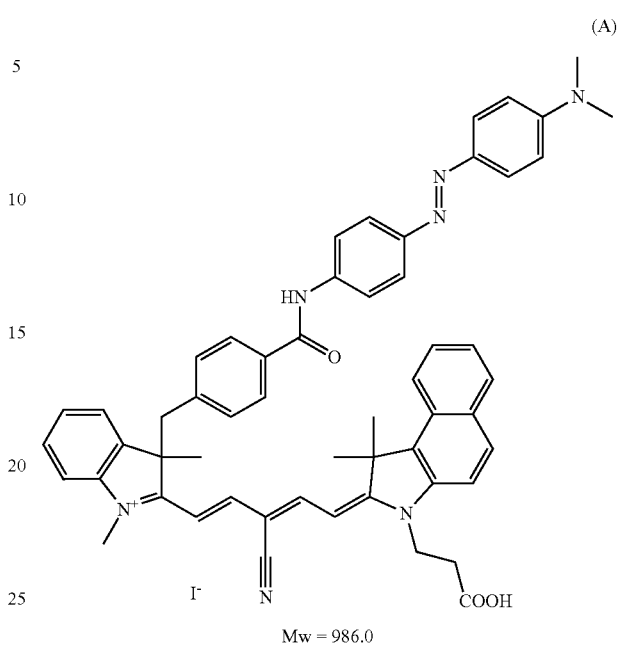

(A)

Mw = 986.0

[Formula 27]

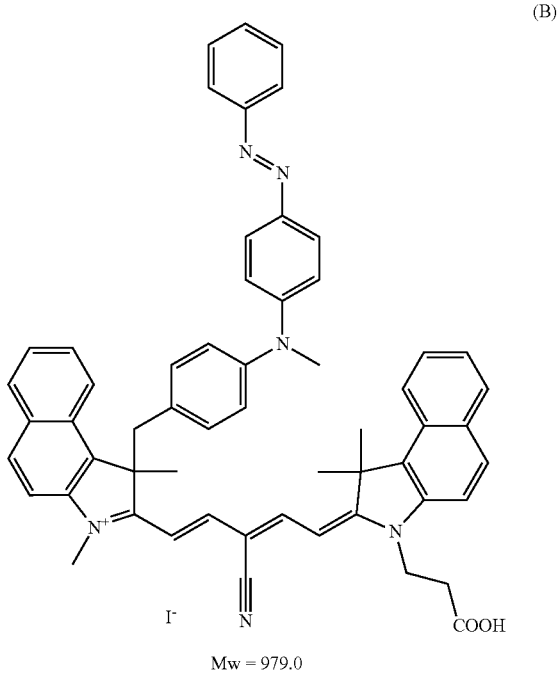

(B)

Mw = 979.0

Moreover, it has been confirmed that in the dye in this embodiment, light emission from the first light absorption site A is observed with high efficiency even if the second light absorption site B is excited. This suggests that even if the second light absorption site B is a material with low injection into a metal oxide, light energy absorbed by the first light absorption site and light energy absorbed by the second light absorption site are both transferred to a metal oxide semiconductor with high efficiency when a material with high electron injection into a metal oxide is selected for the first light absorption site A.

Conventionally, in order to widen the absorption wavelength region, using two or more (uncombined) dyes having different absorption wavelength regions, in combination, has also been studied. However, even if two or more (uncombined) dyes are used in combination, it is difficult to adsorb the dyes on a metal oxide surface in an intended adsorption proportion (sufficiently adsorb a dye having poor adsorption properties on a metal oxide surface) because the adsorption properties of the dyes on the metal oxide surface are different. Therefore, it is difficult to widen the absorption wavelength region. In addition, it is considered that the sites of a metal oxide surface on which dyes can be adsorbed are limited. Therefore, even if an attempt is made to mix two or more (uncombined) dyes and adsorb the mixed dyes on a metal oxide surface, these are adsorbed sharing the limited sites, and therefore, the amount of the adsorbed dyes per unit area cannot be increased. On the other hand, in the case of a (combined) dye linked by the linking group $Z^1$, like the dye in this embodiment, the (combined) dye is a single dye, and therefore, it is not necessary to share the adsorption sites with other dyes as described above. In addition, although the (combined) dye is a single dye, two dye structures are included, and therefore, the amount of the adsorbed dye (dye structures) per unit area can be increased. Further, —$Y^1$—COOH or —$Y^2$—COOH, which is an anchor group, is protected by the bulkiness of the linking group $Z^1$ and the first light absorption site A, and therefore, high resistance in a peeling test can be shown.

Furthermore, in the dye in this embodiment, —$Y^1$—COOH or —$Y^2$—COOH is introduced as an anchor group, and therefore, the adsorption properties (adhesiveness) on a metal oxide surface are enhanced. Thus, not only electron transfer from the dye to a metal oxide semiconductor is promoted, but also the amount of the dye adsorbed on a metal oxide surface is enhanced. It is considered that as a result of these actions in combination, in a photoelectric conversion device using the dye in this embodiment, the proportion of the amount of electrons injected from the dye in this embodiment into a metal oxide semiconductor is high with respect to the amount of emitted light, and IPCE (Incident Photons to Current conversion Efficiency) is improved, and as a result, conversion efficiency is improved, and durability is enhanced. However, the actions are not limited to these. IPCE represents the conversion proportion of the number of electrons of photocurrent to the number of photons of emitted light in a photoelectric conversion device, and is obtained by IPCE (%)=Isc×1240/λ×1/φ wherein Isc is short circuit current, λ is wavelength, and φ is incident light intensity.

The structure represented by the above general formula (I) is preferably a structure represented by the following general formula (II):

[Formula 28]

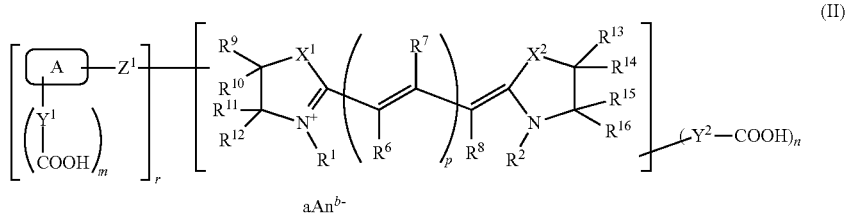

wherein $X^1$ and $X^2$ are each independently an oxygen atom, a sulfur atom, a selenium atom, $CR^3R^4$, or $NR^5$, and may be the same or different; $R^1$ to $R^5$ are each independently a hydrogen atom, an alkyl group having 1 to 20 carbon atoms, an alkenyl group having 2 to 8 carbon atoms, or an alkynyl group having 2 to 8 carbon atoms, and may be the same or different, where $R^1$ to $R^5$ may each be independently substituted by a halogen atom (F, Cl, Br, or the like), a nitro group, a cyano group, an amino group, a hydroxyl group, an ether group, a carbonyl group, an aromatic ring, a heterocyclic ring, or a metallocenyl group, and $R^3$ and $R^4$ may be linked to form an alicyclic group having a 3- to 6-membered ring; $R^6$ to $R^8$ are each independently a hydrogen atom, an alkyl group having 1 to 8 carbon atoms, an aryl group having 6 to 12 carbon atoms, a halogen atom (F, Cl, Br, or the like), or a cyano group, and may be the same or different; $R^9$ to $R^{16}$ are each independently a hydrogen atom, a halogen atom (F, Cl, Br, or the like), an alkyl group having 1 to 20 carbon atoms, or an aryl group having 6 to 12 carbon atoms, and may be the same or different; in $R^9$ to $R^{16}$, $R^9$ and $R^{11}$ may be eliminated or $R^{13}$ and $R^{15}$ may be eliminated to each form an unsaturated bond, or $R^{10}$ and $R^{12}$ may be linked or $R^{14}$ and $R^{16}$ may be linked to each form a benzene ring which may have a substituent, a naphthalene ring which may have a substituent, or a phenanthrene ring which may have a substituent; p is 1 or 2; $Z^1$ in the formula replaces $R^1$ to $R^{16}$ or a hydrogen atom contained in $R^1$ to $R^{16}$; a substituent —$Y^2$—COOH in the formula replaces $R^1$ to $R^{16}$ or a hydrogen atom contained in $R^1$ to $R^{16}$; $An^{b-}$ is a b-valent anion; a is 1 or 2, and is a coefficient for keeping the charge of the entire dye neutral; b is 1 or 2; and m, n, r, $Z^1$, A, $Y^1$, and $Y^2$ are the same as described in general formula (I).

In general formula (II), the alkyl group having 1 to 20 carbon atoms is not particularly limited, and may be any of linear, branched, or cyclic. Specific examples thereof include methyl, ethyl, propyl, isopropyl, n-butyl, isobutyl, s-butyl, t-butyl, pentyl, isopentyl, neopentyl, n-hexyl, 1-methylbutyl, isohexyl, 2-ethylhexyl, 2-methylhexyl, cyclohexyl, cyclopentyl, cyclohexylmethyl, n-heptyl, n-octyl, n-decyl, n-hexadecyl, and n-dodecyl.

In general formula (II), the alkenyl group having 2 to 8 carbon atoms is not particularly limited, and examples thereof include a vinyl group, an allyl group, a butenyl group, a hexenyl group, and a decenyl group.

In general formula (II), the alkynyl group having 2 to 8 carbon atoms is not particularly limited, and examples thereof include an ethynyl group and a propynyl group.

In general formula (II), the aromatic ring and the heterocyclic ring are not particularly limited, and examples thereof include benzene, naphthalene, anthracene, phenanthrene, pyrrole, furan, thiophene, imidazole, oxazole, thiazole, pyrazole, isoxazole, isothiazole, benzofuran, benzothiophene, benzimidazole, benzoxazole, benzothiazole, indole, indolenine, fluorene, carbazole, pyridine, pyridazine, pyrimidine, pyrazine, piperidine, piperazine, morpholine, 2H-pyran, and 4H-pyran. Examples of the substituent of the aromatic ring and the heterocyclic ring include, but are not particularly limited to, a hydroxyl group, a carboxyl group, a nitro group, a cyano group, halogen atoms (F, Cl, Br, and the like), the alkyl groups having 1 to 8 carbon atoms described above, the arylalkyl groups having 7 to 30 carbon atoms described above, the amino groups described above, alkyl halide groups having 1 to 4 or less carbon atoms (for example, $CF_3$ and $CCl_3$), and alkoxy groups having 1 to 4 carbon atoms (for example, methoxy, ethoxy, propyloxy, isopropyloxy, butyloxy, sec-butyloxy, and tert-butyloxy).

In general formula (II), examples of the alicyclic group when $R^3$ and $R^4$ are linked to form an alicyclic group having a 3- to 6-membered ring include cyclopropane, cyclobutane, cyclopentane, and cyclohexane.

In general formula (II), the alkyl group having 1 to 8 carbon atoms is not particularly limited, and may be any of linear, branched, or cyclic. Specific examples thereof include methyl, ethyl, propyl, isopropyl, n-butyl, isobutyl, s-butyl, t-butyl, pentyl, isopentyl, neopentyl, n-hexyl, 1-methylbutyl, isohexyl, 2-ethylhexyl, 2-methylhexyl, cyclohexyl, cyclopentyl, cyclohexylmethyl, n-heptyl, and n-octyl.

In general formula (II), the aryl group having 6 to 12 carbon atoms is not particularly limited, and specific examples thereof include a phenyl group, a naphthyl group, an azulenyl group, a phenanthrene group, and a biphenyl group.

In general formula (II), the anion of $An^{b-}$ is a counteranion for keeping the charge of the entire dye neutral, and any can be used as long as it is a monovalent or divalent anion. In $An^{b-}$ in general formula (II), specific examples of the anion in the case of b=1 (monovalent anion; $An^-$) are not particularly limited, and include a halide ion, such as a fluoride ion ($F^-$), a chloride ion ($Cl^-$), a bromide ion ($Br^-$), or an iodide ion ($I^-$), an inorganic anion, such as a hexafluorophosphate ion ($PF_6^-$), a hexafluoroantimonate ion ($SbF_6^-$), a perchlorate ion ($ClO_4^-$), a tetrafluoroborate ion ($BF_4^-$), a chlorate ion, or a thiocyanate ion, an organic sulfonate anion, such as a benzenesulfonate ion, a toluenesulfonate ion, a trifluoromethanesulfonate ion, a diphenylamine-4-sulfonate ion, a 2-amino-4-methyl-5-chlorobenzenesulfonate ion, a 2-amino-5-nitrobenzenesulfonate ion, a N-alkyldiphenylamine-4-sulfonate ion, or a N-aryldiphenylamine-4-sulfonate ion, and an organic phosphate anion, such as an octyl phosphate ion, a dodecyl phosphate ion, an octadecyl phosphate ion, a phenyl phosphate ion, a nonylphenyl phosphate ion, or a 2,2'-methylenebis(4,6-di-t-butylphenyl)phosphonate ion, and in addition, a bistrifluoromethylsulfonylimide ion, a bisperfluorobutanesulfonylimide ion, a perfluoro-4-ethylcyclohexanesulfonate ion, a tetrakis(pentafluorophenyl)borate ion, and a tris(fluoroalkylsulfonyl) carbanion. In addition, in $An^{b-}$ in general formula (II), the anion in the case of b=2 (divalent anion; $An^{2-}$) is not particularly limited, and examples thereof include a sulfate ion ($SO_4^{2-}$), a benzenedisulfonate ion, and a naphthalenedisulfonate ion. In addition, the dye in this embodiment may be the so-called inner salt in which a salt is formed in a molecule. In this case, in the dye in this embodiment, for example, an acidic group, such as a —$CH_2CH_2COOH$ group, introduced into the nitrogen atom of an indolenine skeleton is ionized.

The structure represented by the above general formula (II) is preferably a structure represented by the following general formula (III):

[Formula 29]

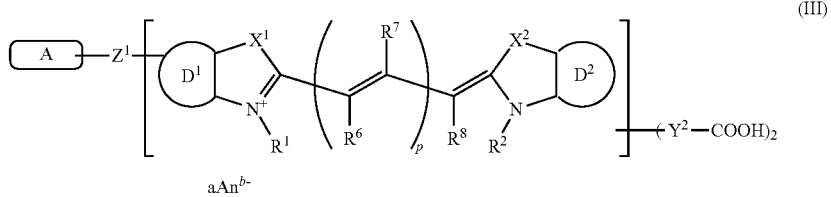

(III)

wherein $D^1$ and $D^2$ are each independently a benzene ring which may have a substituent, a naphthalene ring which may have a substituent, or a phenanthrene ring which may have a substituent, and may be the same or different; and two substituents —$Y^2$—COOH in the formula each replace $R^1$ to $R^8$ or a hydrogen atom contained in $R^1$ to $R^8$, or substitute the benzene ring, the naphthalene ring, or the phenanthrene ring represented by $D^1$ and $D^2$.

In the structures represented by the above general formulas (I) to (III), A, which is the structure having a maximum absorption wavelength λmax of 350 to 500 nm in a methanol solution, is preferably any one of the following formulas (IV) to (VII):

[Formula 30]

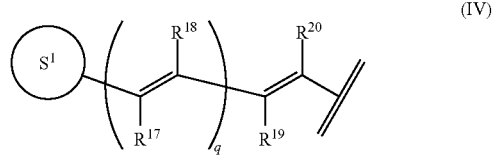

(IV)

wherein $S^1$ is an aromatic ring which may have a substituent, or a heterocyclic ring which may have a substituent; $R^{17}$ to $R^{20}$ are each independently a hydrogen atom, an alkyl group having 1 to 8 carbon atoms, a halogen atom (F, Cl, Br, or the like), or a cyano group, and may be the same or different; q is 0 or 1; and the above substituent —$Y^1$—COOH substitutes $S^1$;

[Formula 31]

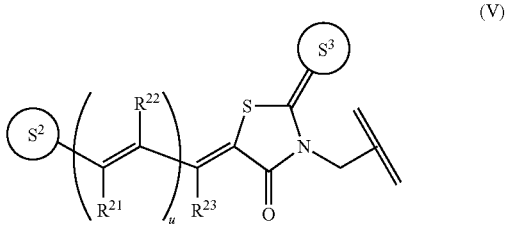

(V)

wherein $S^2$ is an aromatic ring which may have a substituent, or a heterocyclic ring which may have a substituent; $S^3$ is a sulfur atom or a structure represented by the following formula (Va); $R^{21}$ to $R^{23}$ are each independently a hydrogen atom, an alkyl group having 1 to 8 carbon atoms, a halogen atom, or a cyano group, and may be the same or different; $R^{24}$ is a hydrogen atom, an alkyl group having 1 to 20 carbon atoms, an aryl group having 6 to 30 carbon atoms, an arylalkyl group having 7 to 30 carbon atoms, or an anchor group; u is 0 or 1; and the above substituent —$Y^1$—COOH substitutes $S^2$ and/or $S^3$:

[Formula 32]

(Va)

[Formula 33]

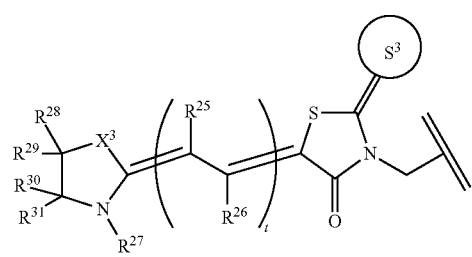

(VI)

wherein $R^{25}$ to $R^{26}$ are each independently a hydrogen atom, an alkyl group having 1 to 8 carbon atoms, a halogen atom, or a cyano group, and may be the same or different; $R^{27}$ is a hydrogen atom, an alkyl group having 1 to 20 carbon atoms, an aryl group having 6 to 30 carbon atoms, an arylalkyl group having 7 to 30 carbon atoms, or an anchor group; $R^{28}$ to $R^{31}$ are each independently a hydrogen atom, a halogen atom, an alkyl group having 1 to 20 carbon atoms, or an aryl group having 6 to 12 carbon atoms, and may be the same or different, where $R^{28}$ and $R^{30}$ may each be eliminated to form an unsaturated bond, or $R^{29}$ and $R^{31}$ may be linked to form a benzene ring which may have a substituent, a naphthalene ring which may have a substituent, or a phenanthrene ring which may have a substituent; t is 0 or 1; and the above substituent —$Y^1$—COOH substitutes $S^3$; and

[Formula 34]

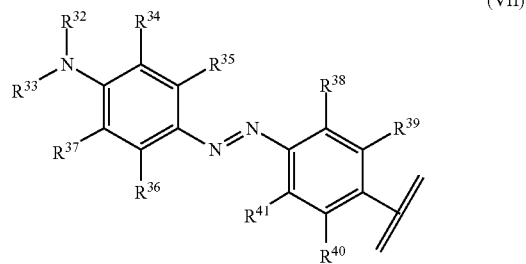

(VII)

wherein $R^{32}$ to $R^{33}$ are each independently a hydrogen atom, an alkyl group having 1 to 20 carbon atoms, or an arylalkyl group having 7 to 30 carbon atoms, and may be the same or different; and $R^{34}$ to $R^{41}$ are each independently a hydrogen atom, a halogen atom, a hydroxyl group, a cyano group, a nitro group, an alkyl group having 1 to 20 carbon atoms, an aryl group having 6 to 30 carbon atoms, or an arylalkyl group having 7 to 30 carbon atoms, and may be the same or different.

In the above formulas (IV) to (VII), specific examples of the aromatic ring and the heterocyclic ring, the substituent of the aromatic ring and the heterocyclic ring, the alkyl group having 1 to 8 carbon atoms, the halogen atom, the alkyl group having 1 to 20 carbon atoms, the aryl group having 6 to 30 carbon atoms, and the arylalkyl group having 7 to 30 carbon atoms include, but are not particularly limited to, those described in the above general formulas (I) and (II). In addition, in the above formulas (IV) to (VII), the anchor group means a substituent that has chemical or electrostatic affinity or bonding ability to a metal oxide layer (support) comprising a metal oxide, and specifically, specific examples thereof include a carboxylic acid group, a sulfonic acid group, and a phosphoric acid group.

In the above general formulas (I) to (III), $Z^1$ is not particularly limited as long as it is any one of —CONR—, —NRCO—, —SO$_2$NR—, and —NRSO$_2$—. In terms of further enhancing energy conversion efficiency, $Z^1$ is preferably —CONR— or —NRCO—. In addition, in the above general formulas (I) to (II), it is preferable that m is 0 and n is 2, in terms of further enhancing energy conversion efficiency and durability. When the anchor group (substituent —$Y^2$—COOH) is formed only on the cyanine skeleton side in this manner, the dye is adsorbed with the cyanine skeleton side oriented to a metal oxide layer surface. Therefore, energy transfer from the second light absorption site to the first light absorption site is efficiently performed, and as a result, light energy absorbed by the first light absorption site and light energy absorbed by the second light absorption site are both transferred to the metal oxide semiconductor with high efficiency. In addition, the adsorption state of the dye is relatively bulky, and further, the anchor group (substituent —$Y^2$—COOH) adsorbed on the metal oxide layer is relatively hydrophobically protected by the steric hindrance of the dye itself. Therefore, the peeling properties of the dye with respect to water are enhanced, and as a result, the durability is further enhanced.

The linking sites of the above $Z^1$ to the above A and B are not particularly limited. Specific examples of preferable linking structures of A and $Z^1$, and preferable linking structures of B and $Z^1$ are illustrated below.

[Formula 35]

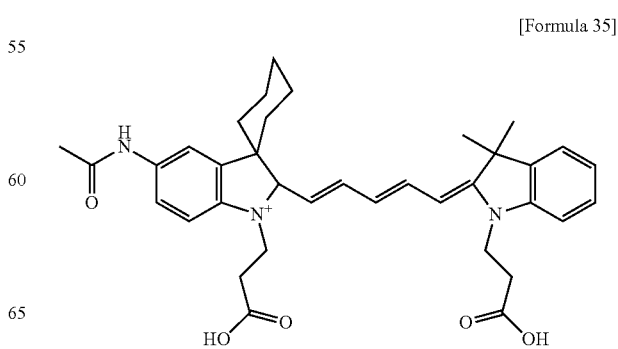

23
-continued
24
-continued
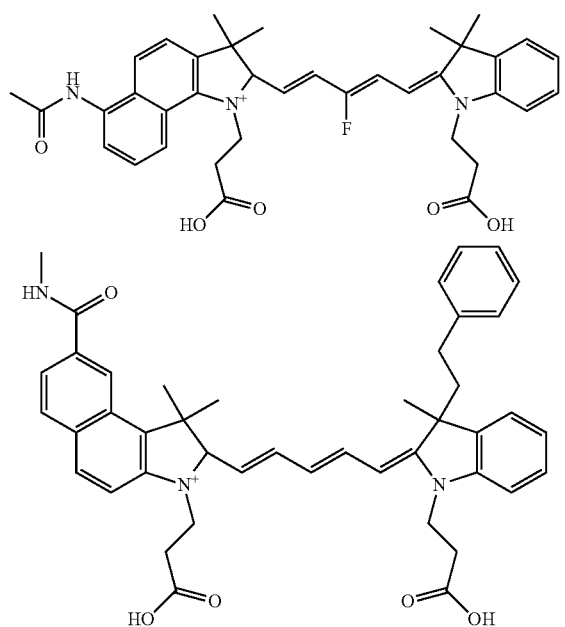
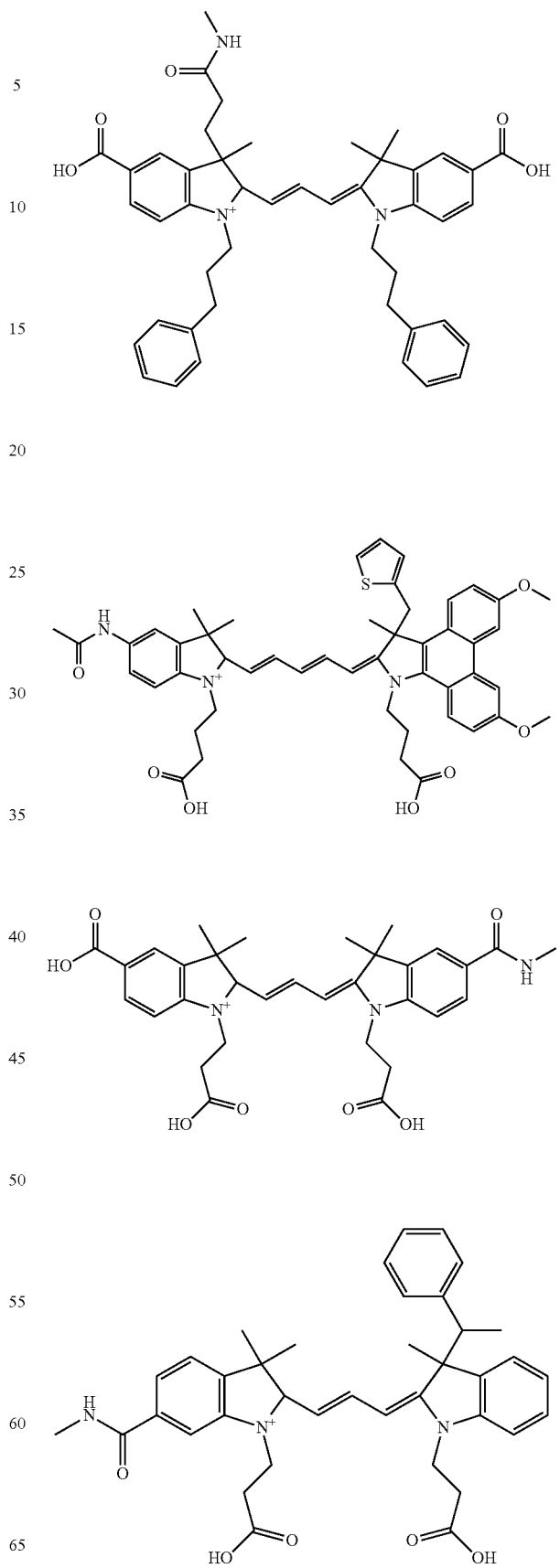

25
-continued
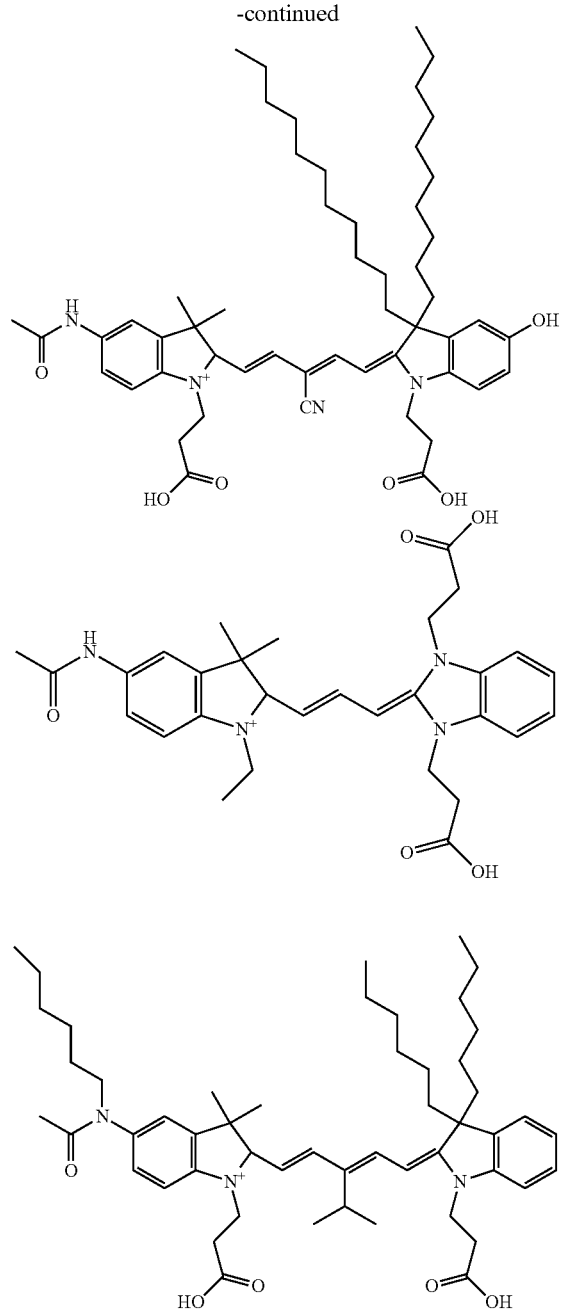
26
-continued
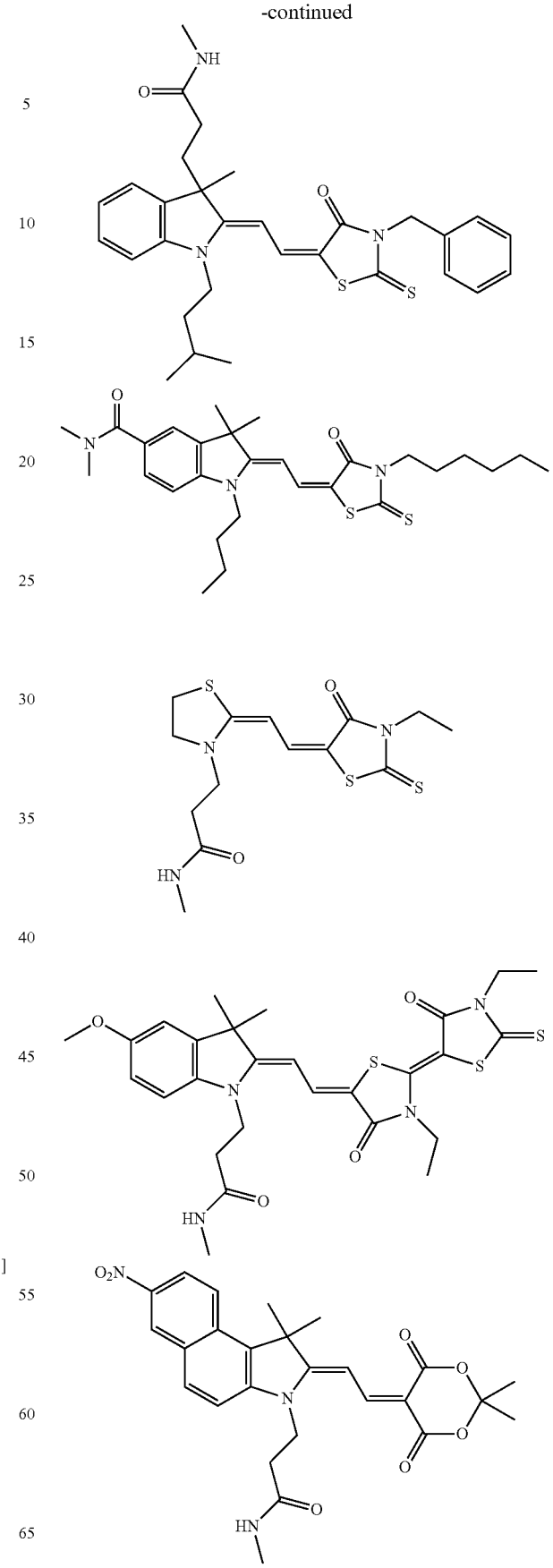
[Formula 36]

27
-continued
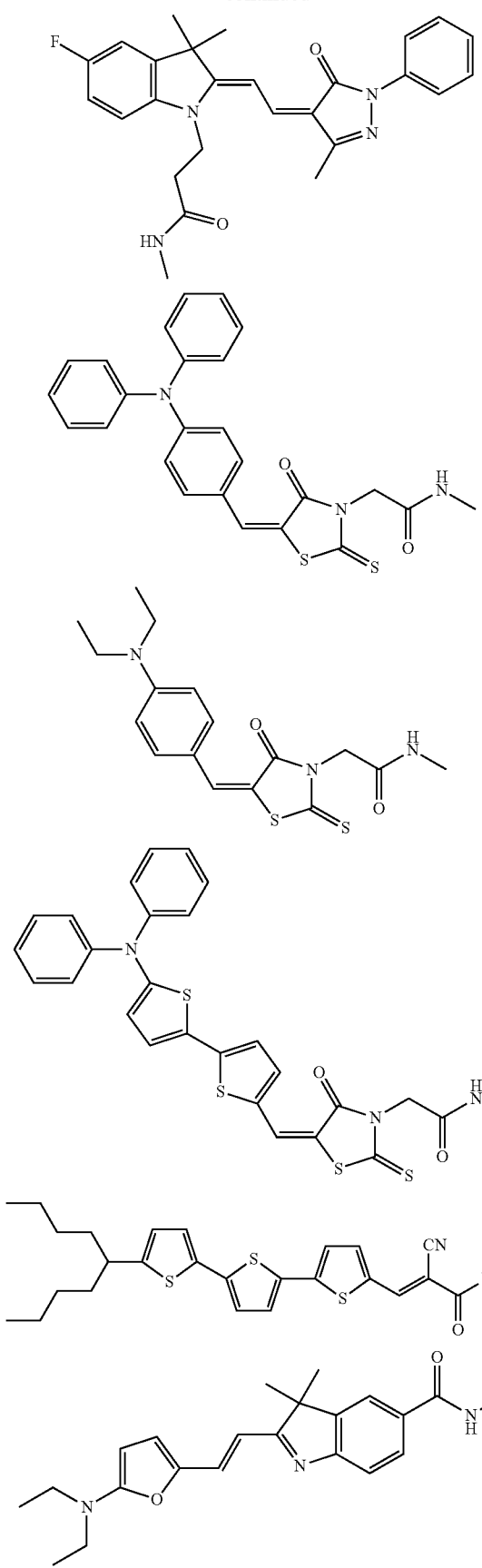
28
-continued
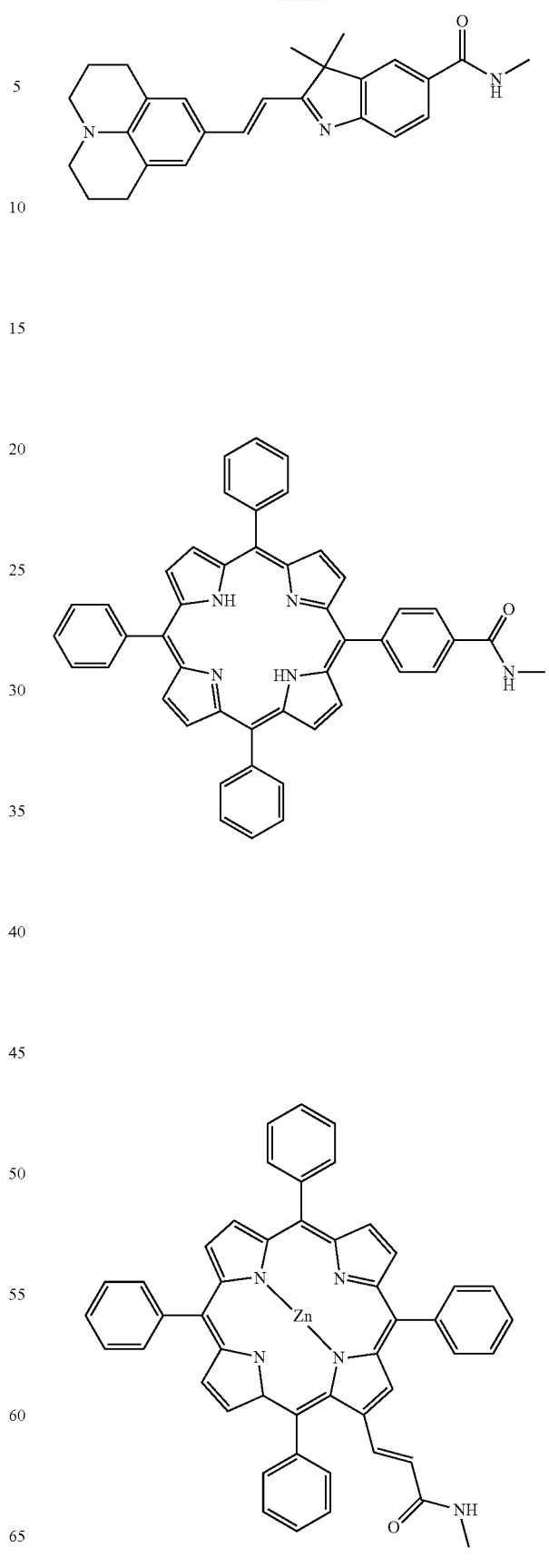

| 29 | 30 |
|---|---|
| -continued | -continued |
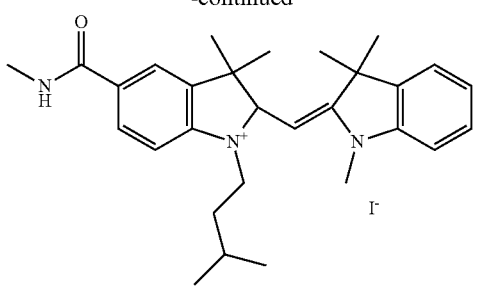
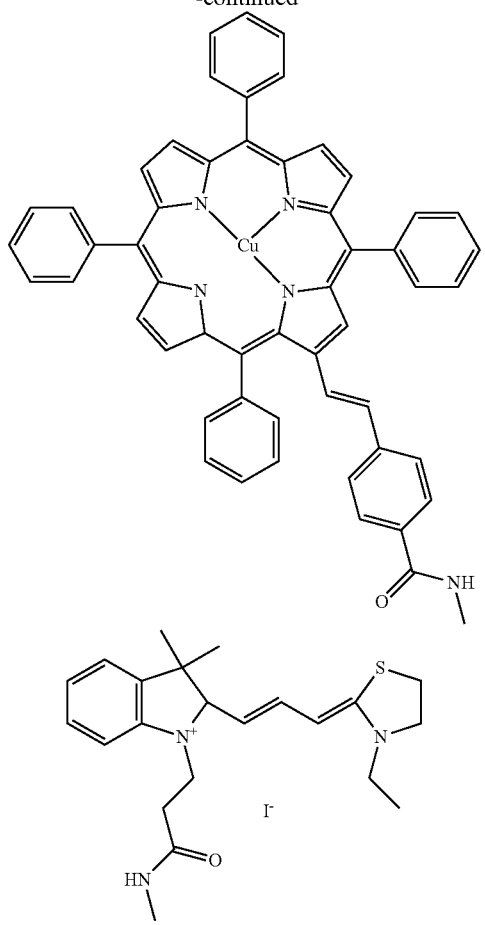
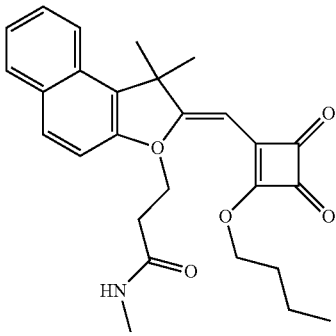
[Formula 37]
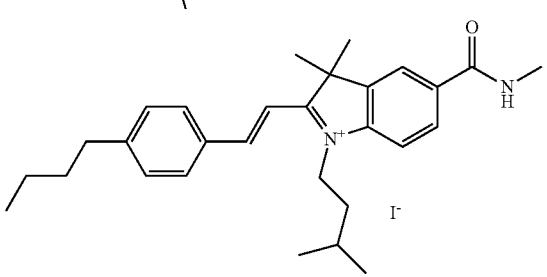
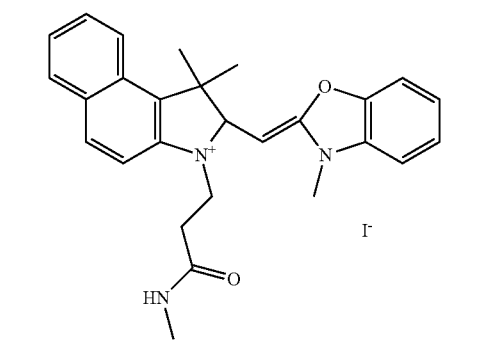
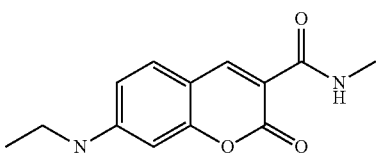
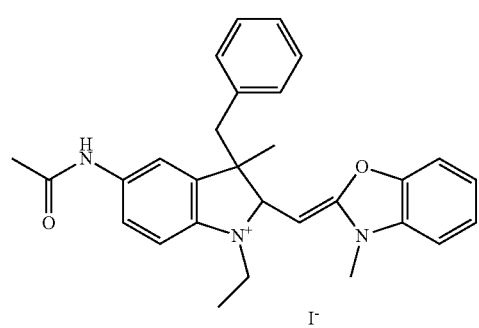
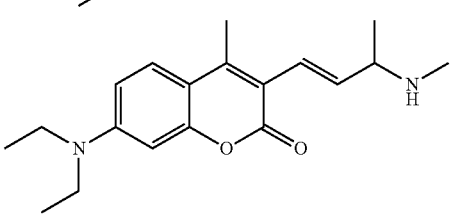

-continued

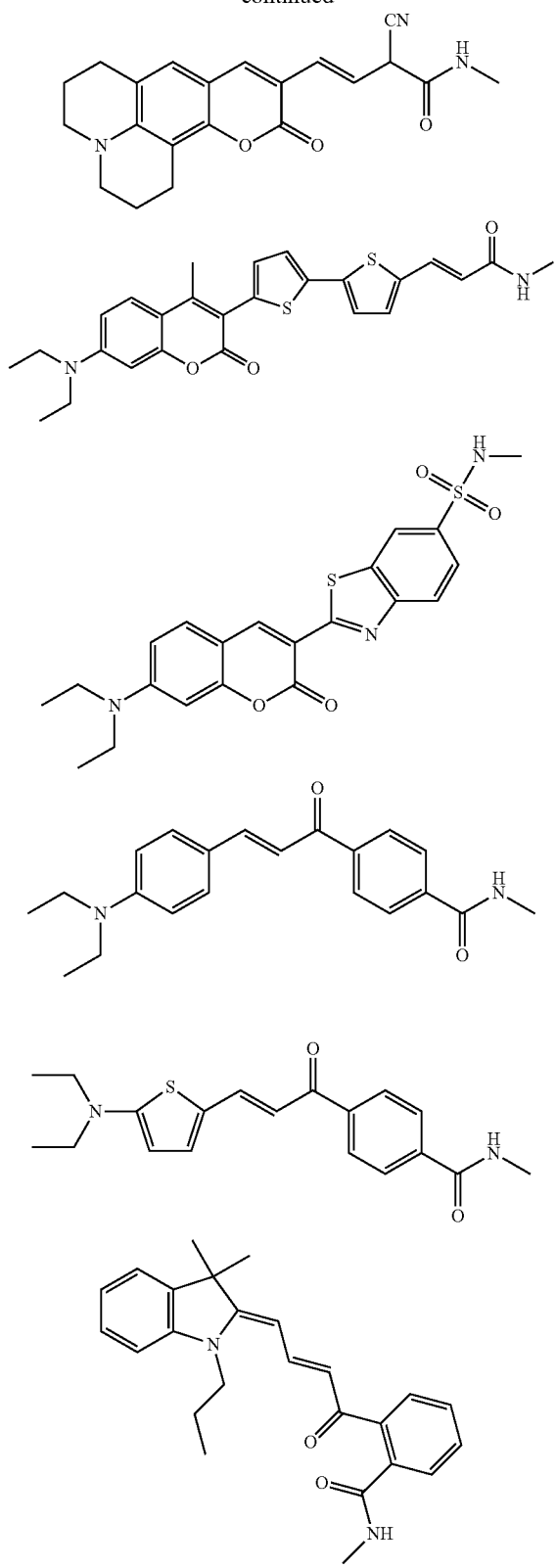

In this embodiment, a further preferable dye has a structure represented by the following general formula (VIII), and a particularly preferable dye has a structure represented by the following general formula (IX).

[Formula 38]

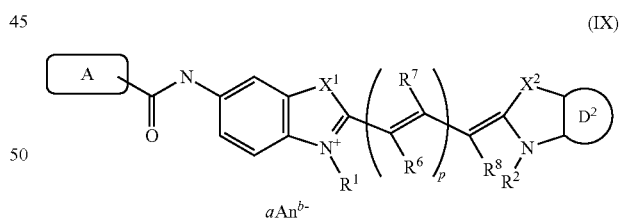

(VIII)

wherein A is a structure having a maximum absorption wavelength λmax of 350 to 500 nm in a methanol solution; $Z^1$ is any one divalent linking group selected from —CONR—, —NRCO—, —SO$_2$NR—, and —NRSO$_2$—; R in $Z^1$ is a hydrogen atom, an alkyl group having 1 to 8 carbon atoms, or an arylalkyl group having 7 to 20 carbon atoms; $X^1$ and $X^2$ are each independently an oxygen atom, a sulfur atom, a selenium atom, $CR^3R^4$, or $NR^5$, and may be the same or different; $D^2$ is a benzene ring which may have a substituent, a naphthalene ring which may have a substituent, or a phenanthrene ring which may have a substituent; $R^1$ to $R^2$ are each independently —$Y^2$—COOH, a hydrogen atom, an alkyl group having 1 to 20 carbon atoms, an alkenyl group having 2 to 8 carbon atoms, or an alkynyl group having 2 to 8 carbon atoms, where at least one of $R^1$ to $R^2$ is —$Y^2$—COOH, and $Y^2$ is each independently an alkylene group having 1 to 8 carbon atoms, or a single bond; $R^3$ to $R^5$ are each independently a hydrogen atom, an alkyl group having 1 to 20 carbon atoms, an alkenyl group having 2 to 8 carbon atoms, or an alkynyl group having 2 to 8 carbon atoms, and may be the same or different; $R^6$ to $R^8$ are each independently a hydrogen atom, an alkyl group having 1 to 8 carbon atoms, an aryl group having 6 to 12 carbon atoms, a halogen atom, or a cyano group, and may be the same or different; p is 1 or 2; $An^{b-}$ is a b-valent anion; a is 1 or 2, and is a coefficient for keeping the charge of the entire dye neutral; and b is 1 or 2.

[Formula 39]

(IX)

wherein symbols are similar to those described in the above general formula (VIII).

In the dye having the structure represented by the above general formula (VIII), the structure having a maximum absorption wavelength λmax of 350 to 500 nm in a methanol solution (second light absorption site) and the cyanine skeleton (first light absorption site) are linked by the linking group with high efficiency energy transfer, and in the dye having the structure represented by the above general formula (IX), they are linked by a particularly excellent amide bond. Moreover, the anchor group (substituent —$Y^2$—COOH) is formed only on the cyanine skeleton side. Therefore, the energy conversion efficiency and the durability are particularly excellent.

In the above general formula (VIII), specific examples of A, $X^1$, $X^2$, $Y^2$, $D^2$, $R^1$ to $R^8$, p, $An^{b-}$, a, and b are similar to those described above.
Specific examples (1) to (57) of the dye in this embodiment are listed below, but are not particularly limited to these.
[Formula 40]
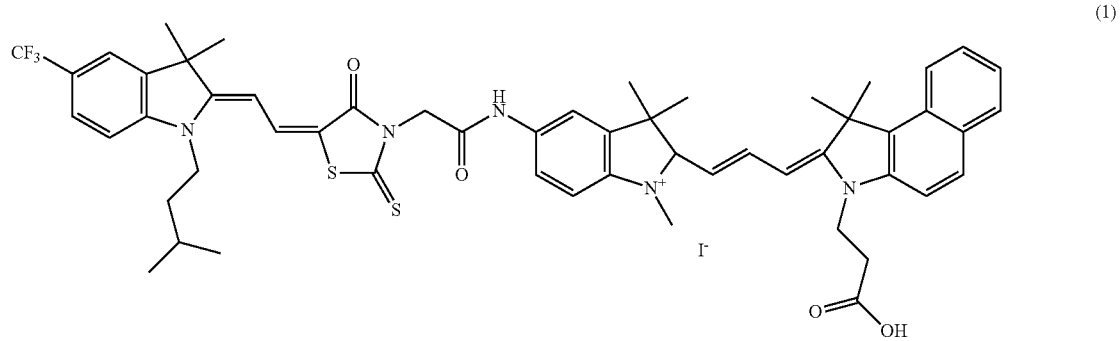
(1)
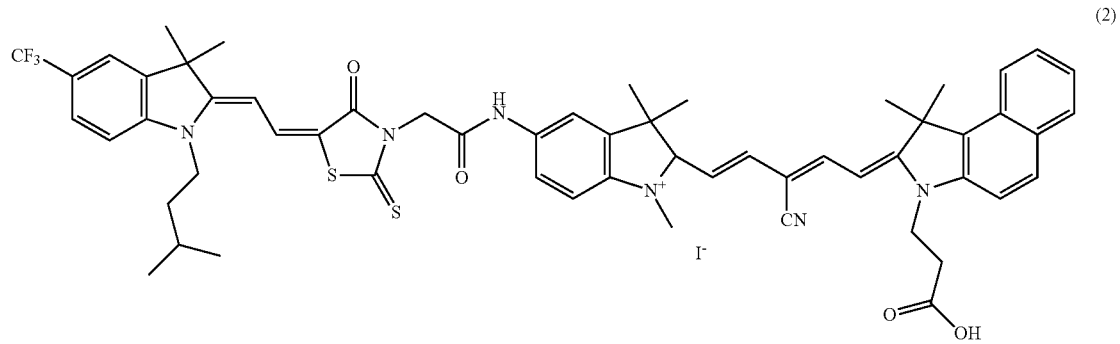
(2)
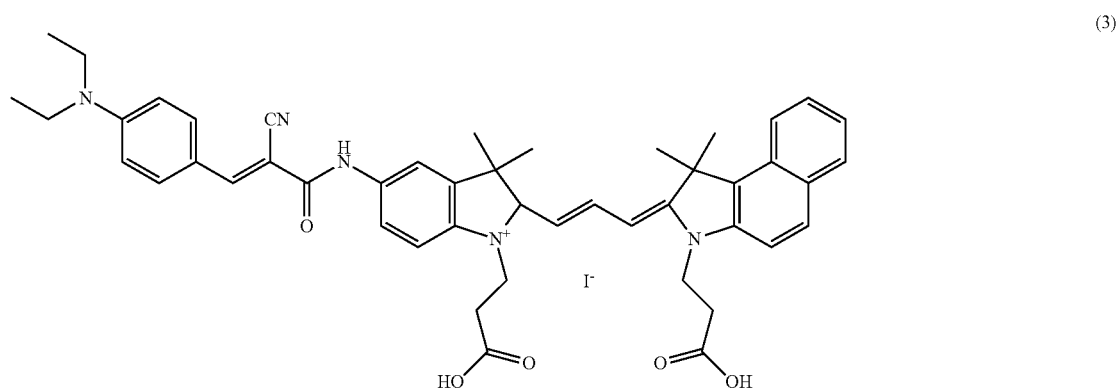
(3)
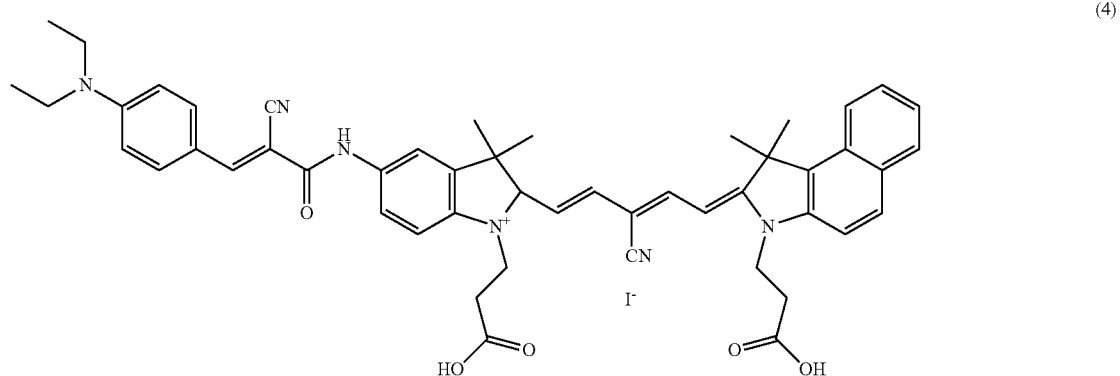
(4)

-continued
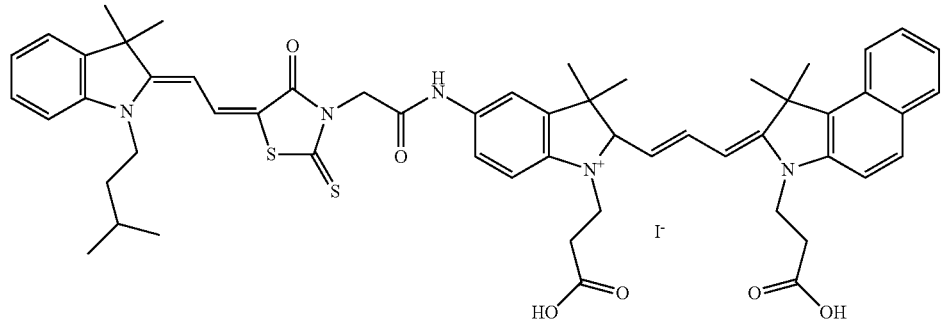
(5)
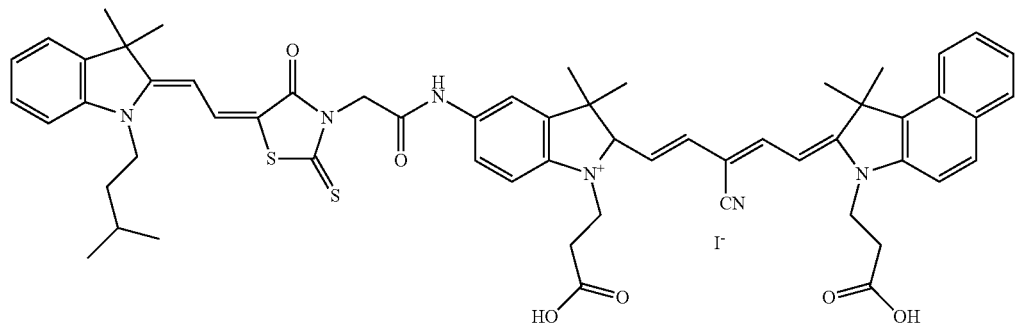
(6)
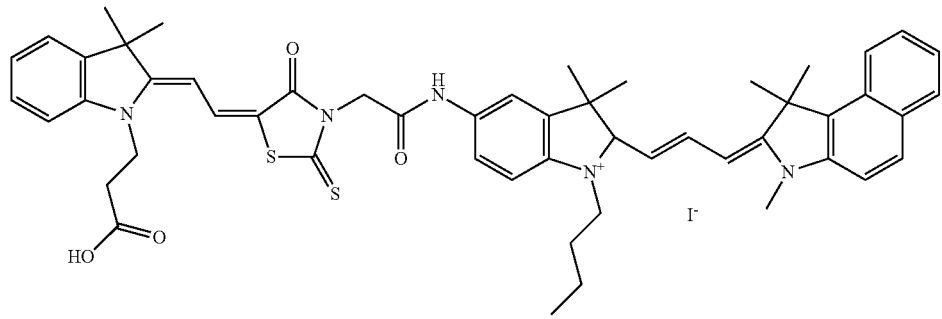
(7)
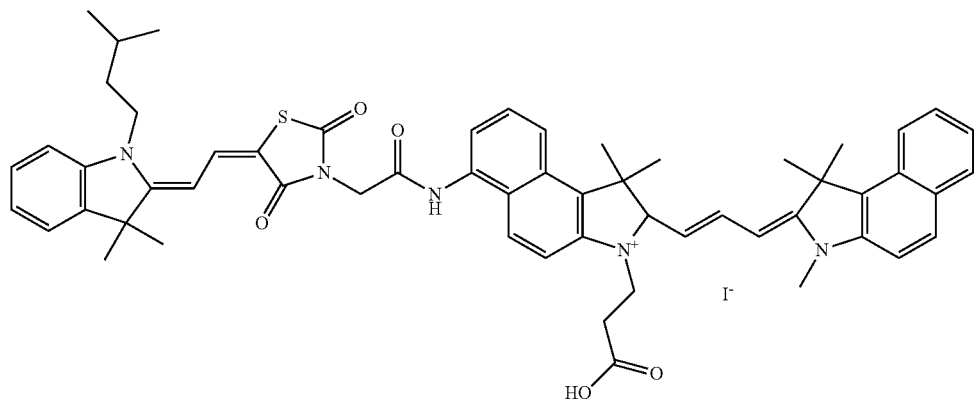
(8)

(9)
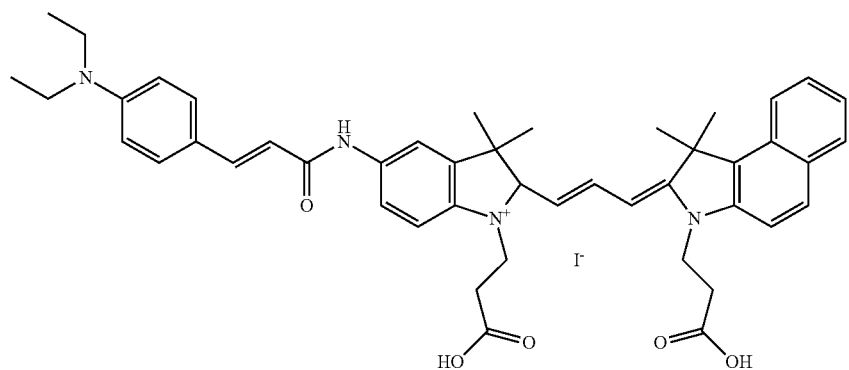
(10)
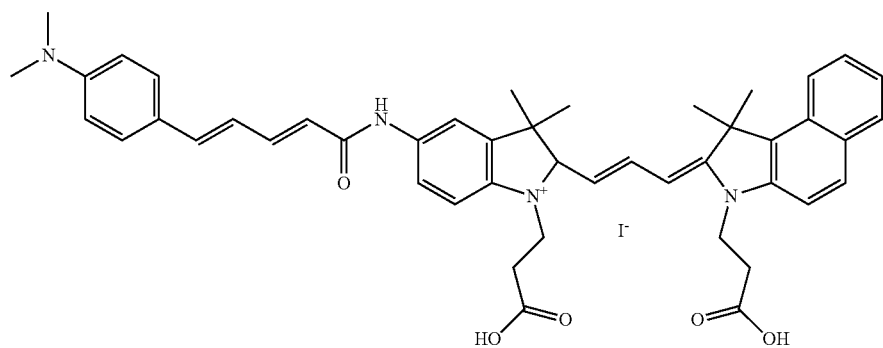
(11)
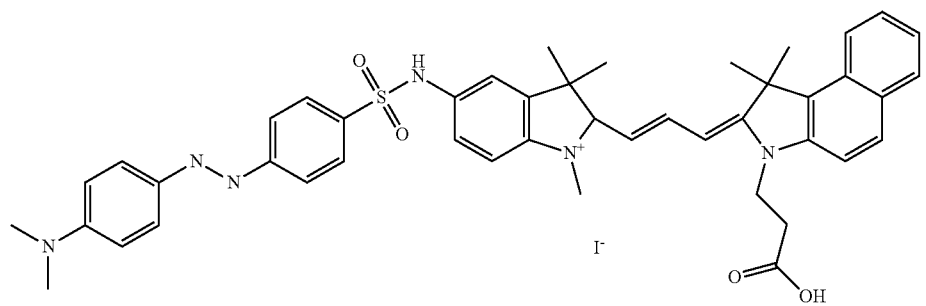

-continued
(12)
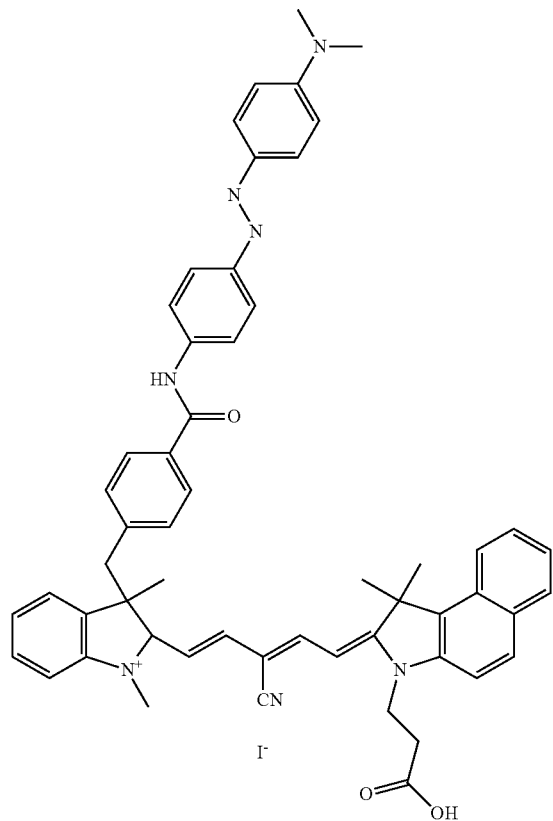
(13)
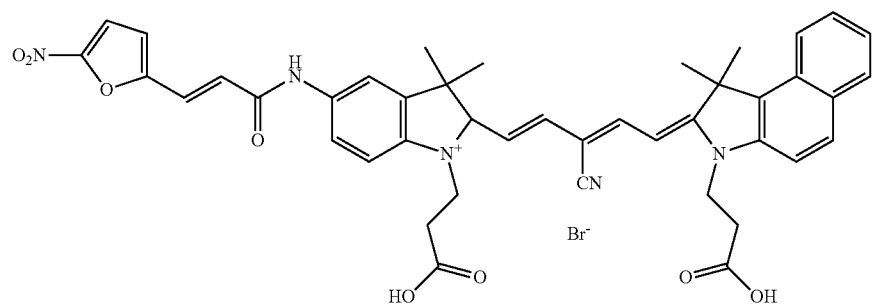
[Formula 41]
(14)
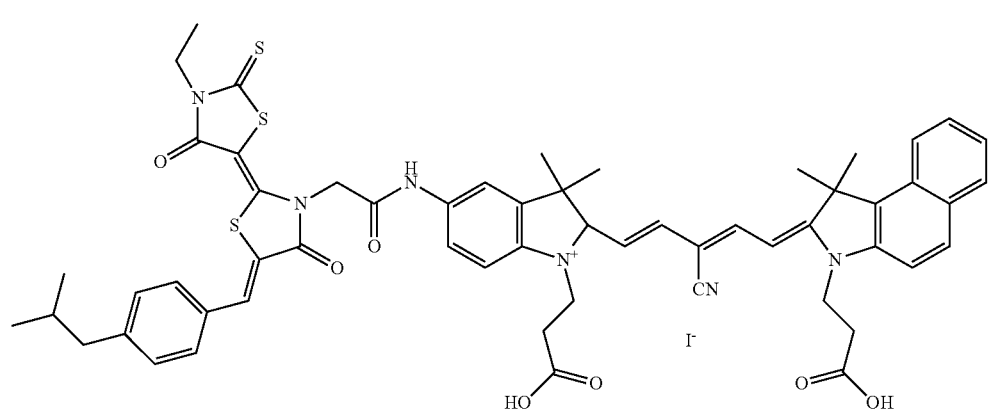

-continued
(15)
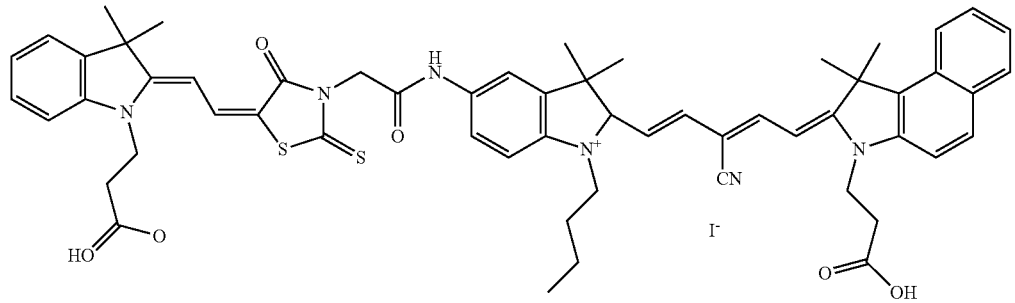
(16)
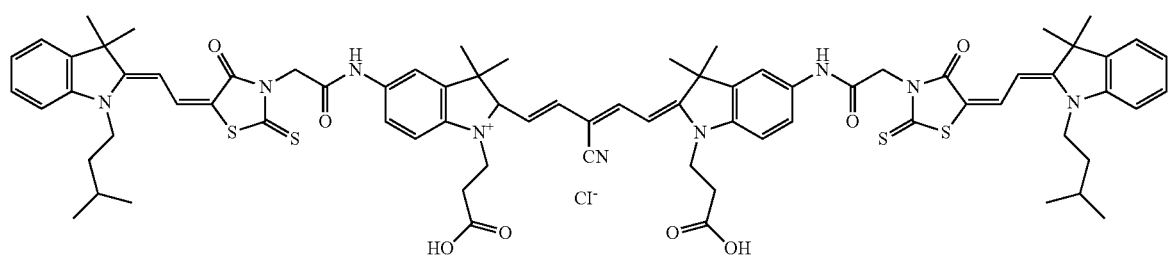
(17)
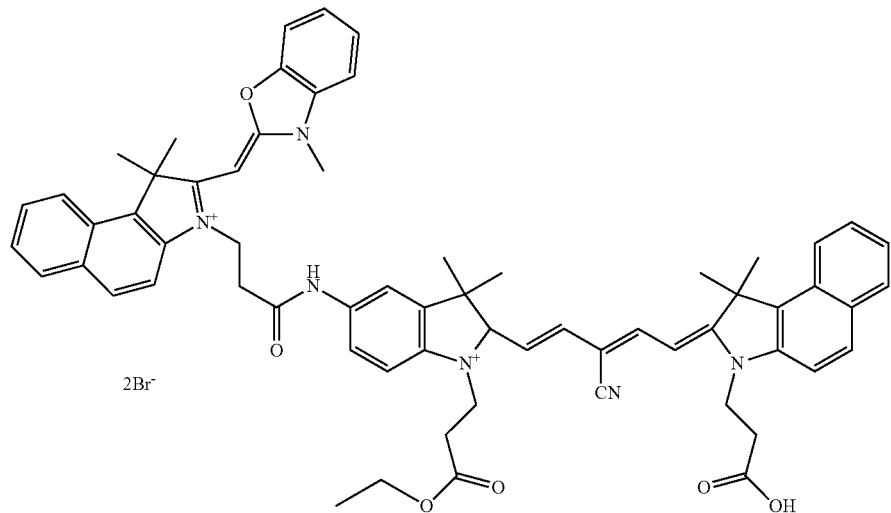
[Formula 42]
(18)
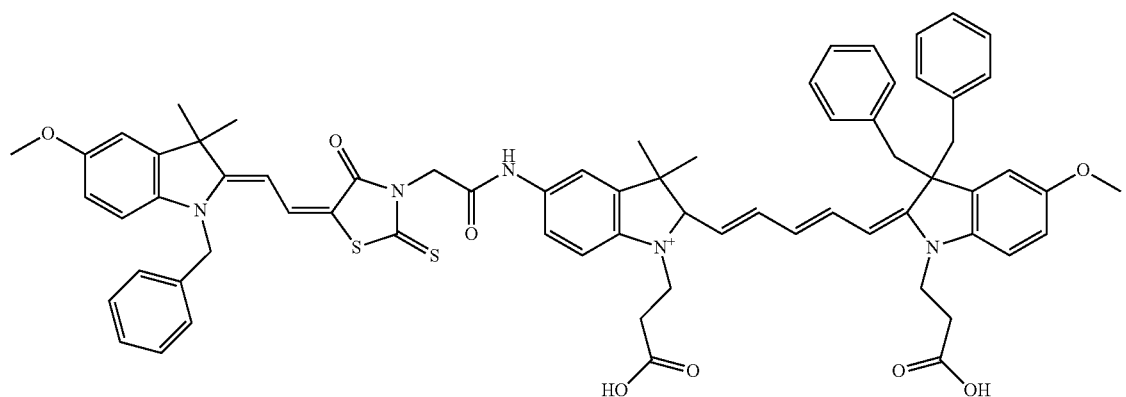

(19)
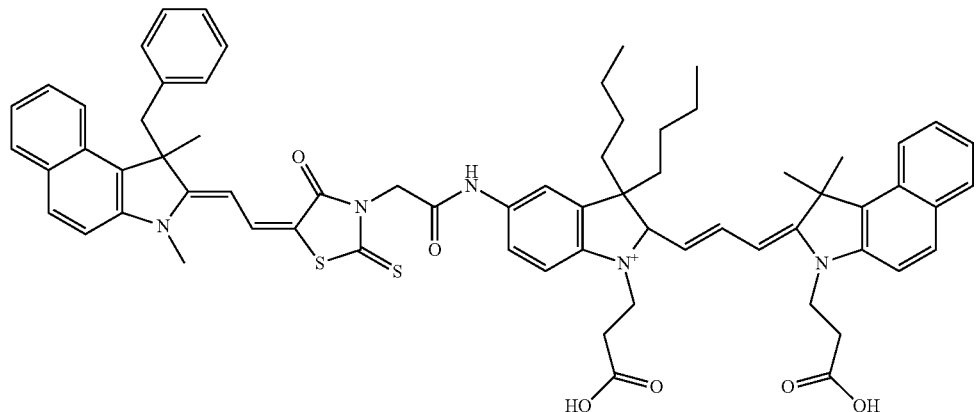
(20)
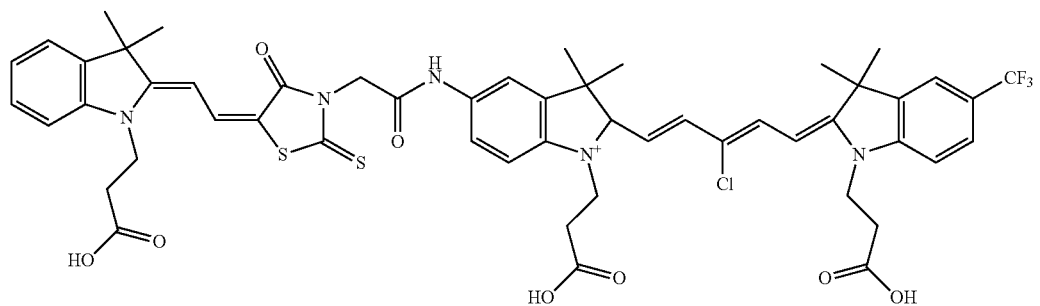
(21)
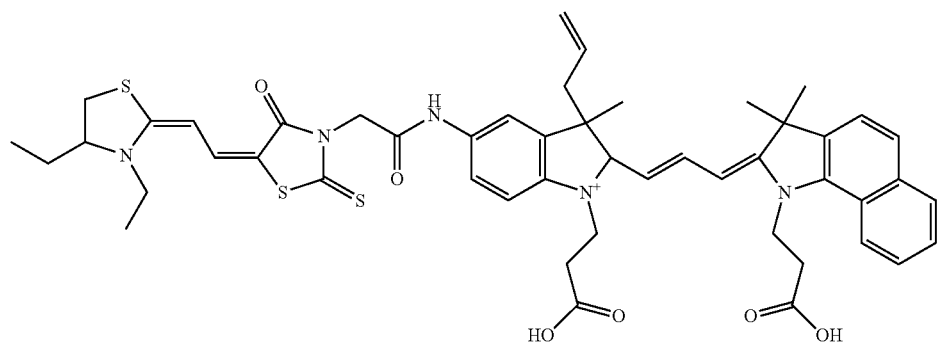
(22)
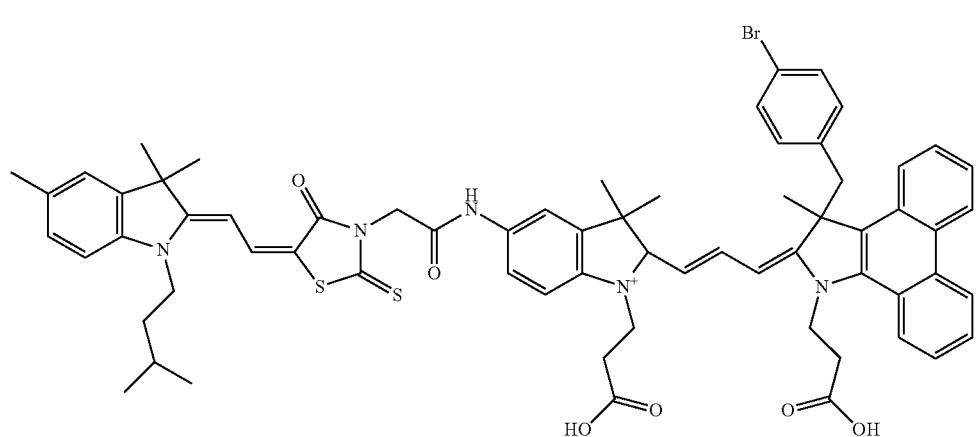

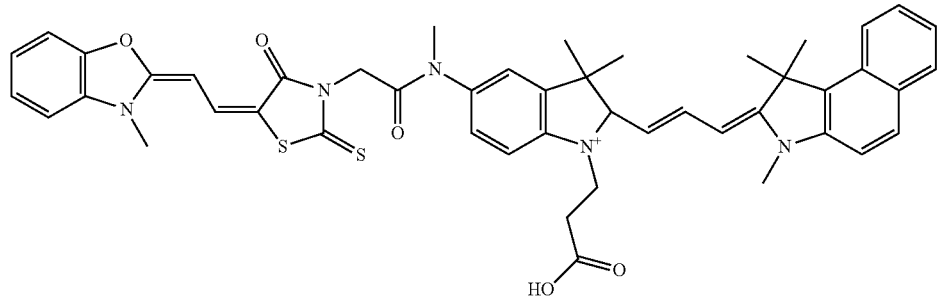
(23)
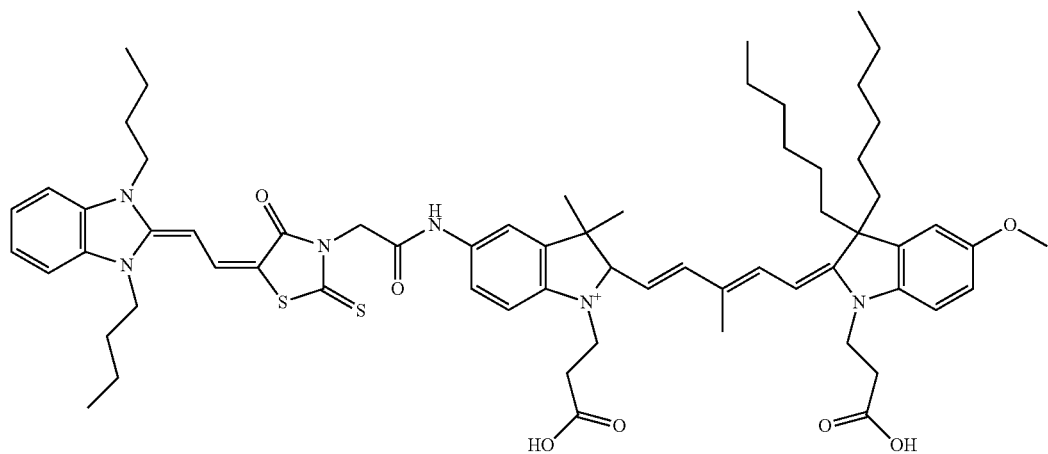
(24)
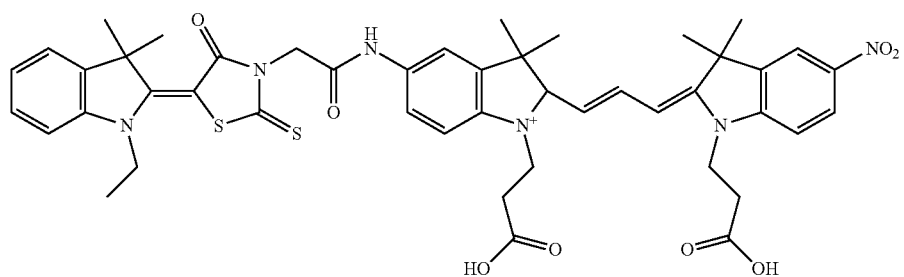
(25)
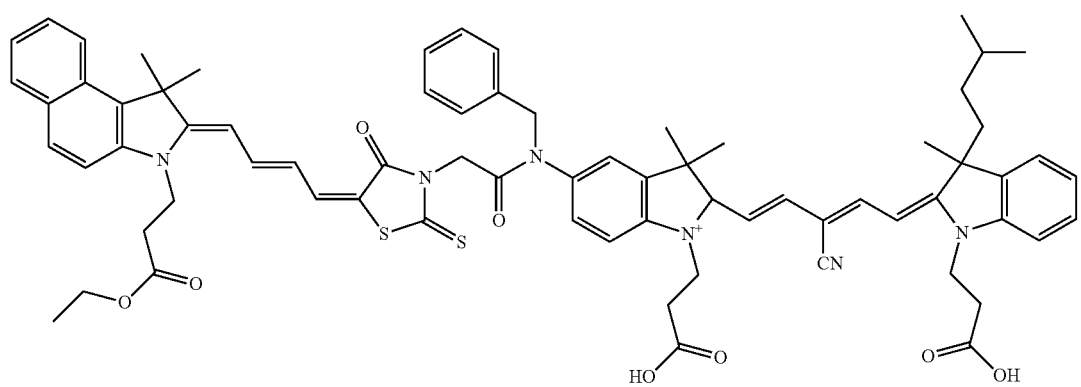
(26)

(27)
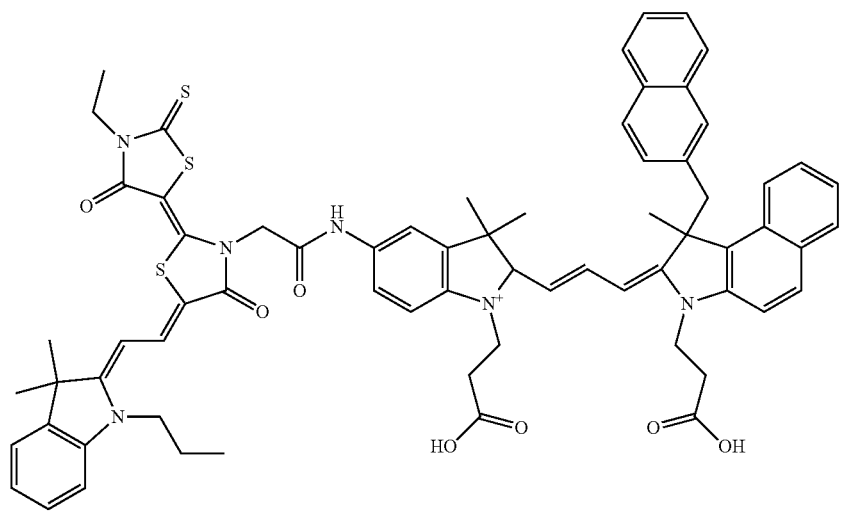
(28)
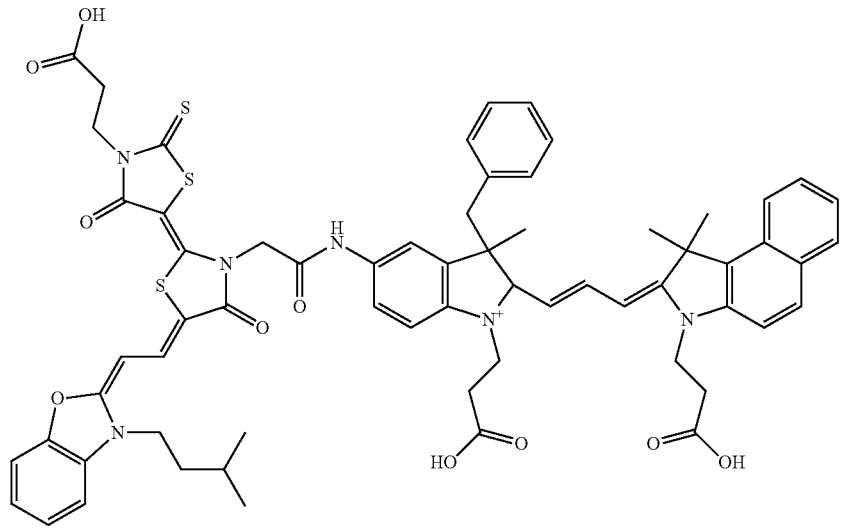
(29)
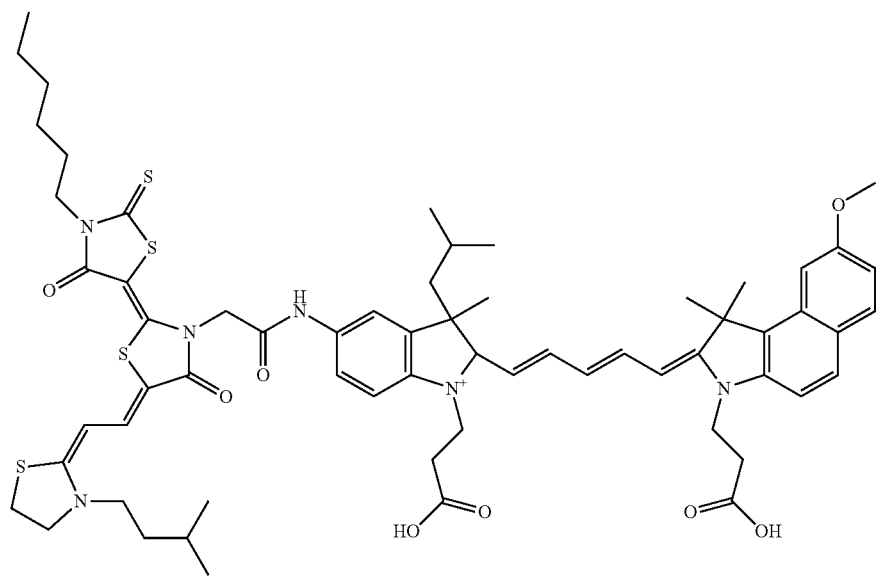

[Formula 43]
(30)
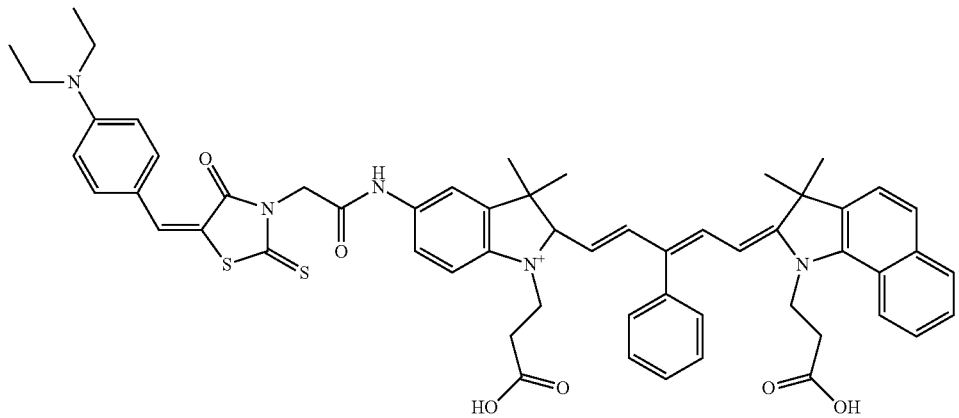
(31)
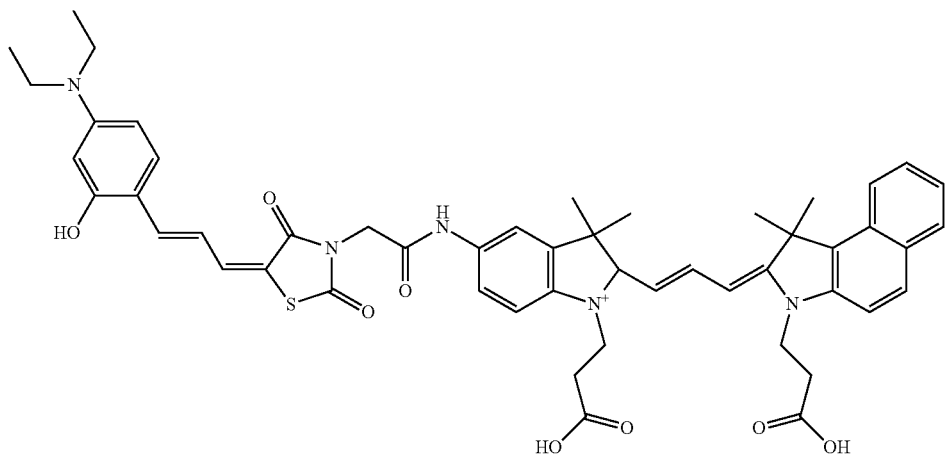
(32)
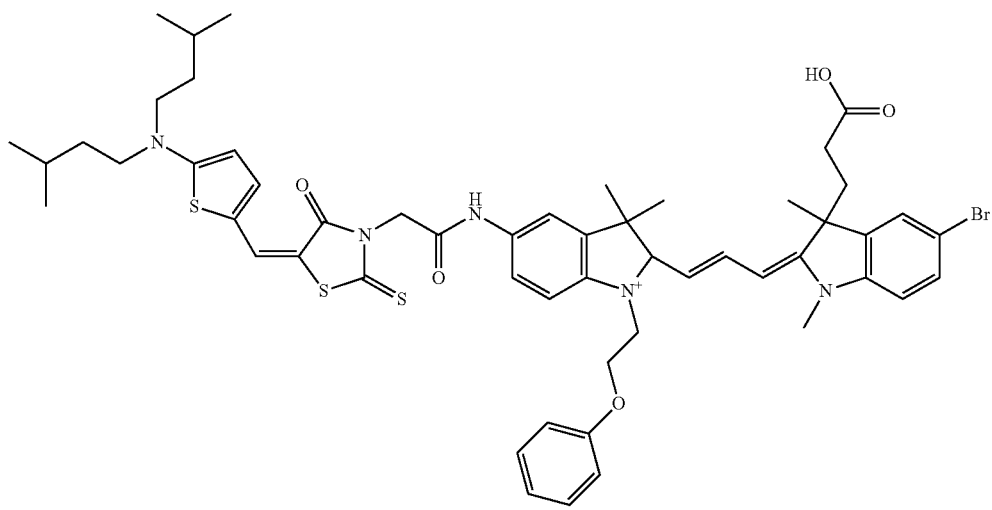

-continued
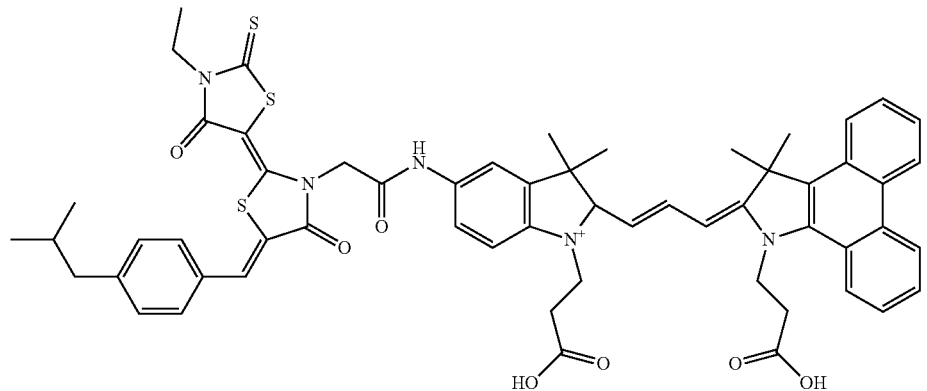
(33)
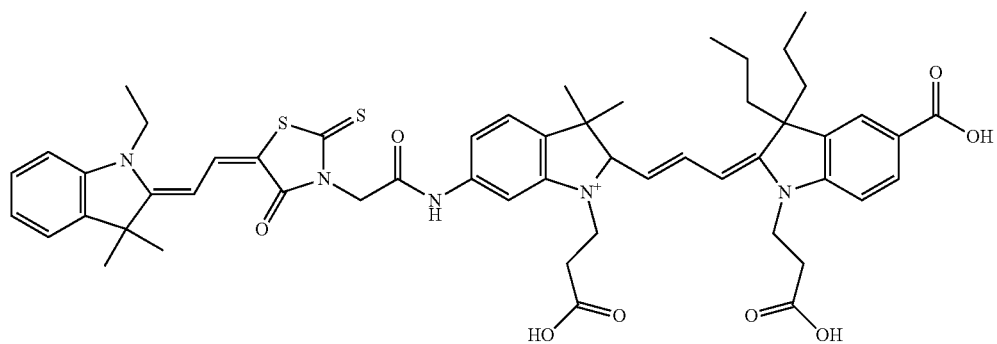
(34)
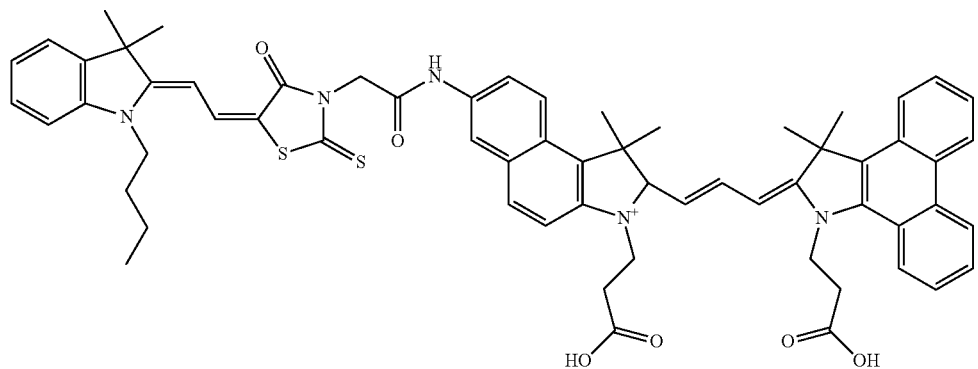
(35)
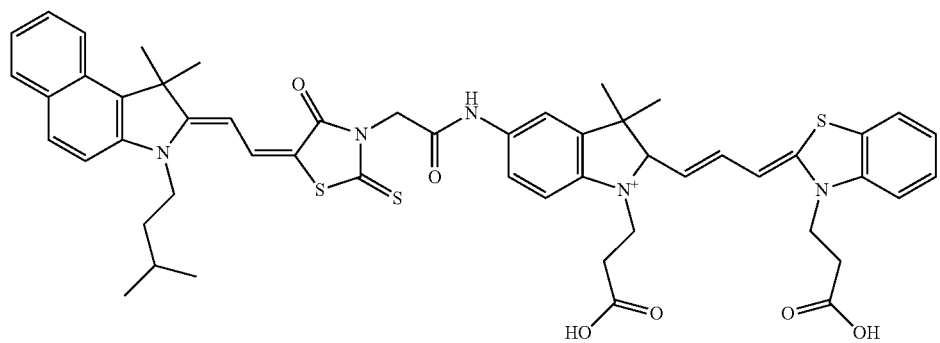
(36)

-continued
(37)
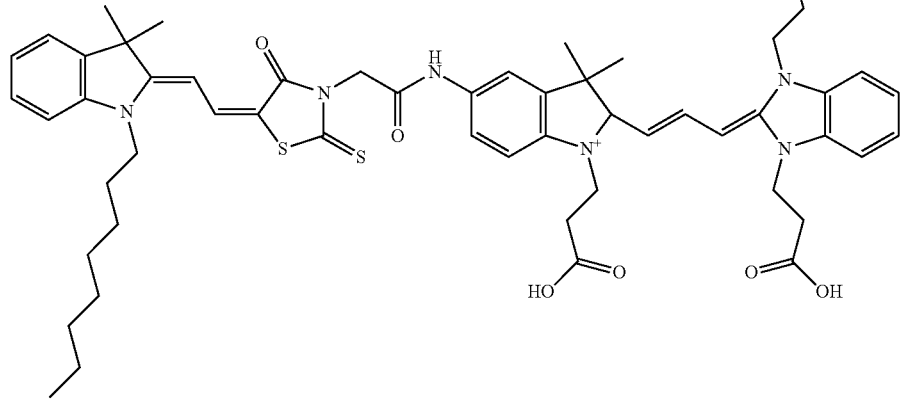
(38)
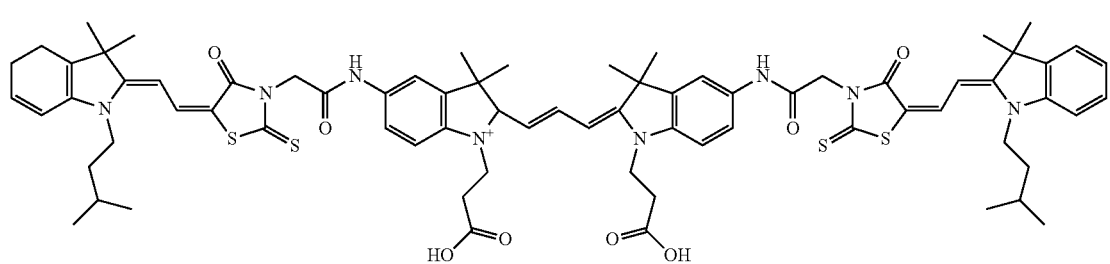
(39)
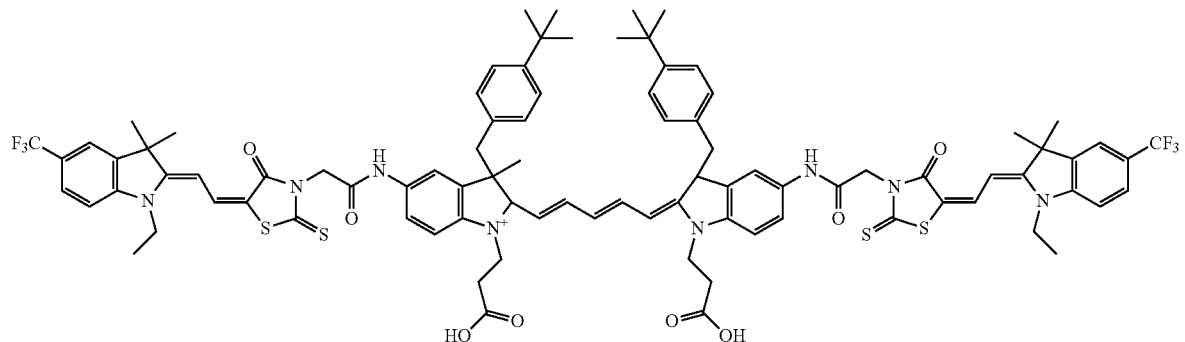
[Formula 44]
(40)
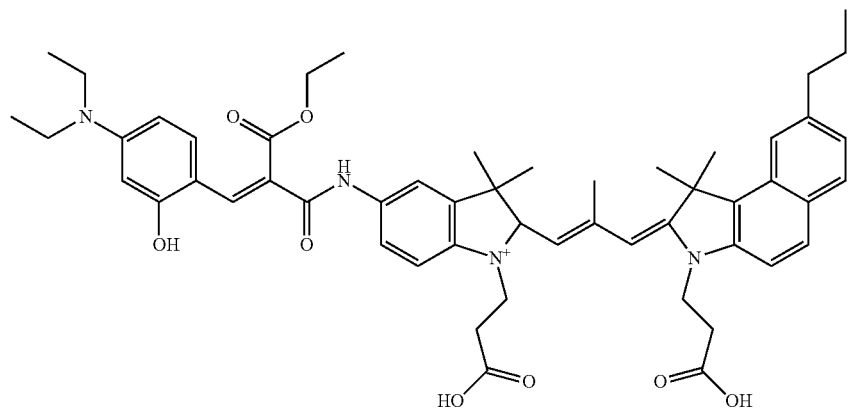

-continued
(41)
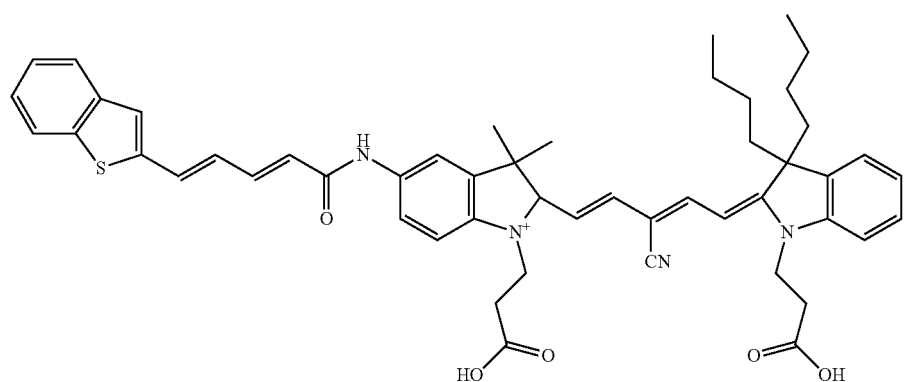
(42)
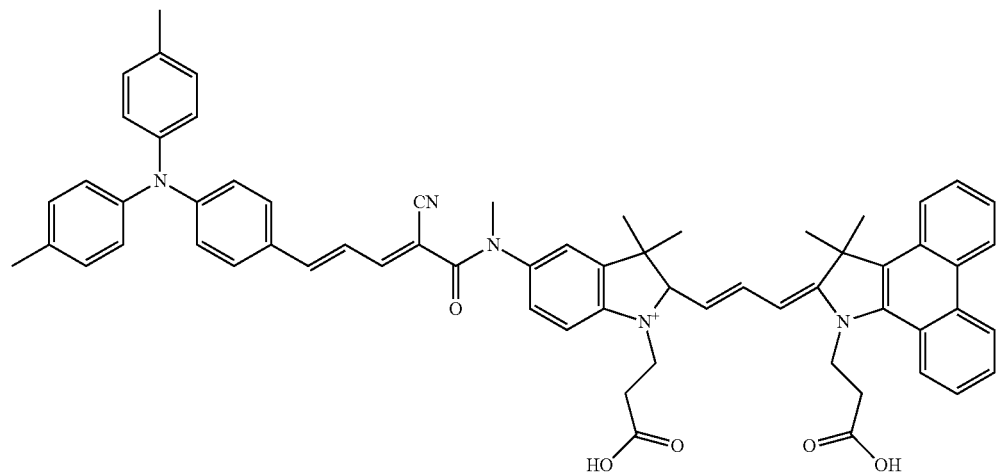
(43)
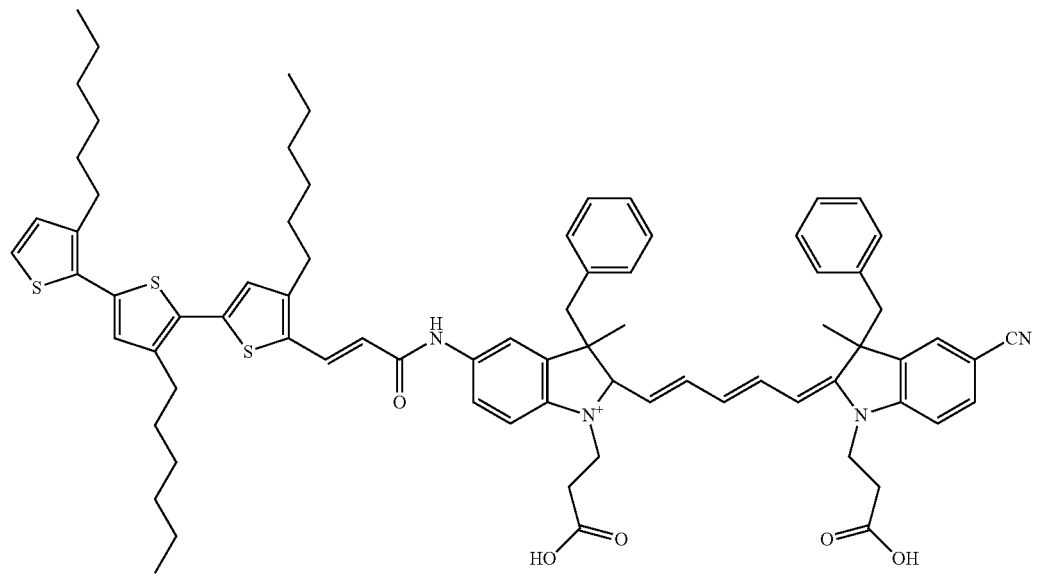

(44)
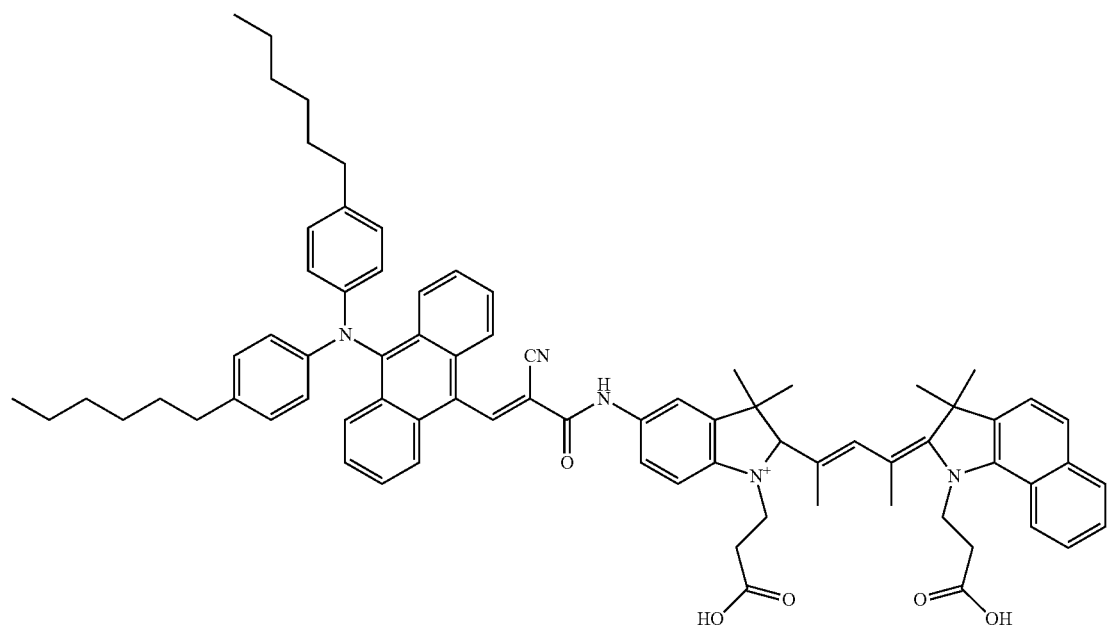
(45)
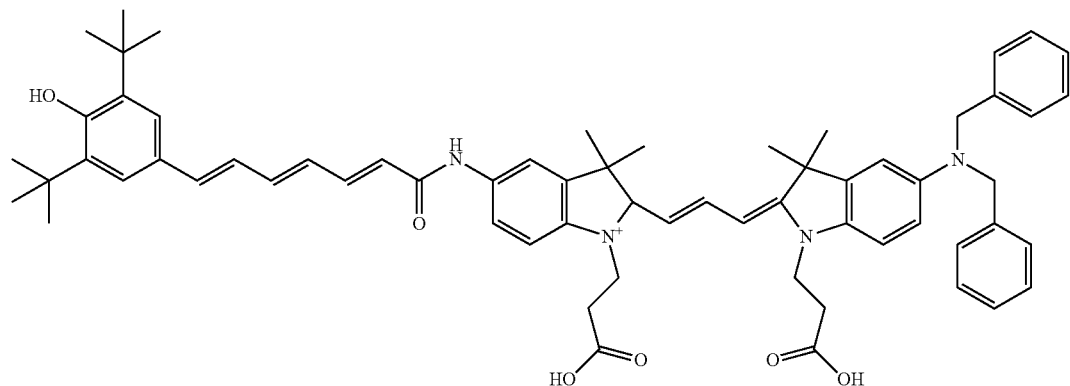
(46)
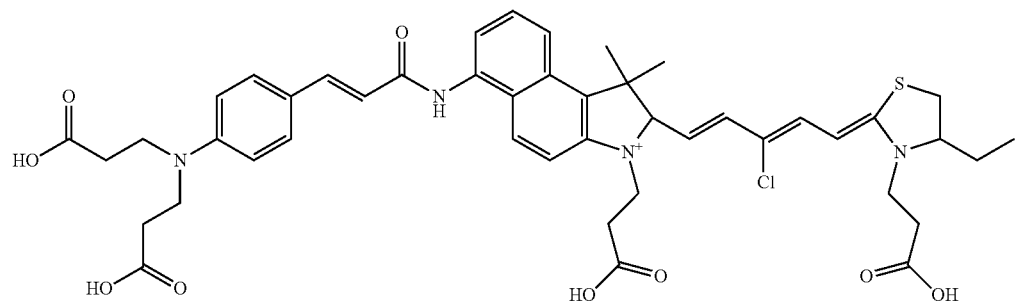
(47)
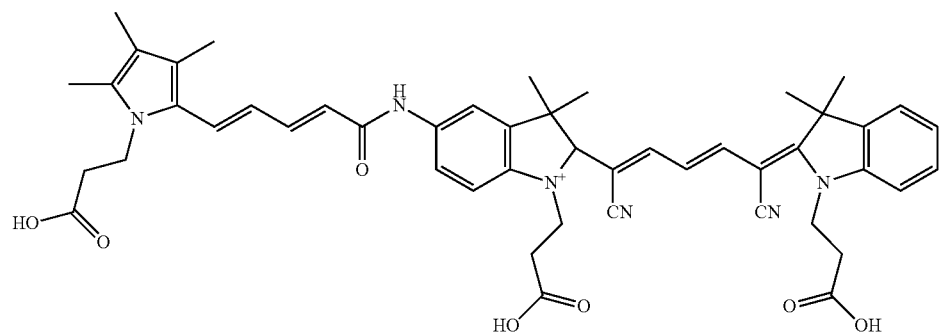

-continued
(48)
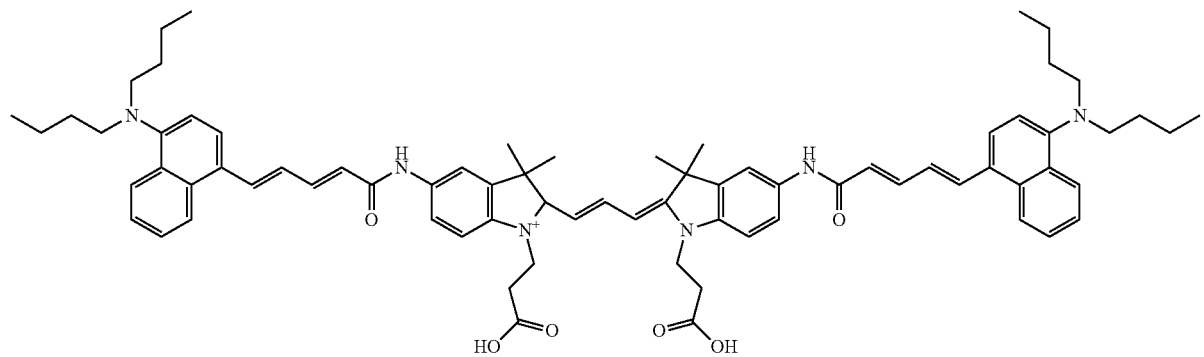
(49)
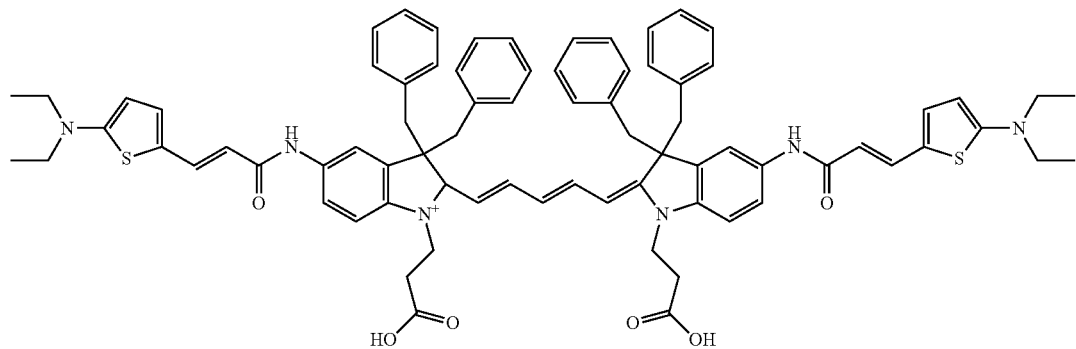
[Formula 45]
(50)
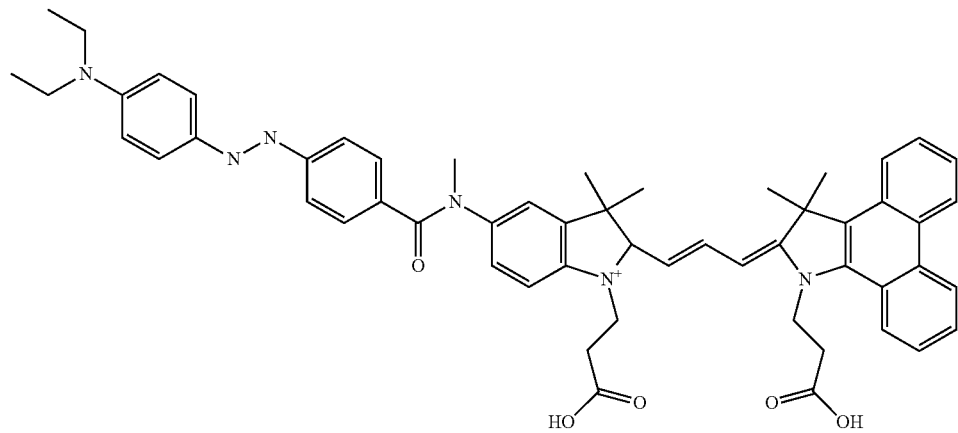
(51)
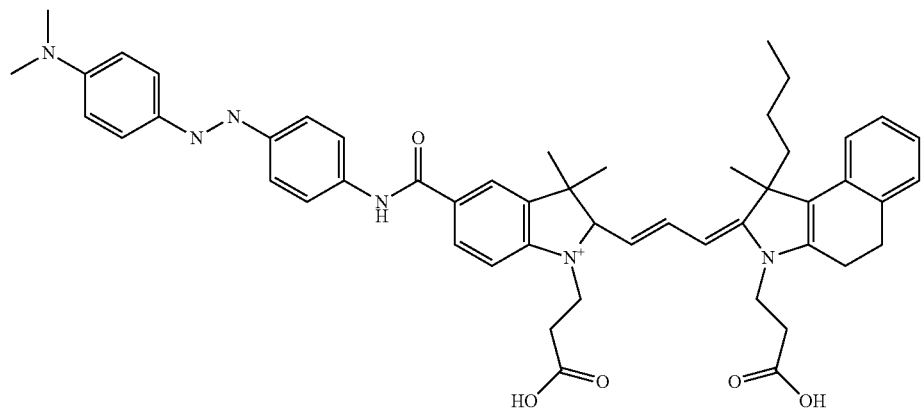

-continued
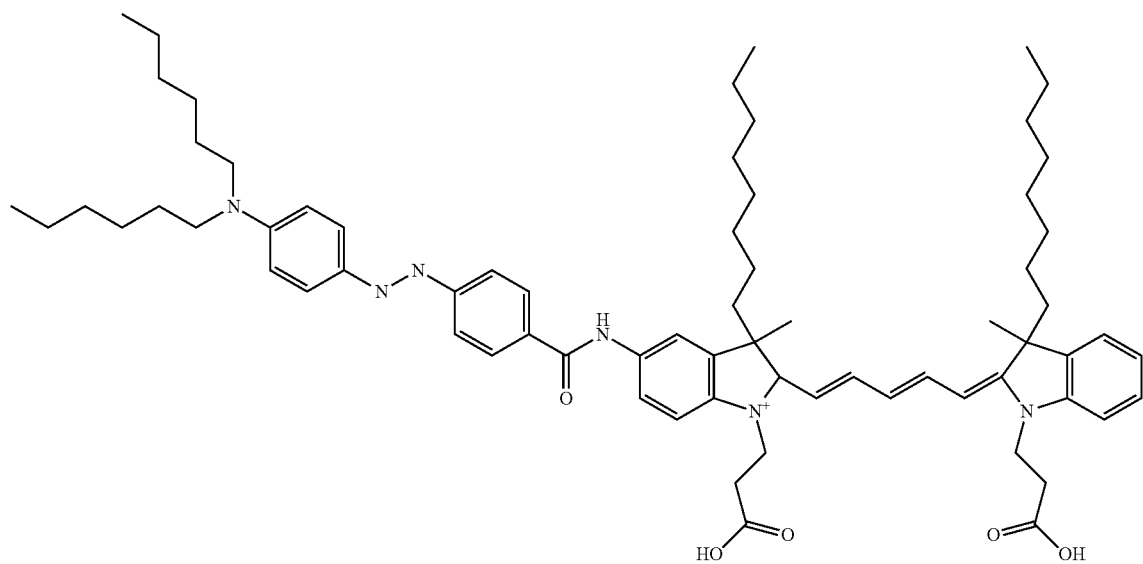
(52)
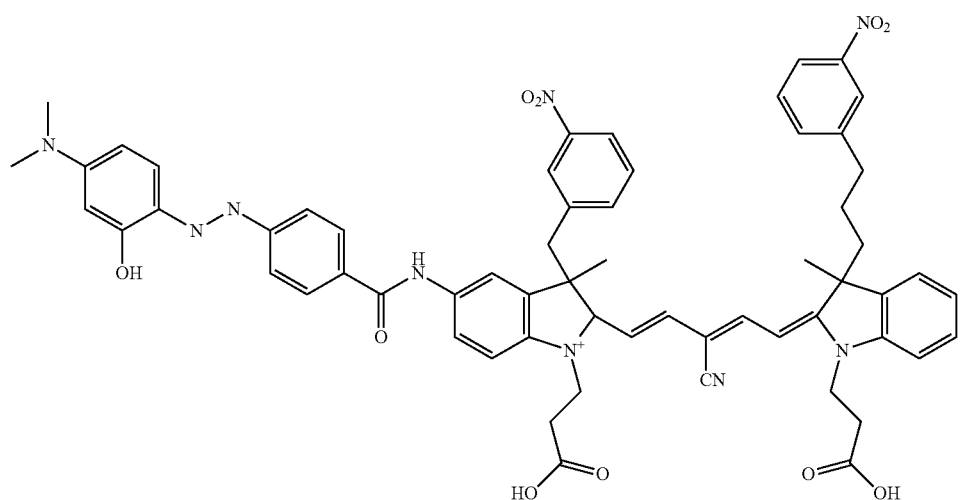
(53)
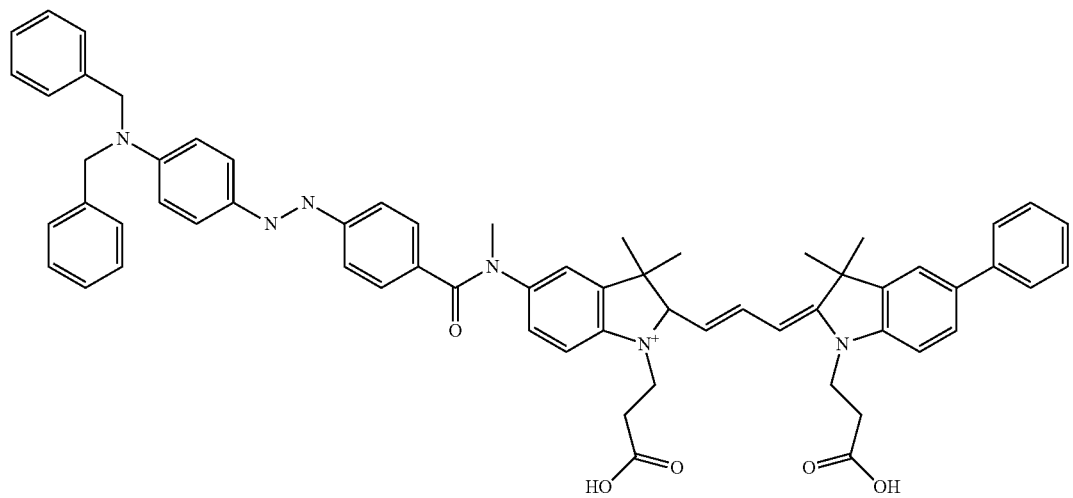
(54)

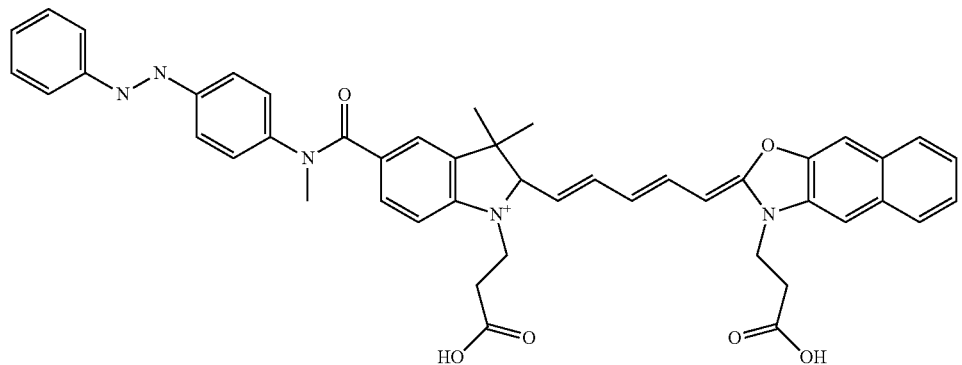

(55)

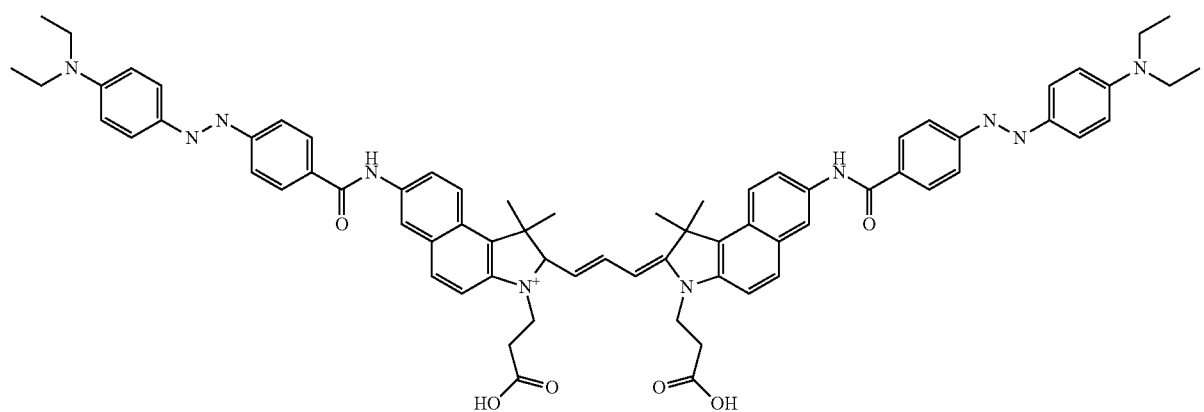

(56)

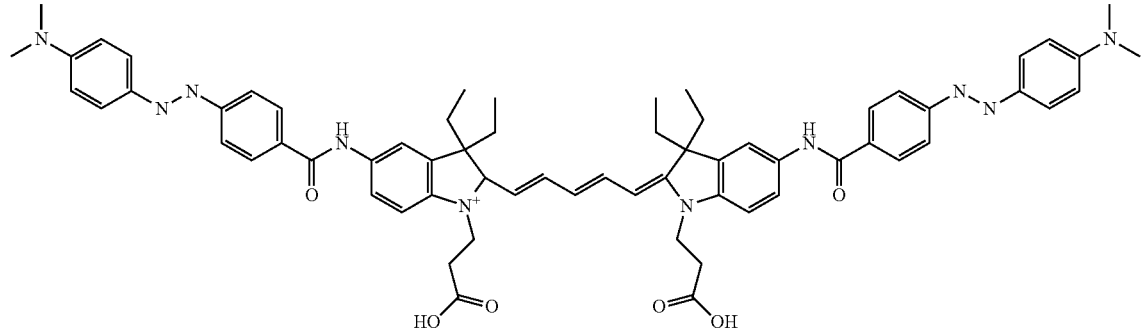

(57)

As long as the dye in this embodiment has the structure represented by the above general formula (I), more preferably the structure represented by the above general formula (II) or (III), and further preferably the structure represented by the above general formula (VIII), other structures are not particularly limited. In addition, as long as the dye in this embodiment has these structures, even in an enantiomer or diastereoisomer thereof or a mixture thereof, similar effects are obtained.

The dye in this embodiment can be obtained by a method using a publicly known or well-known general reaction, and is not particularly limited. As a typical example of the synthesis method, the dye in this embodiment can be synthesized by reacting an intermediate, such as a quaternary ammonium salt, with a bridging agent or the like, or hemicyanine or the like by routes represented by the following reaction formulas (a) to (c).

The quaternary ammonium salt can be synthesized, for example, using a nitrogen-containing heterocyclic compound and an electrophile, such as an alkyl halide. In addition, anion exchange may be performed as required.

Reaction Formula (a)

[Formula 46]

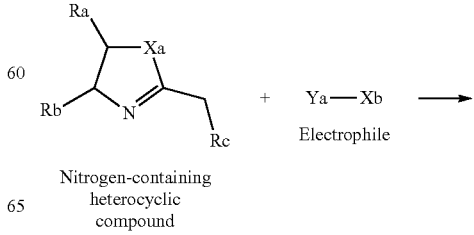

-continued

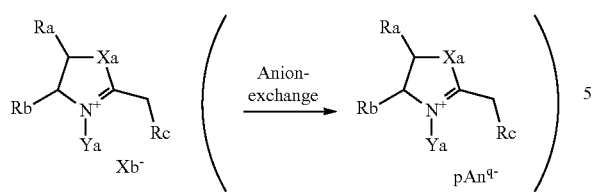

Quaternary ammonium salt

*X is a leaving group, such as a halogen

Reaction Formula (b)

A symmetrical trimethine dye and pentamethine dye can be synthesized using an intermediate, such as a quaternary ammonium salt, and a generally known bridging agent. In addition, compounds other than bridging agents are also widely known, and they are shown together.

[Formula 47]

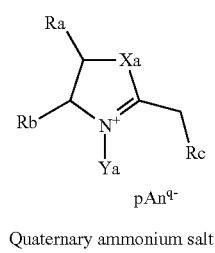

Quaternary ammonium salt

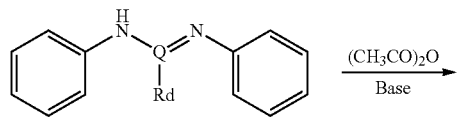

Bridging agent

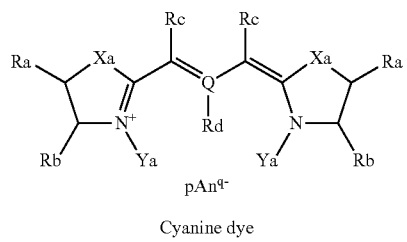

Cyanine dye

*Rc and Rd are each H or a substituent, such as a CN group

Examples of Compounds Other than Bridging Agents

[Formula 48]

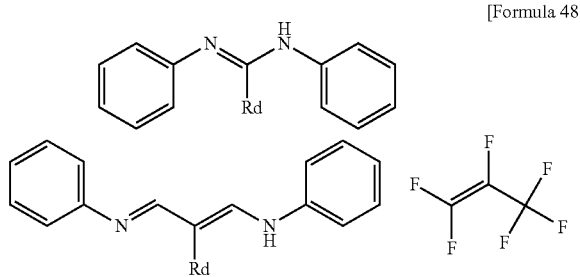

-continued

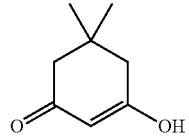

An asymmetrical trimethine and pentamethine dye can be synthesized, for example, using a quaternary ammonium salt and hemicyanine.

Reaction Formula (c)

[Formula 49]

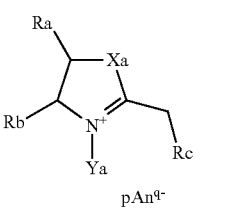

Quaternary ammonium salt

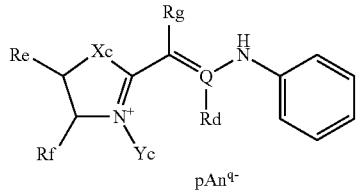

Hemicyanine

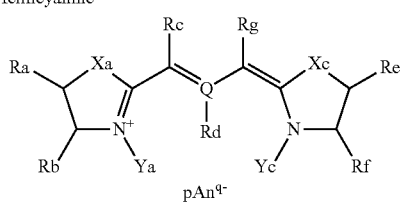

Cyanine dye

*Rc, Rd, and Rg are each H or a substituent, such as a CN group

The intermediate, such as a quaternary ammonium salt, described above is preferably a compound having a structure represented by the following formula (IX), more preferably a compound having a structure represented by the following formula (X). In addition, for a reason similar to the above, A in the structures represented by the following formula (IX) and the following formula (X) is more preferably any of the above-described formulas (IV) to (VII).

[Formula 50]

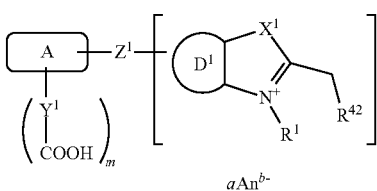

(IX)

wherein A is a structure having a maximum absorption wavelength λmax of 350 to 500 nm in a methanol solution; $Z^1$ is any one divalent linking group selected from —CONR—, —NRCO—, —SO$_2$NR—, and —NRSO$_2$—; R in Z$^1$ is a hydrogen atom, an alkyl group having 1 to 8 carbon atoms, or an arylalkyl group having 7 to 20 carbon atoms; D$^1$ is a benzene ring which may have a substituent, a naphthalene ring which may have a substituent, or a phenanthrene ring which may have a substituent; R$^1$ is a hydrogen atom, an alkyl group having 1 to 20 carbon atoms, an alkenyl group having 2 to 8 carbon atoms, or an alkynyl group having 2 to 8 carbon atoms, each of which may be substituted by a halogen atom, a nitro group, a cyano group, an amino group, a hydroxyl group, an ether group, a carbonyl group, an aromatic ring, a heterocyclic ring, or a metallocenyl group; R$^{42}$ are each independently a hydrogen atom, an alkyl group having 1 to 8 carbon atoms, an aryl group having 6 to 12 carbon atoms, a halogen atom, or a cyano group, and may be the same or different; X$^1$ is an oxygen atom, a sulfur atom, a selenium atom, CR$^3$R$^4$, or NR$^5$; R$^3$ to R$^5$ are each independently a hydrogen atom, an alkyl group having 1 to 20 carbon atoms, an alkenyl group having 2 to 8 carbon atoms, or an alkynyl group having 2 to 8 carbon atoms, and may be the same or different, where R$^3$ to R$^5$ may each be independently substituted by a halogen atom, a nitro group, a cyano group, an amino group, a hydroxyl group, an ether group, a carbonyl group, an aromatic ring, a heterocyclic ring, or a metallocenyl group, and R$^3$ and R$^4$ may be linked to form an alicyclic group having a 3- to 6-membered ring; Y$^1$ is an alkylene group having 1 to 8 carbon atoms, or a single bond; m is 0 to 2; An$^{b-}$ is a b-valent anion; a is 1 or 2, and is a coefficient for keeping the charge of the entire dye neutral; and b is 1 or 2.

[Formula 51]

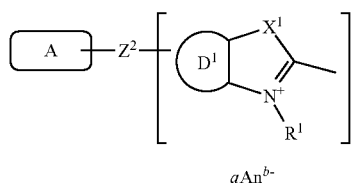

(X)

$a$An$^{b-}$ wherein A is a structure having a maximum absorption wavelength λmax of 350 to 500 nm in a methanol solution; Z$^2$ is any one divalent linking group selected from —CONR—, —NRCO—, —SO$_2$NR—, and —NRSO$_2$—; R in Z$^2$ is a hydrogen atom, an alkyl group having 1 to 8 carbon atoms, or an arylalkyl group having 7 to 20 carbon atoms; D$^1$ is a benzene ring which may have a substituent, a naphthalene ring which may have a substituent, or a phenanthrene ring which may have a substituent; R$^1$ is a hydrogen atom, an alkyl group having 1 to 20 carbon atoms, an alkenyl group having 2 to 8 carbon atoms, or an alkynyl group having 2 to 8 carbon atoms, each of which may be substituted by a halogen atom, a nitro group, a cyano group, an amino group, a hydroxyl group, an ether group, a carbonyl group, an aromatic ring, a heterocyclic ring, or a metallocenyl group; X$^1$ is an oxygen atom, a sulfur atom, a selenium atom, CR$^3$R$^4$, or NR$^5$; R$^3$ to R$^5$ are each independently a hydrogen atom, an alkyl group having 1 to 20 carbon atoms, an alkenyl group having 2 to 8 carbon atoms, or an alkynyl group having 2 to 8 carbon atoms, and may be the same or different, where R$^3$ to R$^5$ may each be independently substituted by a halogen atom, a nitro group, a cyano group, an amino group, a hydroxyl group, an ether group, a carbonyl group, an aromatic ring, a heterocyclic ring, or a metallocenyl group, and R$^3$ and R$^4$ may be linked to form an alicyclic group having a 3- to 6-membered ring; An$^{b-}$ is a b-valent anion; a is 1 or 2, and is a coefficient for keeping the charge of the entire dye neutral; and b is 1 or 2.

Specific examples (a-1) to (a-12) of the intermediate, such as a quaternary ammonium salt, which are included in the compounds having the structures represented by the above formula (IX) and the above formula (X) are illustrated below.

[Formula 52]

a-1

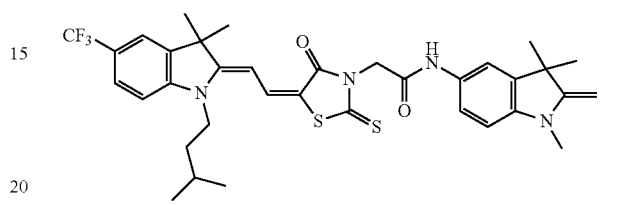

a-2

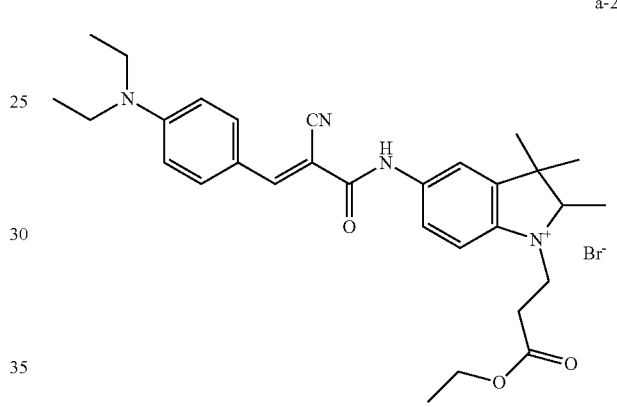

a-3

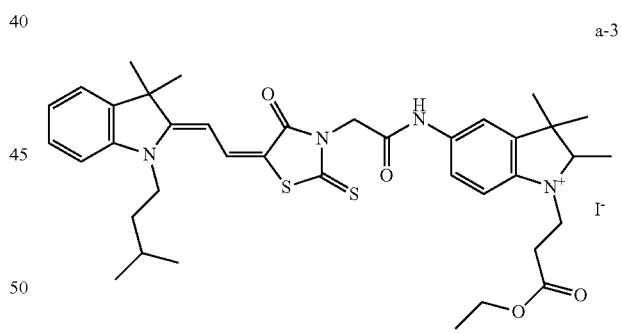

a-4

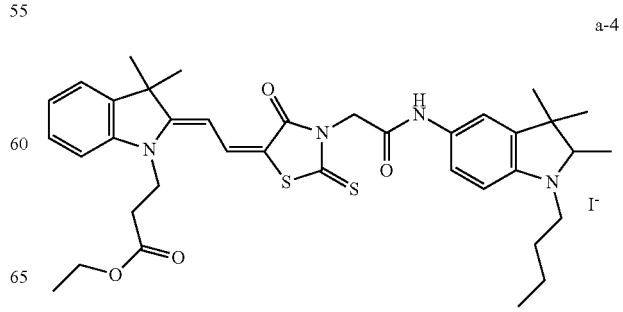

a-5
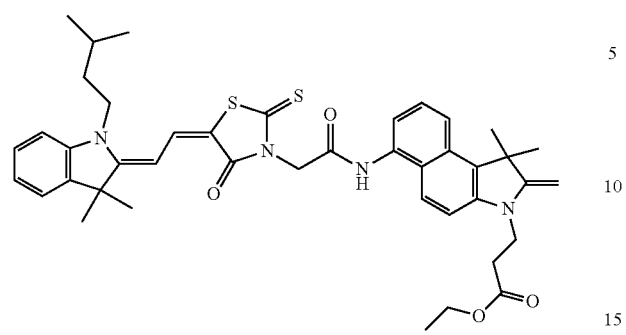
a-6
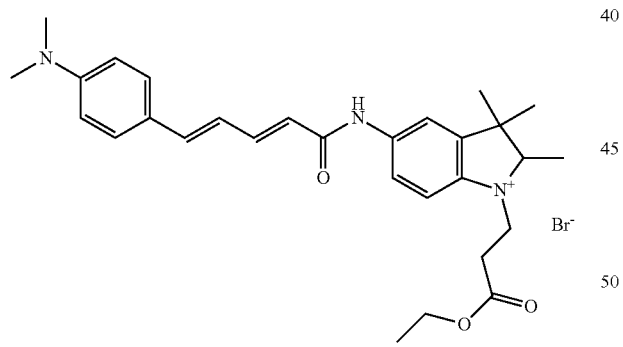
a-7
a-8
a-9
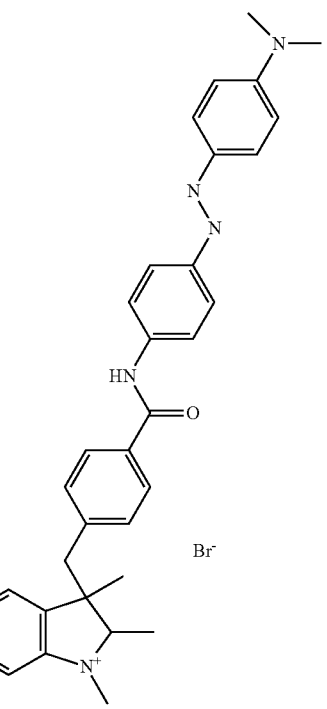
a-10
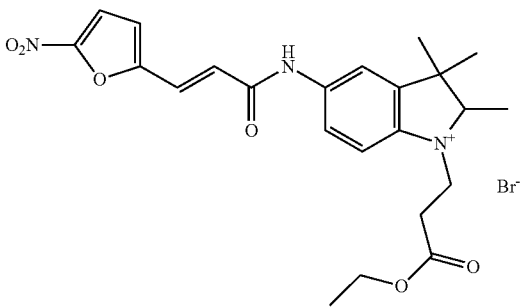
a-11
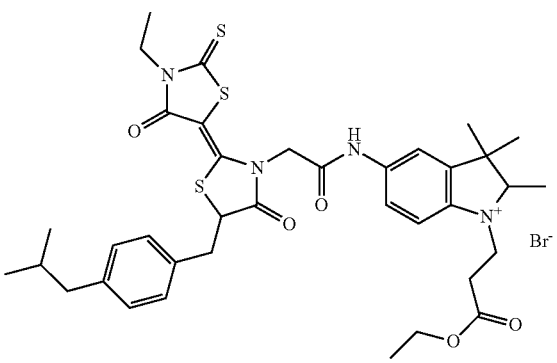

-continued a-12

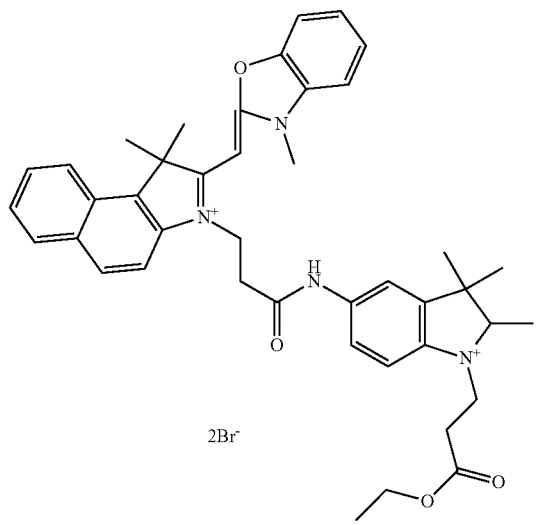

Next, an example of the use of a photoelectric conversion device dye in this embodiment will be described.

Figure 2:
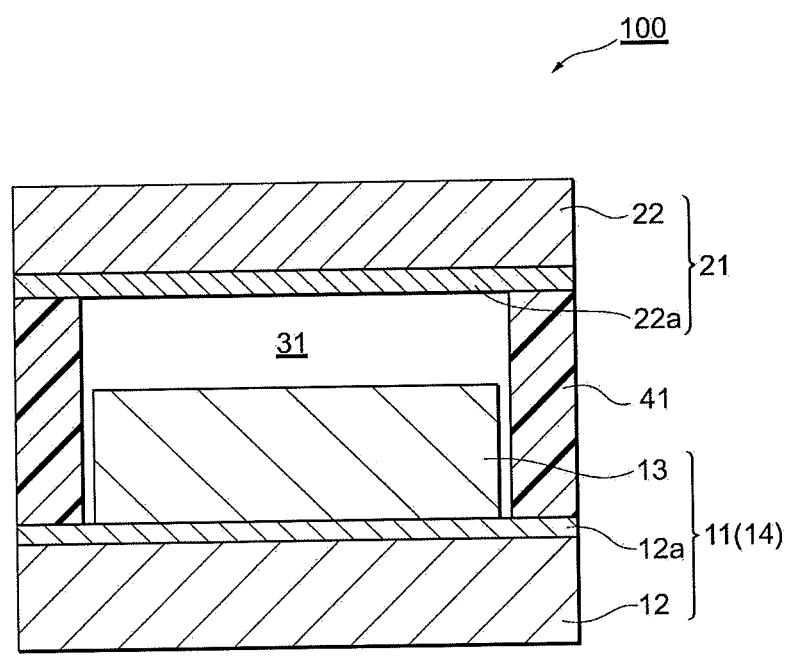
FIG. 2 is a cross-sectional view showing the schematic configuration of a dye-sensitized solar cell 100.
Figure 3:
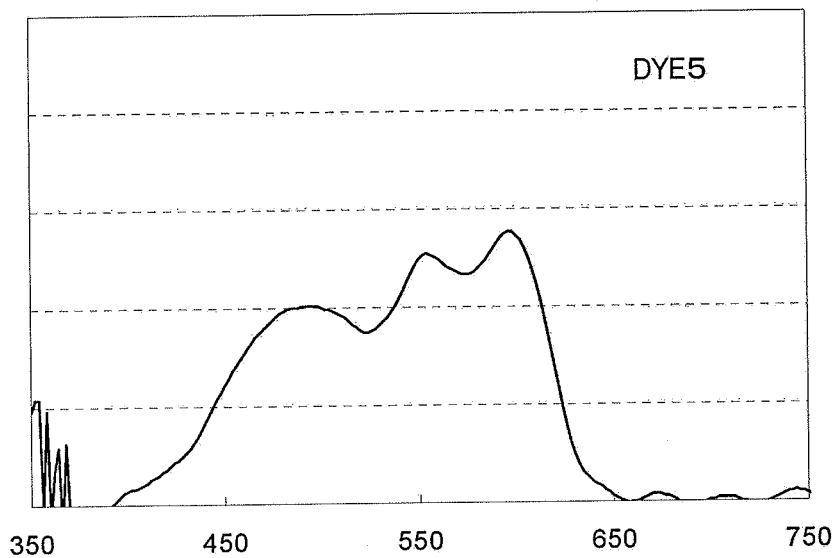
FIG. 3 shows the ultraviolet-visible absorption spectrum of a dye 5.
Figure 4:
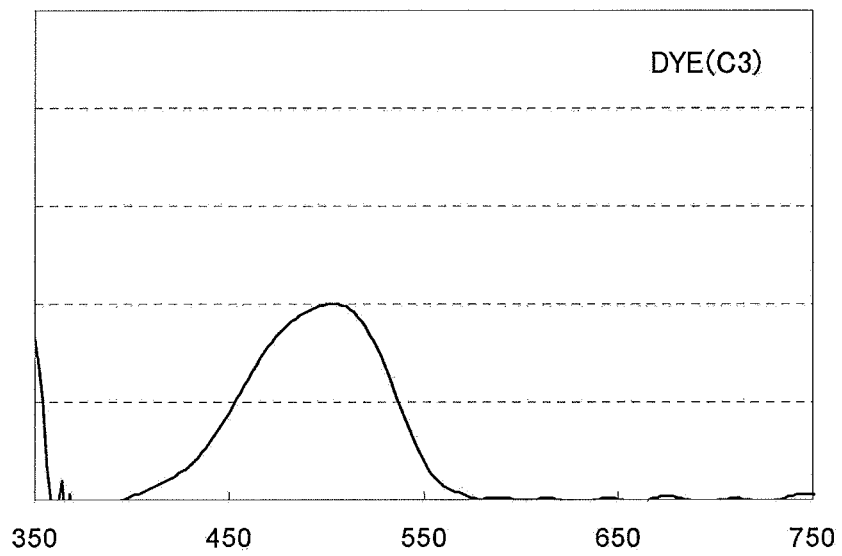
FIG. 4 shows the ultraviolet-visible absorption spectrum of dye (C3).
Figure 5:
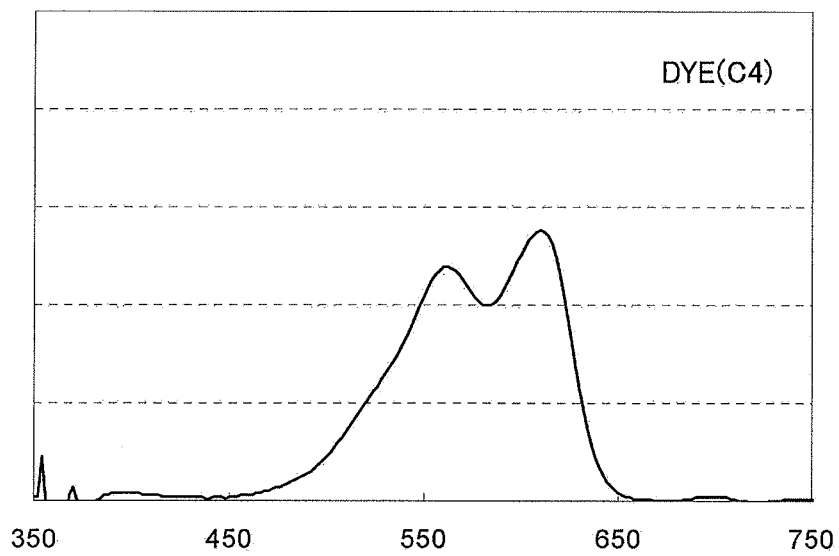
FIG. 5 shows the ultraviolet-visible absorption spectrum of dye (C4).
Figure 6:
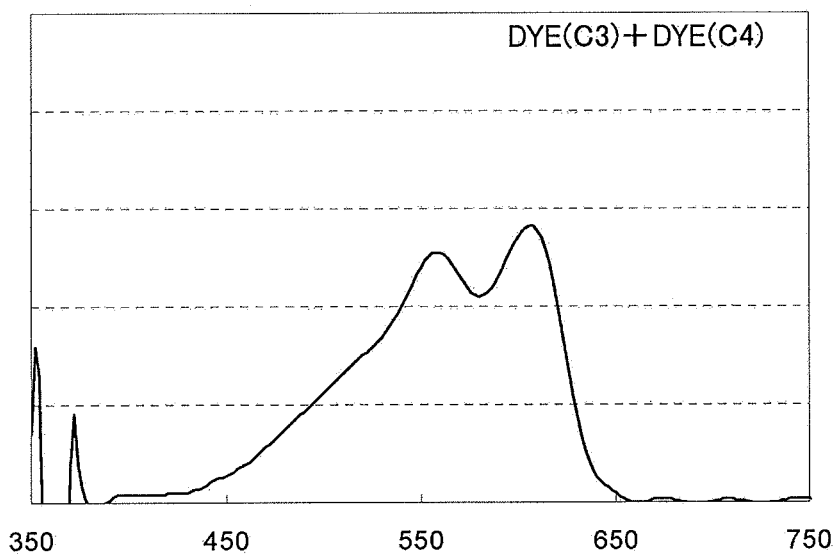
FIG. 6 shows the ultraviolet-visible absorption spectrum of a mixture of dye (C3) and dye (C4).

FIG. 2 is a cross-sectional view showing the schematic configuration of a dye-sensitized solar cell 100, which is a photoelectric conversion device in this embodiment.

The dye-sensitized solar cell 100 in this embodiment comprises a working electrode 11, a counter electrode 21, and an electrolyte 31 provided between these working electrode 11 and counter electrode 21. At least one of the working electrode 11 and the counter electrode 21 is an electrode having light transmission properties. The working electrode 11 and the counter electrode 21 are opposed to each other via a spacer 41, and the electrolyte 31 is enclosed in a sealing space defined by these working electrode 11, counter electrode 21, and spacer 41, and a sealing member not shown.

The working electrode 11 functions as a negative electrode with respect to an external circuit. The working electrode 11 comprises a porous metal oxide layer 13 (metal oxide semiconductor layer) containing a metal oxide (metal oxide semiconductor material) on the conductive surface 12a of a substrate 12, and the dye in this embodiment described above is supported (adsorbed) on the metal oxide layer 13, and thus, a dye-supported metal oxide electrode 14 is formed. In other words, the working electrode 11 in this embodiment has a configuration in which a composite structure in which the dye in this embodiment described above is supported (adsorbed) on the metal oxide surface of the metal oxide layer 13 is laminated on the conductive surface 12a of the substrate 12 (the dye-supported metal oxide electrode 14).

The type, dimensions, and shape of the substrate 12 are not particularly limited as long as it can support at least the metal oxide layer 13. For example, a plate-shaped or sheet-shaped one can be preferably used. Specific examples thereof include a glass substrate, a plastic substrate, such as polyethylene, polypropylene, polystyrene, tetraacetyl cellulose (TAC), polyethylene terephthalate (PET), polyethylene naphthalate (PEN), syndiotactic polystyrene (SPS), polyphenylene sulfide (PPS), polycarbonate (PC), polyarylate (PAR), polysulfone (PSF), polyester sulfone (PES), polyetherimide (PEI), cyclic polyolefin, or brominated phenoxy, a metal substrate or an alloy substrate, a ceramic substrate, or a laminate thereof. In addition, the substrate 12 preferably has light transmission properties, and one having excellent light transmission properties in the visible light region is more preferable. Further, the substrate 12 preferably has flexibility. In this case, structures in various forms utilizing the flexibility can be provided.

The conductive surface 12a can be provided on the substrate 12, for example, by forming a transparent conductive film on the substrate 12, like a conductive PET film. In addition, by using the substrate 12 having conductivity, the treatment for providing the conductive surface 12a on the substrate 12 can be omitted. Specific examples of the transparent conductive film include, but are not particularly limited to, a metal thin film comprising gold (Au), silver (Ag), platinum (Pt), or the like, and one formed of a conductive polymer or the like, as well as indium-tin oxide (ITO), indium-zinc oxide (IZO), $SnO_2$, and $InO_3$, as well as FTO (F—$SnO_2$) in which $SnO_2$ is doped with fluorine. Each of these may be used alone, or a plurality of these may be used in combination. The method for forming the transparent conductive film is not particularly limited, and a publicly known method, for example, vapor deposition, CVD, spraying, spin coating, or immersion, can be applied. In addition, the film thickness of the transparent conductive film can be appropriately set. The conductive surface 12a of the substrate 12 may be subjected to appropriate surface modification treatment as required. Specific examples thereof include, but are not particularly limited to, publicly known surface treatment, such as degreasing treatment with a surfactant, an organic solvent, an alkaline aqueous solution, or the like, mechanical polishing treatment, immersion treatment in an aqueous solution, preliminary electrolysis treatment with an electrolytic solution, water washing treatment, and drying treatment.

The metal oxide layer 13 is a support for supporting the dye. For the metal oxide layer 13, generally, one having a porous structure having many voids and a large surface area is used, and the metal oxide layer 13 is preferably one that is fine and has few voids, and is more preferably film-shaped. Particularly, the metal oxide layer 13 is more preferably a structure in which porous fine particles adhere.

The metal oxide layer 13 in this embodiment is a porous semiconductor layer comprising a metal oxide, such as titanium oxide, zinc oxide, tin oxide, niobium oxide, indium oxide, zirconium oxide, tantalum oxide, vanadium oxide, yttrium oxide, aluminum oxide, or magnesium oxide, as the main component. Only one of these metal oxides may be used alone, or two or more of these metal oxides may be combined (mixed, a mixed crystal, a solid solution, or the like) and used. For example, a combination of zinc oxide and tin oxide, titanium oxide and niobium oxide, or the like can be used. In terms of obtaining high energy conversion efficiency, the metal oxide layer 13 is preferably a layer substantially composed of titanium oxide or zinc oxide, more preferably a layer substantially composed of zinc oxide. Here, "substantially composed of titanium oxide" means comprising 95 wt % or more of titanium oxide, and "substantially composed of zinc oxide" means comprising 95 wt % or more of zinc oxide. The metal oxide layer 13 may comprise metals, such as titanium, tin, zinc, iron, tungsten, zirconium, strontium, indium, cerium, vanadium, niobium, tantalum, cadmium, lead, antimony, and bismuth, and metal oxides thereof and metal chalcogenides thereof. The thickness of the metal oxide layer 13 is not particularly limited, but is preferably 0.05 to 50 μm.

Examples of a method for forming the metal oxide layer 13 include, but are not particularly limited to, a method of providing a dispersion of a metal oxide on the conductive surface 12a of the substrate 12 and then drying it, a method of providing a dispersion or paste of a metal oxide (metal oxide slurry) on the conductive surface 12a of the substrate 12 and then high-temperature sintering it, and a method of providing a dispersion or paste of a metal oxide on the conductive surface 12a of the substrate 12 and then performing low-temperature treatment at about 50 to 150° C., as well as a method of performing cathode electrodeposition on the conductive surface 12a of the substrate 12 from an electrolytic solution containing a metal salt. Here, when a method that does not require high-temperature sintering is used, a plastic material having low heat resistance can be used as the substrate 12, and therefore, the working electrode 11 having high flexibility can be fabricated.

As a dye (sensitizing dye) that can inject electrons into a metal oxide by absorbing light and being excited, the dye in this embodiment described above is supported (adsorbed) on the metal oxide layer 13.

The dye may include, in addition to the dye in this embodiment described above, other dyes (sensitizing dyes). One having the desired light absorption band and absorption spectrum can be applied according to the performance required of the photoelectric conversion device.

Specific examples of the other dyes include an organic dye, such as xanthene, fluorescein, rhodamine, pyrogallol, dichlorofluorescein, Erythrosine B (Erythrosine is a registered trademark), fluorescin, Mercurochrome, a cyanine dye, a merocyanine dye, a trisazo dye, an anthraquinone dye, a polycyclic quinone dye, an indigo dye, a diphenylmethane dye, a trimethylmethane dye, a quinoline dye, a benzophenone dye, a naphthoquinone dye, a perylene dye, a fluorenone dye, a squarylium dye, an azulenium dye, a perinone dye, a quinacridone dye, a metal-free phthalocyanine dye, or a metal-free porphyrin dye. In addition, these other dyes preferably have an anchor group (for example, a carboxyl group, a sulfonic acid group, or a phosphoric acid group) that can be bonded or adsorbed on a metal oxide. Each of these other dyes may be used alone, or a plurality of these other dyes may be used in combination.

In addition, as the other dyes, for example, organometallic complex compounds can also be used. Specific examples of the organometallic complex compounds include an organometallic complex compound having both an ionic coordinate bond formed by a nitrogen anion in an aromatic heterocyclic ring and a metal cation, and a nonionic coordinate bond formed between a nitrogen atom or a chalcogen atom and a metal cation, and an organometallic complex compound having both an ionic coordinate bond formed by an oxygen anion or a sulfur anion and a metal cation, and a nonionic coordinate bond formed between a nitrogen atom or a chalcogen atom and a metal cation. More specific examples include a metal phthalocyanine dye, such as copper phthalocyanine or titanyl phthalocyanine, a metal naphthalocyanine dye, a metal porphyrin dye, and a ruthenium complex, such as a bipyridyl ruthenium complex, a terpyridyl ruthenium complex, a phenanthroline ruthenium complex, a bicinchoninic acid ruthenium complex, an azo ruthenium complex, or a quinolinol ruthenium complex. Each of these may be used alone, or a plurality of these may be used in combination.

In addition, the dye may comprise one or two or more additives. Examples of the additives include an aggregation inhibitor for inhibiting the aggregation of the dye, specifically, a cholic acid compound represented by the following formula (XI). These may be used alone, or a plurality of these may be mixed and used.

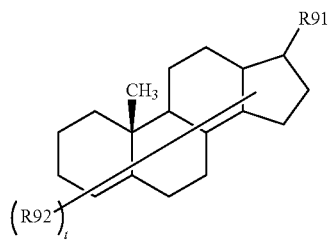

[Formula 53]

wherein R91 is an alkyl group having an acidic group; R92 represents a group bonded to any of carbon atoms constituting a steroid skeleton in the chemical formula, is a hydroxyl group, a halogen group, an alkyl group, an alkoxy group, an aryl group, a heterocyclic group, an acyl group, an acyloxy group, an oxycarbonyl group, an oxo group, or an acidic group, or a derivative thereof, and may be the same or different; t is an integer of 1 or more and 5 or less; and the bond between the carbon atoms constituting the steroid skeleton in the chemical formula may be a single bond or a double bond.

The method for supporting the dye on the metal oxide layer 13 is not particularly limited. Specific examples thereof include a method of immersing the metal oxide layer 13 in a solution comprising the dye, and a method of applying a solution comprising the dye to the metal oxide layer 13. The solvent of the dye-containing solution used here can be appropriately selected from publicly known solvents, for example, water, an ethanol solvent, a nitrile solvent, and a ketone solvent, according to the solubility, compatibility, or the like of the dye used.

Here, when the metal oxide layer 13 is formed by cathode electrodeposition, it is also possible to simultaneously perform the formation of the metal oxide layer 13 and dye support by using an electrolytic solution comprising a metal salt and the dye, to immediately form the dye-supported metal oxide electrode 14 in which the dye is supported (adsorbed) on the metal oxide surface of the metal oxide layer 13. The electrolysis conditions should be appropriately set according to the ordinary method according to the characteristics of the materials used. For example, when the dye-supported metal oxide electrode 14 composed of ZnO and the dye is formed, it is preferable that the reduction electrolysis potential is about −0.8 to −1.2 V (vs. Ag/AgCl), the pH is about 4 to 9, and the bath temperature of the electrolytic solution is about 0 to 100° C. In addition, it is preferable that the metal ion concentration in the electrolytic solution is about 0.5 to 100 mM, and the dye concentration in the electrolytic solution is about 50 to 500 μM. Further, in order to further enhance photoelectric conversion characteristics, it is possible to desorb the dye from the metal oxide layer 13 on which the dye is supported, once, and then readsorb another dye.

The working electrode 11 (metal oxide electrode 14) may have an intermediate layer between the conductive surface 12a of the substrate 12 and the metal oxide layer 13. The material of the intermediate layer is not particularly limited, but for example, the metal oxides described for the above transparent conductive film 12a are preferable. The intermediate layer can be formed by precipitating or depositing a metal oxide on the conductive surface 12a of the substrate 12 by a publicly known method, for example, vapor deposition, CVD, spraying, spin coating, immersion, or electrodeposition. The intermediate layer preferably has light transmission properties and further preferably has conductivity. In addition, the thickness of the intermediate layer is not particularly limited, but is preferably about 0.1 to 5 μm.

The counter electrode 21 functions as a positive electrode with respect to the external circuit. The counter electrode 21 is composed of a substrate 22 having a conductive surface 22a, and is opposed so that the conductive surface 21a faces the metal oxide layer 13 of the working electrode 11. For the substrate 22 and the conductive surface 22a, those publicly known can be appropriately used, as in the substrate 12 and the conductive surface 12a described above. For example, in addition to the substrate 12 having conductivity, the transparent conductive film 12a on the substrate 12, and a film (plate or foil) of a metal, such as platinum, gold, silver, copper, aluminum, indium, molybdenum, titanium, rhodium, ruthenium, or magnesium, carbon, a conductive polymer, or the like further formed on the transparent conductive film 12a of the substrate 12 can be used.

As the electrolyte 31, one generally used in a cell, a solar cell, or the like, such as a redox electrolyte having a redox pair, a quasi-solid electrolyte obtained by gelling this, or one obtained by forming a p-type semiconductor solid hole transport material into a film, can be appropriately used. For the electrolyte 31, one may be used alone, or two or more may be used in combination.

Examples of the redox electrolyte include an $I^-/I_3^-$ system, a $Br^-/Br_3^-$ system, or a quinone/hydroquinone system, specifically, a combination of a halide salt and a halogen simple substance, such as a combination of an iodide salt and an iodine simple substance, or a combination of a bromide salt and a bromine. The content of such a redox agent is not particularly limited, but is preferably $1 \times 10^{-4}$ to $1 \times 10^{-2}$ mol/g, more preferably $1 \times 10^{-3}$ to $1 \times 10^{-2}$ mol/g, with respect to the total amount of the electrolyte.

Examples of the above halide salt include cesium halides, quaternary alkylammonium halides, imidazolium halides, thiazolium halides, oxazolium halides, quinolinium halides, or pyridinium halides. More specifically, examples of iodide salts thereof include cesium iodide, quaternary alkylammonium iodides, such as tetraethylammonium iodide, tetrapropylammonium iodide, tetrabutylammonium iodide, tetrapentylammonium iodide, tetrahexylammonium iodide, tetraheptylammonium iodide, or trimethylphenylammonium iodide, imidazolium iodides, such as 3-methylimidazolium iodide or 1-propyl-2,3-dimethylimidazolium iodide, thiazolium iodides, such as 3-ethyl-2-methyl-2-thiazolium iodide, 3-ethyl-5-(2-hydroxyethyl)-4-methylthiazolium iodide, or 3-ethyl-2-methylbenzothiazolium iodide, oxazolium iodides, such as 3-ethyl-2-methyl-benzoxazolium iodide, quinolinium iodides, such as 1-ethyl-2-methylquinolinium iodide, or pyridinium iodides. In addition, examples of bromide salts include quaternary alkylammonium bromides. Among combinations of a halide salt and a halogen simple substance, a combination of at least one of the above-described iodide salts and an iodine simple substance is preferable.

In addition, the redox electrolyte may be, for example, a combination of an ionic liquid and a halogen simple substance. In this case, the above-described halide salts or the like may be further contained. For the ionic liquid, one generally used in a cell, a solar cell, or the like can be appropriately used, and the ionic liquid is not particularly limited. Specific examples of the ionic liquid include those disclosed in "Inorg. Chem." 1996, 35, p 1168 to 1178, "Electrochemistry" 2002, 2, p 130 to 136, National Publication of International Patent Application No. 9-507334, or Japanese Patent Laid-Open No. 8-259543.

The ionic liquid is preferably a salt having a melting point lower than room temperature (25° C.), or a salt that is liquefied at room temperature by dissolution with another molten salt or the like even if it has a melting point higher than room temperature. Specific examples of such an ionic liquid include anions and cations shown below.

Examples of ionic liquid cations include ammonium, imidazolium, oxazolium, thiazolium, oxadiazolium, triazolium, pyrrolidinium, pyridinium, piperidinium, pyrazolium, pyrimidinium, pyrazinium, triazinium, phosphonium, sulfonium, carbazolium, indolium, and derivatives thereof. Each of these may be used alone, or a plurality of these may be used in combination. Specific examples include 1-methyl-3-propylimidazolium, 1-butyl-3-methylimidazolium, 1,2-dimethyl-3-propylimidazolium, or 1-ethyl-3-methylimidazolium.

Examples of ionic liquid anions include a metal chloride, such as $AlCl_4^-$ or $Al_2Cl_7^-$, a fluorine-containing compound ion, such as $PF_6^-$, $BF_4^-$, $CF_3SO_3^-$, $N(CF_3SO_2)_2^-$, $F(HF)_n^-$, or $CF_3COO^-$, a non-fluorine compound ion, such as $NO_3^-$, $CH_3COO^-$, $C_6H_{11}COO^-$, $CH_3OSO_3^-$, $CH_3OSO_2^-$, $CH_3SO_3^-$, $CH_3SO_2^-$, $(CH_3O)_2PO_2^-$, $N(CN)_2^-$, or $SCN^-$, or a halide ion, such as an iodide ion or a bromide ion. Each of these may be used alone, or a plurality of these may be used in combination. Among these, an iodide ion is preferable as the ionic liquid anion.

The electrolyte 31 may be a liquid electrolyte (electrolytic solution) in which the above-described redox electrolyte is dissolved, dispersed, or suspended in a solvent, or a solid polymer electrolyte in which the above-described redox electrolyte is held in a polymer substance. In addition, the electrolyte 31 may be a quasi-solid-like (paste-like) electrolyte comprising a redox electrolyte and a particulate conductive carbon material, such as carbon black. Here, in this description, a "quasi-solid" means a concept including, in addition to a solid, a gel-like solid or a clay-like solid whose flowability is hardly seen but which can be deformed by the application of stress, and specifically means one in which no or slight shape change occurs due to self-weight after it is allowed to stand still and left for a certain time. The quasi-solid-like electrolyte comprising a conductive carbon material need not comprise a halogen simple substance because the conductive carbon material has the function of catalyzing a redox reaction.

The electrolyte 31 may comprise an organic solvent in which the above-described halide salt or ionic liquid or the like is to be dissolved, dispersed, swelled, or suspended. The organic solvent can be used without particular limitation as long as it is electrochemically inert, but an organic solvent having a melting point of 20° C. or less and a boiling point of 80° C. or more is preferable. By using an organic solvent having a melting point and a boiling point in this range, the durability tends to be enhanced. In addition, an organic solvent having high viscosity is preferable. Since high viscosity provides a high boiling point, electrolyte leakage tends to be inhibited even under a high-temperature environment. Further, an organic solvent having high electrical conductivity is preferable. Because of high electrical conductivity, high energy conversion efficiency tends to be obtained.

Specific examples of the organic solvent include hexane, benzene, toluene, quinoline, diethyl ether, chloroform, ethyl acetate, tetrahydrofuran, methylene chloride, acetone, acetonitrile, methoxyacetonitrile, propionitrile, butyronitrile, benzonitrile, 3-methoxypropionitrile, valeronitrile, N,N-dimethylformamide, dimethyl sulfoxide, sulfolane, acetic acid, formic acid, methanol, ethanol, 1-propanol, 2-propanol, 1-butanol, pentanol, methyl ethyl ketone, dimethyl carbonate, ethyl methyl carbonate, ethylene carbonate, propylene carbonate, ethylene glycol monoalkyl ether, propylene glycol monoalkyl ether, polyethylene glycol monoalkyl ether, polypropylene glycol monoalkyl ether, ethylene glycol, propylene glycol, polyethylene glycol, polypropylene glycol, glycerin, dioxane, 1,4-dioxane, ethylene glycol dialkyl ether, propylene glycol dialkyl ether, polyethylene glycol dialkyl ether, polypropylene glycol dialkyl ether, N-methylpyrrolidone, γ-butyrolactone, α-methyl-γ-butyrolactone, β-methyl-γ-butyrolactone, γ-valerolactone, and 3-methyl-γ-valerolactone. Among these, an organic solvent having at least one of a nitrile group, a carbonate structure, a cyclic ester structure, a lactam structure, an amide group, an alcohol group, a sulfinyl group, a pyridine ring, and a cyclic ether structure, as a functional group, is preferable because with an organic solvent having such a functional group, higher effects are obtained than with an organic solvent comprising none of these functional groups. Examples of the organic solvent having such a functional group include acetonitrile, propylnitrile, butyronitrile, methoxyacetonitrile, methoxypropionitrile, dimethyl carbonate, ethyl methyl carbonate, ethylene carbonate, propylene carbonate, N-methylpyrrolidone, pentanol, quinoline, N,N-dimethylformamide, γ-butyrolactone, dimethyl sulfoxide, or 1,4-dioxane, particularly, methoxypropionitrile, propylene carbonate, N-methylpyrrolidone, pentanol, quinoline, N,N-dimethylformamide, γ-butyrolactone, dimethyl sulfoxide, 1,4-dioxane, methoxyacetonitrile, and butyronitrile. Each of these organic solvents may be used alone, or a plurality of these organic solvents may be used in combination. In addition, the content of the organic solvent is preferably 10 to 80 wt % with respect to the total amount of the electrolyte 31.

The electrolyte 31 may comprise various additives according to the required performance. For the additives, those generally used in a cell, a solar cell, or the like can be appropriately used. Specific examples thereof include, but are not particularly limited to, a p-type conductive polymer, such as polyaniline, polyacetylene, polypyrrole, polythiophene, polyphenylene, polyphenylenevinylene, and derivatives thereof; a molten salt composed of a combination of an imidazolium ion, a pyridinium ion, a triazolium ion, and derivatives thereof with a halogen ion; a gelling agent; an oil gelling agent; a dispersing agent; a surfactant; and a stabilizer.

The method for disposing the electrolyte 31 between the working electrode 11 and the counter electrode 21 is not particularly limited, and various publicly known methods can be used. For example, the dye-supported metal oxide electrode 14, which is the working electrode 11, and the conductive surface 22a of the counter electrode 21 are opposed to each other at a predetermined interval via a spacer as required, and the peripheries are bonded to each other except a previously formed injection port, using a sealing agent or the like, and then, the whole is sealed. Then, the electrolyte is injected between the working electrode 11 and the counter electrode 21 from the injection port, and then, the injection port is sealed, and thus, the electrolyte 31 can be formed.

When a solid charge transfer material is used as the electrolyte 31, an electron transport material, a hole transport material, or the like is preferably used.

As the hole transport material, for example, aromatic amines and triphenylene derivatives are preferably used. Specific examples thereof include, but are not particularly limited to, an organic conductive polymer, such as an oligothiophene compound, polypyrrole, polyacetylene or a derivative thereof, poly(p-phenylene) or a derivative thereof, poly(p-phenylenevinylene) or a derivative thereof, polythienylenevinylene or a derivative thereof, polythiophene or a derivative thereof, polyaniline or a derivative thereof, or polytoluidine or a derivative thereof.

In addition, as the hole transport material, for example, a p-type inorganic compound semiconductor can also be used. In this case, a p-type inorganic compound semiconductor having a band gap of 2 eV or more is preferably used, and a p-type inorganic compound semiconductor having a band gap of 2.5 eV or more is more preferable. In addition, it is necessary that the ionization potential of the p-type inorganic compound semiconductor is smaller than the ionization potential of the working electrode 11 from the conditions under which the holes of the dye can be reduced. Although the preferable range of the ionization potential of the p-type inorganic compound semiconductor is different depending on the dye used, the ionization potential is preferably in the range of 4.5 eV or more and 5.5 eV or less, more preferably in the range of 4.7 eV or more and 5.3 eV or less.

As the p-type inorganic compound semiconductor, for example, a compound semiconductor comprising monovalent copper is preferably used. Specific examples of the compound semiconductor comprising monovalent copper include, but are not particularly limited to, CuI, CuSCN, $CuInSe_2$, $Cu(In, Ga)Se_2$, $CuGaSe_2$, $Cu_2O$, CuS, $CuGaS_2$, $CuInS_2$, $CuAlSe_2$, GaP, NiO, CoO, FeO, $Bi_2O_3$, $MoO_2$, and $Cr_2O_3$.

The method for forming the electrolyte 31 from the solid charge transfer material is not particularly limited, and various publicly known methods can be used. When a hole transport material comprising an organic conductive polymer is used, a method, for example, vacuum deposition, casting, application, spin coating, immersion, electrolytic polymerization, or photoelectrolytic polymerization, can be used. In addition, when an inorganic solid compound is used, a method, for example, casting, application, spin coating, immersion, or electrolytic plating, can be used.

In the dye-sensitized solar cell 100 in this embodiment, when light (sunlight, or ultraviolet light, visible light, or near infrared light equivalent to sunlight) is emitted to the working electrode 11, the dye absorbs the light, is excited, and injects electrons into the metal oxide layer 13. The injected electrons are transferred to the adjacent conductive surface 12a, and then reach the counter electrode 21 via the external circuit. On the other hand, the electrolyte 31 is oxidized so as to return (reduce) the dye, which is oxidized with the electron transfer, to the ground state. This oxidized electrolyte 31 is reduced by receiving the above electrons. In this manner, the electron transfer between the working electrode 11 and the counter electrode 21 and the accompanying redox reaction of the electrolyte 31 are repeated, and thus, continuous electron transfer occurs, and photoelectric conversion is steadily performed.

Here, in the dye-sensitized solar cell 100 in this embodiment, the dye having the structure represented by general formula (I) described above is used, and therefore, not only the absorption wavelength region is wider but also the energy transfer efficiency is better than those of conventional ones. Therefore, the proportion of the amount of electrons injected from the dye into the metal oxide layer 13 to the amount of emitted light is high, and the energy conversion efficiency can be improved. Especially, in the dye-sensitized solar cell 100 using the working electrode 11 in which the metal oxide layer 13 is substantially composed of zinc oxide, particularly the energy conversion efficiency is enhanced. Moreover, the dye having the structure represented by general formula (I) described above has excellent adsorption properties (adhesiveness) on a metal oxide layer, and therefore, the durability of the dye-sensitized solar cell 100 is also enhanced.

EXAMPLES

Hereinafter, the present invention will be described in detail with Synthesis Examples, Examples, and Comparative Examples, but it should be construed that the invention is in no way limited to those examples.

First, dyes (1) to (17) according to the dyes described in the above embodiments and intermediates (a-1) to (a-12) were synthesized by the following procedures.

Synthesis Example 1

An intermediate a-1 (0.13 mmol, 0.09 g), hemicyanine A (0.13 mmol, 0.05 g), triethylamine (0.26 mmol, 0.03 g), acetic anhydride (0.20 mmol, 0.02 g), and 1,2-dichloroethane (0.5 g) were put in, and heated to reflux for 1 hour. After the solvents were distilled away, hydrochloric acid (0.1 g) and acetic acid (1.0 g) were added to a reaction product, and then the resulting reaction product was stirred at 100° C. for 1 hour. Next, anion exchange was carried out using sodium iodide, and then, oil-water separation was carried out. After that, the resulting organic phase was purified by PLC (using a mobile phase solvent of chloroform/methanol (10:1)), and thus, 40 mg of a final product, dye (1), was obtained.

Synthesis Example 2

An intermediate a-1 (0.13 mmol, 0.09 g), hemicyanine B (0.13 mmol, 0.06 g), triethylamine (0.26 mmol, 0.03 g), acetic anhydride (0.20 mmol, 0.02 g), and 1,2-dichloroethane (0.5 g) were put in, and heated to reflux for 1 hour. After the solvents were distilled away, hydrochloric acid (0.1 g) and acetic acid (1.0 g) were added to a reaction product, and then the resulting reaction product was stirred at 100° C. for 1 hour. Next, anion exchange was carried out using sodium iodide, and then, oil-water separation was carried out. After that, the resulting organic phase was purified by PLC (using a mobile phase solvent of chloroform/methanol (10:1)), and thus, 40 mg of a final product, dye (2), was obtained.

[Formula 54]

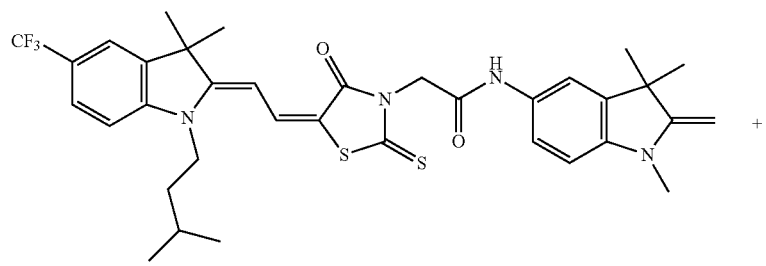

Intermediate (a-1)

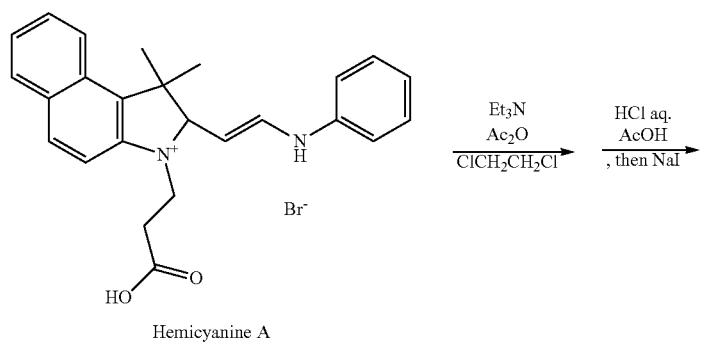

Hemicyanine A

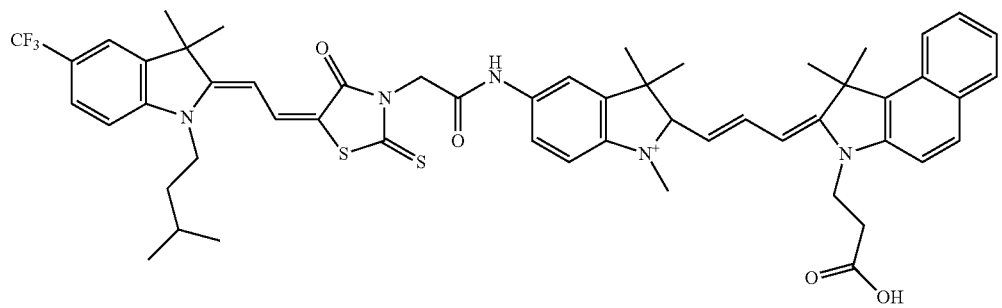

Dye (1)

[Formula 55]

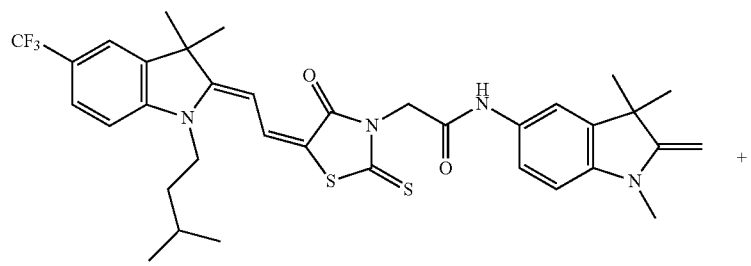

Intermediate (a-1)

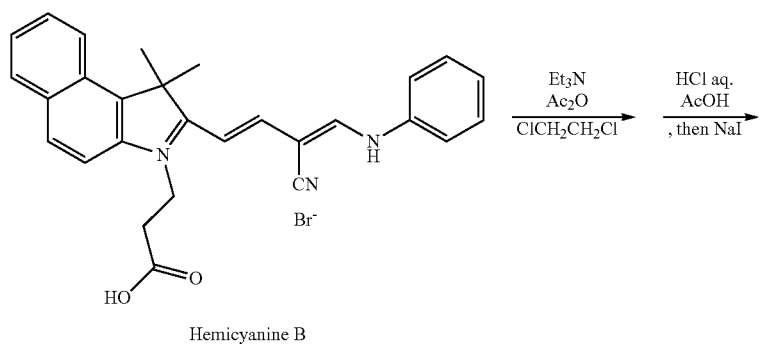

Hemicyanine B

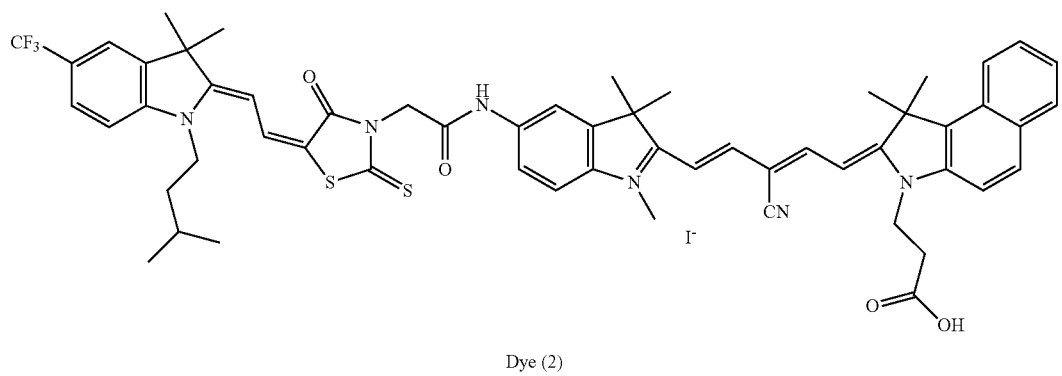

Dye (2)

Synthesis Example 3

A final product, dye (3), was obtained by the same process as that in Synthesis Example 1 except that an intermediate a-2 was used instead of intermediate a-1.

Synthesis Example 4

A final product, dye (4), was obtained by the same process as that in Synthesis Example 2 except that an intermediate a-2 was used instead of intermediate a-1.

Synthesis Example 5

A final product, dye (5), was obtained by the same process as that in Synthesis Example 1 except that an intermediate a-3 was used instead of intermediate a-1.

Synthesis Example 6

A final product, dye (6), was obtained by the same process as that in Synthesis Example 2 except that an intermediate a-3 was used instead of intermediate a-1.

Synthesis Example 7

An intermediate a-4 (0.13 mmol, 0.10 g), hemicyanine C (0.13 mmol, 0.05 g), triethylamine (0.26 mmol, 0.03 g), acetic anhydride (0.20 mmol, 0.02 g), and 1,2-dichloroethane (0.5 g) were put in, and heated to reflux for 1 hour. After the solvents were distilled away, hydrochloric acid (0.1 g) and acetic acid (1.0 g) were added to a reaction product, and then the resulting reaction product was stirred at 100° C. for 1 hour. Next, anion exchange was carried out using sodium iodide, and then, oil-water separation was carried out. After that, the resulting organic phase was purified by PLC (using a mobile phase solvent of chloroform/methanol (10:1)), and thus, 3 mg of a final product, dye (7), was obtained.

[Formula 56]

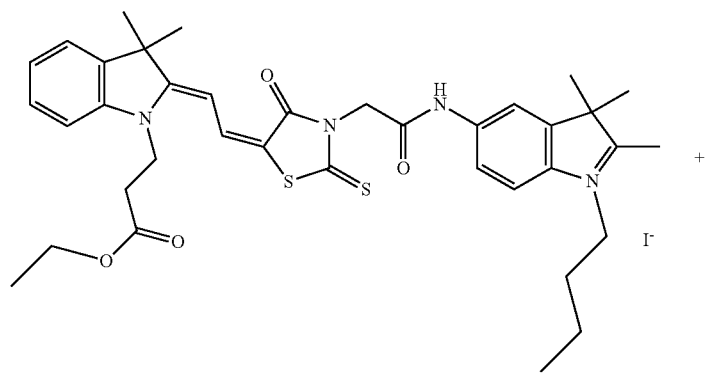

Intermediate (a-4)

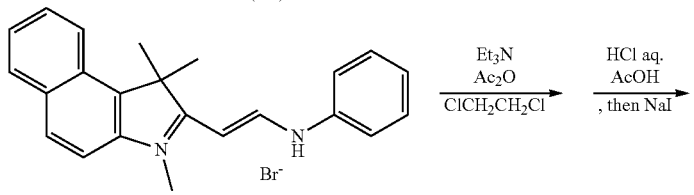

Hemicyanine C

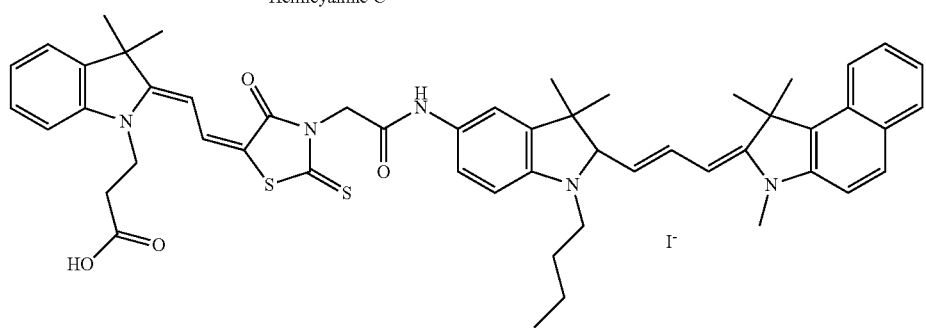

Dye (7)

Synthesis Example 8

A final product, dye (8), was obtained by the same process as that in Synthesis Example 7 except that an intermediate a-5 was used instead of intermediate a-4.

Synthesis Example 9

A final product, dye (9), was obtained by the same process as that in Synthesis Example 1 except that an intermediate a-6 was used instead of intermediate a-1.

Synthesis Example 10

A final product, dye (10), was obtained by the same process as that in Synthesis Example 1 except that an intermediate a-7 was used instead of intermediate a-1.

Synthesis Example 11

A final product, dye (11), was obtained by the same process as that in Synthesis Example 1 except that an intermediate a-8 was used instead of intermediate a-1.

Synthesis Example 12

A final product, dye (12), was obtained by the same process as that in Synthesis Example 2 except that an intermediate a-9 was used instead of intermediate a-1.

Synthesis Example 13

A final product, dye (13), was obtained by the same process as that in Synthesis Example 2 except that an intermediate a-10 was used instead of intermediate a-1.

Synthesis Example 14

A final product, dye (14), was obtained by the same process as that in Synthesis Example 2 except that an intermediate a-11 was used instead of intermediate a-1.

Synthesis Example 15

A final product, dye (15), was obtained by the same process as that in Synthesis Example 2 except that an intermediate a-4 was used instead of intermediate a-1.

Synthesis Example 16

An intermediate a-3 (0.18 mmol, 0.15 g), a bridging agent (0.09 mmol, 0.026 g), triethylamine (0.19 mmol, 0.019 g), acetic anhydride (0.19 mmol, 0.019 g), and 1,2-dichloroethane (0.5 g) were put in, and heated to reflux for 1 hour. After the solvents were distilled away, hydrochloric acid (0.1 g) and acetic acid (1.0 g) were added to a reaction product, and then the resulting reaction product was stirred at 100° C. for 1 hour. After performing oil-water separation, the resulting organic phase was purified by PLC (using a mobile phase solvent of chloroform/methanol (10:1)), and thus, 8 mg of a final product, dye (16), was obtained.

Synthesis Example 17

A final product, dye (17), was obtained by the same process as that in Synthesis Example 2 except that an intermediate a-12 was used instead of intermediate a-1.

Synthesis Example 18

First, a yellow dye A (1.0 mmol, 0.50 g) and chloroform (5 ml) were put in, and then, oxalyl chloride (1.1 mmol, 0.14 g) and dimethylformamide (0.1 ml) were added thereto in this order, and the resulting mixture was stirred at room temperature for 1 hour. After the mixture was cooled to 10° C.,

[Formula 57]

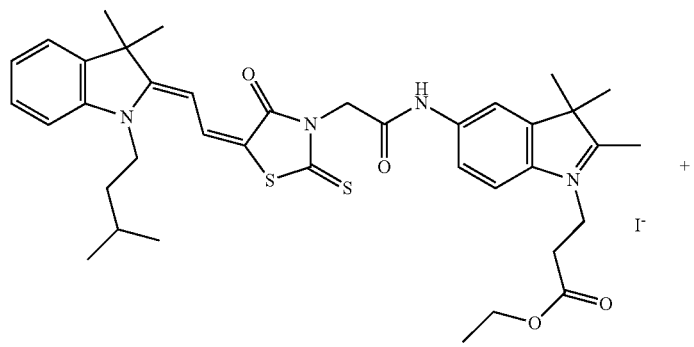

Intermediate (a-3)

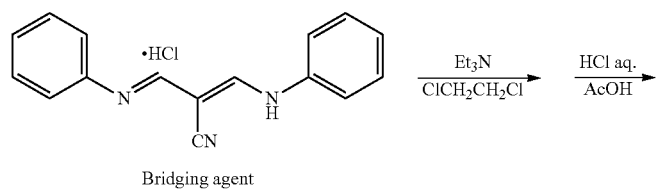

Bridging agent

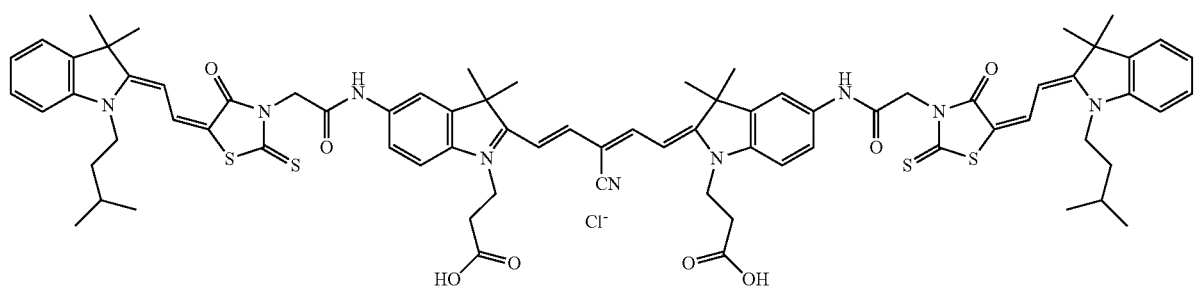

Dye (16)

5-aminoindolenine (1.0 mmol, 0.17 g) and triethylamine (2.0 mmol, 0.20 g) were added thereto, and the resulting mixture was stirred at room temperature for 2 hours. Oil-water separation was performed after addition of water (5 ml), and then, the resulting organic phase was purified by PLC (using a mobile phase solvent of chloroform/methanol (10:1)), and thus, 0.53 g of the objective indolenine A was obtained. In this way, an indolenine compound having an amide bond (or sulfonamide bond) was obtained by the corresponding amino compound and the corresponding carboxylic acid (or sulfonic acid) compound, and the following indolenine B to L were synthesized by the same process.

[Formula 58]

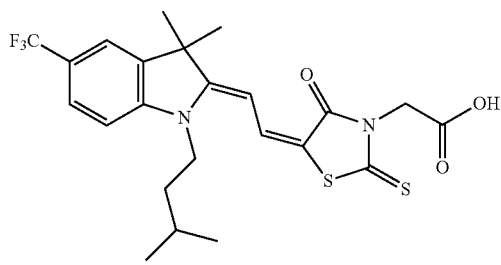
Yellow dye A

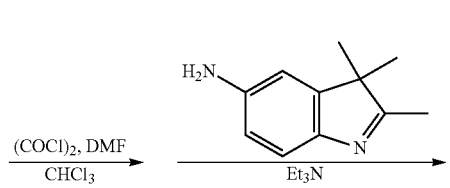

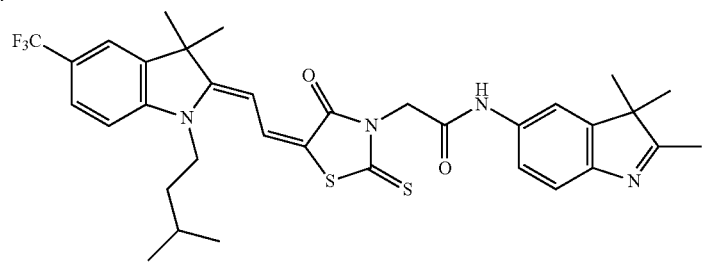
Indolenine A

Next, indolenine A (0.81 mmol, 0.53 g) and methyl para-toluenesulfonate (1.2 mmol, 0.22 g) were put in, and the resulting mixture was stirred at 100° C. for 2 hours. After the mixture was cooled to room temperature, the reaction solution was purified by PLC (using a mobile phase solvent of chloroform/methanol (10:1)), and thus, 0.19 g of the objective intermediate (a-1) was obtained.

[Formula 59]

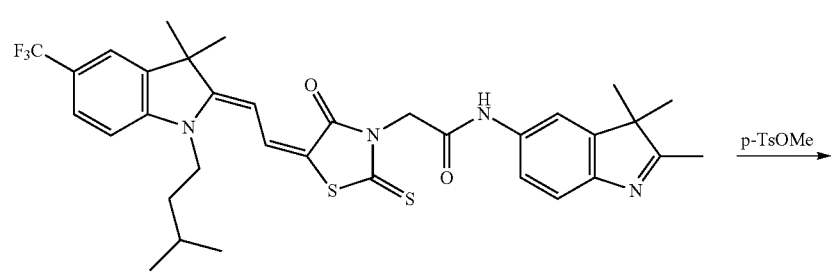
Indolenine A

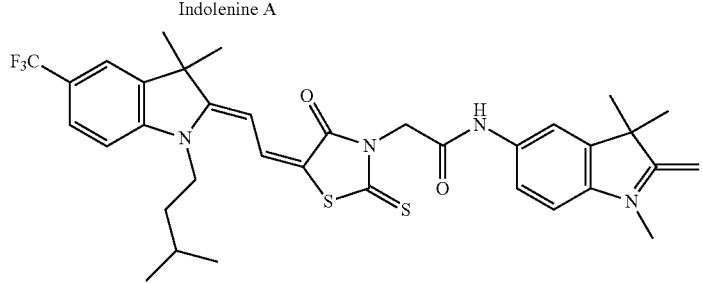
Intermediate (a-1)

Synthesis Example 19

The objective intermediate (a-2) was obtained by the same process as that in Synthesis Example 18 except that indolenine B and ethyl bromopropionate were used instead of indolenine A and methyl para-toluenesulfonate, respectively.

[Formula 60]

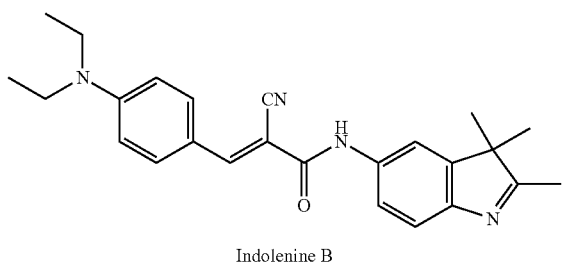

Indolenine B

Synthesis Example 20

The objective intermediate (a-3) was obtained by the same process as that in Synthesis Example 18 except that indolenine C and ethyl bromopropionate were used instead of indolenine A and methyl para-toluenesulfonate, respectively, and anion exchange with iodine anion was carried out after reaction.

[Formula 61]

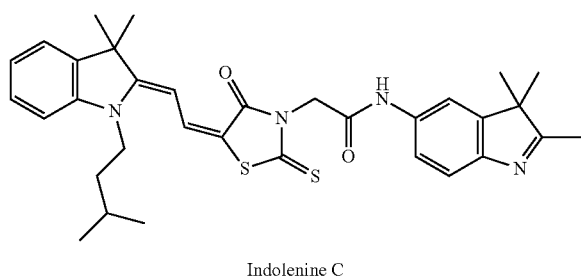

Indolenine C

Synthesis Example 21

The objective intermediate (a-4) was obtained by the same process as that in Synthesis Example 18 except that indolenine D and iodobutane were used instead of indolenine A and methyl para-toluenesulfonate, respectively.

[Formula 62]

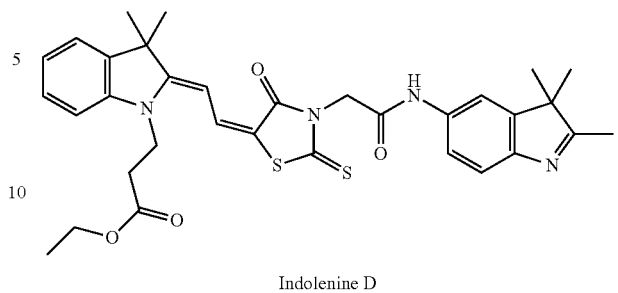

Indolenine D

Synthesis Example 22

The objective intermediate (a-5) was obtained by the same process as that in Synthesis Example 18 except that indolenine E and ethyl bromopropionate were used instead of indolenine A and methyl para-toluenesulfonate, respectively.

[Formula 63]

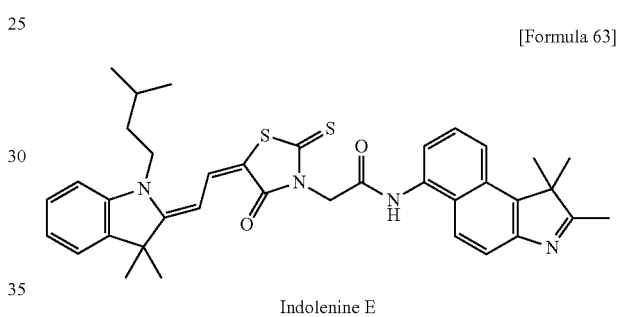

Indolenine E

Synthesis Example 23

The objective intermediate (a-6) was obtained by the same process as that in Synthesis Example 18 except that indolenine F and ethyl bromopropionate were used instead of indolenine A and methyl para-toluenesulfonate, respectively.

[Formula 64]

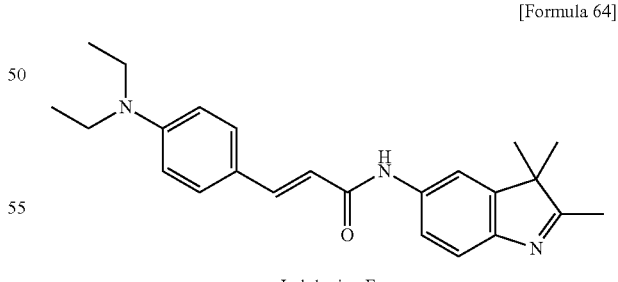

Indolenine F

Synthesis Example 24

The objective intermediate (a-7) was obtained by the same process as that in Synthesis Example 18 except that indolenine G and ethyl bromopropionate were used instead of indolenine A and methyl para-toluenesulfonate, respectively.

[Formula 65]

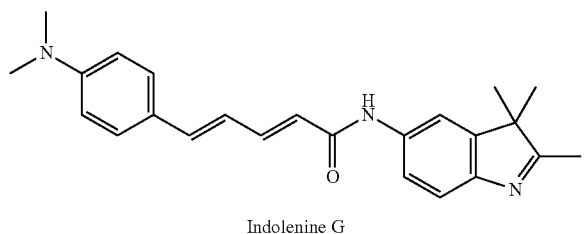

Indolenine G

Synthesis Example 25

The objective intermediate (a-8) was obtained by the same process as that in Synthesis Example 18 except that indolenine H was used instead of indolenine A.

[Formula 66]

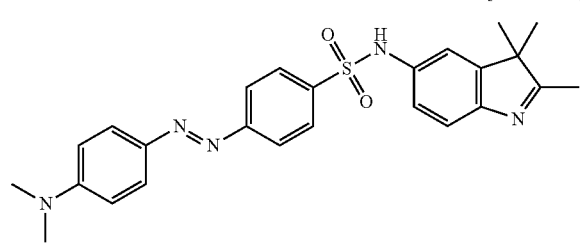

Indolenine H

Synthesis Example 26

The objective intermediate (a-9) was obtained by the same process as that in Synthesis Example 18 except that indolenine I was used instead of indolenine A, and anion exchange with bromine anion was carried out after reaction.

[Formula 67]

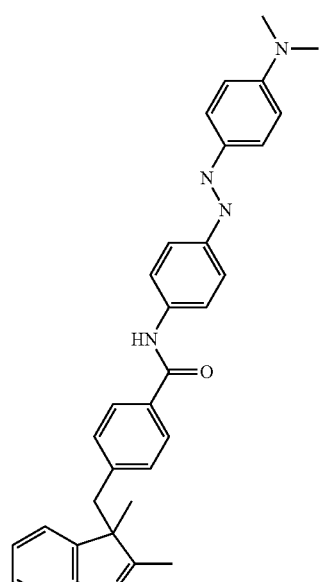

Indolenine I

Synthesis Example 27

The objective intermediate (a-10) was obtained by the same process as that in Synthesis Example 18 except that indolenine J and ethyl bromopropionate were used instead of indolenine A and methyl para-toluenesulfonate, respectively.

[Formula 68]

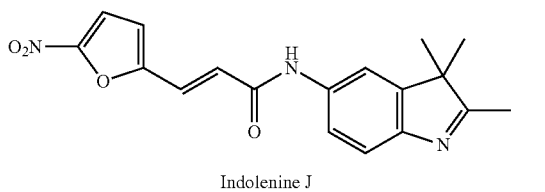

Indolenine J

Synthesis Example 28

The objective intermediate (a-11) was obtained by the same process as that in Synthesis Example 18 except that indolenine K and ethyl bromopropionate were used instead of indolenine A and methyl para-toluenesulfonate, respectively.

[Formula 69]

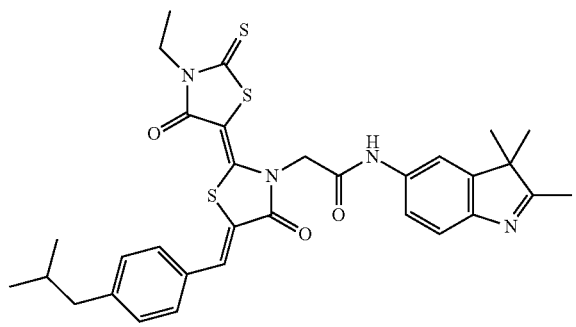

Indolenine K

Synthesis Example 29

The objective intermediate (a-12) was obtained by the same process as that in Synthesis Example 18 except that indolenine L and ethyl bromopropionate were used instead of indolenine A and methyl para-toluenesulfonate, respectively.

[Formula 70]

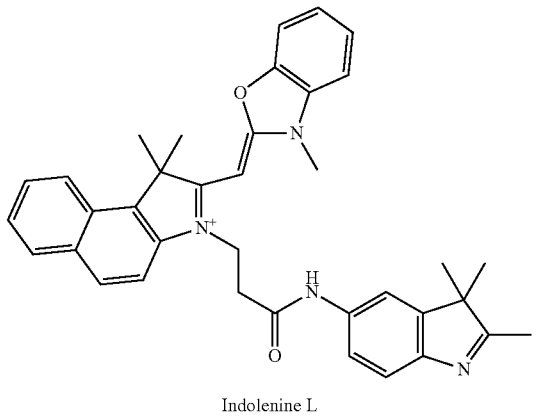

Indolenine L

The structures of dyes (1) to (17) which were the final products in Synthesis Examples 1 to 17 and intermediates (a-1) to (a-12) obtained in Synthesis Examples 18 to 29 were identified by a nuclear magnetic resonance (NMR) method. In addition, for each of dyes (1) to (17) which were the final products in Synthesis Examples 1 to 17, a maximum absorption wavelength ($\lambda$max) was measured. The results are shown in Tables 1 to 4.

It is noted that Lambda-400 manufactured by JEOL Ltd. was used as a measuring device in the NMR measurement. In this case, a solution prepared by dissolving 3 to 10 mg of the final product in 1 cm$^3$ of a deuterated solvent was used as a measurement sample, and a $^1$H-NMR spectrum was measured at room temperature.

Moreover, for the measurement of the maximum absorption wavelength ($\lambda$max), a UV spectrometer (U-3010) manufactured by Hitachi, Ltd. was used. In this case, a measurement sample prepared by adding the final product to methanol (CH$_3$OH; solvent) so that the absorbance was in the range of 0.5 to 1.0 was used for the measurement.

TABLE 1

| Synthesis Example | $^1$H NMR |
|---|---|
| Synthesis Example 1 (DMSO-d6) | 10.65 (s, 1H), 8.40 (t, 1H), 8.27 (d, 1H), 8.06 (t, 2H), 7.89 (d, 1H), 7.85 (d, 1H), 7.87 (d, 1H), 7.68-7.61 (m, 2H), 7.52-7.42 (m, 3H), 7.29 (d, 1H), 6.48 (t, 2H), 5.51 (d, 1H), 4.87 (s, 2H), 4.39 (t, 2H), 3.97 (t, 2H), 3.64 (s, 3H), 2.49 (t, 2H), 1.95 (s, 6H), 1.67-1.50 (m, 15H), 1.00 (d, 6H) |
| Synthesis Example 2 (DMSO-d6) | 10.85 (s, 1H), 8.63 (d, 1H), 8.50 (d, 1H), 8.24 (d, 1H), 8.11-8.05 (m, 3H), 7.88-7.83 (m, 3H), 7.71-7.66 (m, 2H), 7.54 (t, 2H), 7.44 (d, 1H), 7.29 (d, 1H), 6.38 (d, 1H), 6.24 (d, 1H), 5.51 (d, 1H), 4.88 (s, 2H), 4.50 (t, 2H), 3.96 (t, 2H), 3.72 (s, 3H), 2.67 (t, 2H), 1.94 (s, 6H), 1.73-1.50 (m, 15H), 1.00 (d, 6H) |
| Synthesis Example 3 (CDCl$_3$) | 9.03 (s, 1H), 8.33 (s, 1H), 8.18 (s, 1H), 7.96 (d, 3H), 7.89 (d, 1H), 7.77 (d, 2H), 7.69 (d, 1H), 7.39 (d, 1H), 7.33 (d, 1H), 6.71 (d, 3H), 6.65 (d, 3H), 4.42-4.59 (m, 4H) 3.52-3.41 (m, 4H), 2.82 (t, 4H), 1.26-1.17 (m, 18H) |
| Synthesis Example 4 (DMSO-d6) | 8.58 (d, 1H), 8.47 (d, 1H), 8.22 (d, 1H), 8.11-8.01 (m, 4H), 7.90-7.85 (m, 3H), 7.66 (t, 2H), 7.53 (d, 2H), 6.80 (d, 2H), 6.39 (d, 2H), 4.52-4.39 (m, 4H), 3.46 (b, 4H), 2.65 (t, 4H), 1.91 (s, 6H), 1.69 (s, 6H), 1.13 (t, 6H) |
| Synthesis Example 5 (DMSO-d6) | 10.52 (s, 1H), 8.39 (t, 1H), 8.26-8.23 (m, 2H), 8.04 (s, 2H), 7.88-7.85 (m, 2H), 7.72 (d, 1H), 7.62 (t, 1H), 7.50-7.41 (m, 4H), 7.31 (t, 1H), 7.14-7.08 (m, 2H), 6.60-6.50 (m, 2H), 4.85 (s, 2H), 4.44 (t, 2H), 4.32 (t, 2H), 3.92 (t, 2H), 2.65-2.58 (m, 4H), 1.93 (s, 6H), 1.68-1.54 (m, 13H), 1.01-0.91 (m, 8H) |
| Synthesis Example 6 (DMSO-d6) | 10.61 (s, 1H), 8.48 (d, 1H), 8.21 (d, 1H), 8.08 (d, 1H), 8.05 (d, 1H), 7.95 (s, 1H), 7.88-7.84 (m, 2H), 7.67 (t, 1H), 7.51 (d, 2H), 7.43 (d, 2H), 7.28 (d, 1H), 7.13-7.06 (m, 3H), 6.40-6.36 (m, 3H), 4.86 (s, 2H), 4.54 (t, 2H), 4.40 (t, 2H), 3.92 (t, 2H), 2.70-2.60 (m, 4H), 1.89 (s, 6H), 1.73-1.56 (m, 13H), 1.01-0.96 (m, 8H) |
| Synthesis Example 7 (CDCl$_3$) | 8.51 (t, 1H), 8.10 (d, 2H), 7.97-7.92 (m, 4H), 7.60 (t, 1H), 7.42-7.33 (m, 3H), 7.25-7.22 (m, 3H), 7.04-6.99 (m, 2H), 6.61-6.55 (m, 2H), 5.00 (s, 2H), 4.15-4.12 (m, 4H), 3.86 (s, 3H), 2.85 (t, 2H), 1.77 (s, 6H), 1.75 (s, 6H), 1.46 (m, 2H), 1.25 (s, 6H), 1.03 (t, 2H), 0.88 (t, 3H) |
| Synthesis Example 8 (CDCl$_3$) | 8.60 (t, 1H), 8.23 (d, 1H), 8.09 (d, 1H), 7.93-7.80 (m, 4H), 7.78 (d, 1H), 7.65-7.42 (m, 6H), 7.21 (d, 2H), 7.06 (t, 1H), 6.99-6.90 (m, 2H), 6.82 (d 1H), 5.18 (s, 2H), 4.51 (t, 2H), 3.86 (s, 3H), 3.72 (t, 2H), 3.05 (t, 2H), 1.97 (s, 6H), 1.61 (s, 6H), 1.42 (m, 1H), 1.02 (s, 6H), 0.92-0.86 (m, 8H) |
| Synthesis Example 9 (CD$_3$OD) | 8.60 (t, 1H), 8.25 (d, 1H), 8.00 (m, 3H), 7.72-7.38 (m, 8H), 6.88 (d, 2H), 6.48 (m, 3H), 4.38 (m, 4H), 3.41 (t, 3H), 2.69 (m, 4H), 2.03 (s, 6H), 1.79 (s, 6H), 1.17 (t, 3H) |
| Synthesis Example 10 (CD$_3$OD) | 8.55 (m, 1H), 8.16 (d, 1H), 7.89 (t, 2H), 7.56 (d, 1H), 7.53 (t, 3H), 7.42-7.24 (m, 7H), 7.05 (d, 2H), 6.61 (d, 2H), 6.45 (m, 2H), 4.41 (d, 2H), 4.29 (d, 2H), 2.91 (s, 6H), 2.57 (m, 4H), 1.95 (s, 6H), 1.19 (s, 6H) |

TABLE 2

| | |
|---|---|
| Synthesis Example 11 (CD$_3$OD) | 8.54 (m, 1H), 8.22 (d, 1H), 8.01 (t, 2H), 7.80 (m, 2H), 7.69 (d, 1H), 7.64 (t, 1H), 7.20-7.12 (m, 3H), 6.78 (d, 2H), 6.51 (d, 2H), 6.33 (d, 2H), 4.45 (m, 4H), 3.61 (s, 3H), 3.06 (s, 6H), 2.64 (m, 4H), 2.01 (s, 6H), 1.74 (s, 6H) |
| Synthesis Example 12 (CD$_3$OD) | 8.52 (d, 2H), 8.17 (d, 1H), 7.99-7.93 (m, 2H), 7.80 (s, 1H), 7.79-7.59 (m, 9H), 7.50 (d, 2H), 7.48 (t, 1H), 7.31 (t, 2H), 7.08 (d, 1H), 6.74 (d, 2H), 6.69 (d, 2H), 6.55 (d, 1H), 6.29 (d, 1H), 4.56 (t, 2H), 3.71 (d, 1H), 3.56 (d, 1H), 3.36 (s, 3H), 3.20 (s, 6H), 2.71 (t, 2H), 1.94 (s, 6H), 1.87 (s, 3H) |
| Synthesis Example 13 (CD$_3$OD) | 8.51 (d, 1H), 8.41 (d, 1H), 8.24 (d, 1H), 8.07-7.99 (m, 4H), 7.78 (d, 1H), 7.66 (t, 1H), 7.52-7.46 (m, 4H), 7.00-6.96 (m, 3H), 6.51 (d, 1H), 6.46 (d, 1H), 4.59 (t, 2H), 4.46 (t, 2H), 2.73 (t, 2H), 2.68 (t, 2H), 2.00 (s, 6H), 1.76 (s, 6H) |
| Synthesis Example 14 (CD$_3$OD) | 8.53 (d, 1H), 8.43 (d, 1H), 8.26 (d, 1H), 8.06 (d, 1H), 8.02 (d, 1H), 7.95 (s, 1H), 7.83-7.79 (m, 2H), 7.69-7.53 (m, 5H), 7.37 (d, 3H), 6.56 (d, 1H), 6.49 (d, 1H), 4.91 (s, 2H), 4.60 (t, 2H), 4.47 (t, 2H), 4.15 (q, 2H), 2.74 (t, 2H), 2.69 (t, 2H), 2.58 (d, 2H), 2.01 (s, 6H), 1.90 (s, 6H), 1.33-1.23 (m, 4H), 0.96 (d, 6H) |
| Synthesis Example 15 (CD$_3$OD) | 8.50 (d, 1H), 8.42 (d, 1H), 8.23 (d, 1H), 8.04 (d, 1H), 8.01 (d, 1H), 7.94 (s, 1H), 7.91-7.87 (m, 4H), 7.78 (d, 1H), 7.66 (t, 1H), 7.52 (d, 1H), 7.47 (d, 1H), 7.41-7.39 (m, 2H), 7.23-7.21 (m, 2H), 6.54 (d, 1H), 6.40 (d, 1H), 4.96 (s, 2H), 4.60 (t, 2H), 4.26-4.19 (m, 4H), 2.82 (t, 2H), 2.74 (t, 2H), 2.00 (s, 6H), 1.85 (t, 2H) 1.75-1.71 (m, 12H), 1.52 (m, 2H), 1.04 (m, 3H) |
| Synthesis Example 16 (CD$_3$OD) | 8.31 (d, 2H), 7.92 (d, 2H), 7.82 (s, 2H), 7.59-7.51 (m, 4H), 7.42 (d, 2H), 7.37 (d, 2H) 7.26-7.18 (m, 4H), 7.02-6.94 (m, 4H), 6.39 (d, 2H), 4.86 (s, 4H), 4.41 (t, 4H), 3.81 (t, 4H), 2.19 (t, 4H), 2.17 (t, 4H), 1.64-1.50 (m, 26H), 0.97 (s, 12H) |
| Synthesis Example 17 (CD$_3$OD) | 8.53 (s, 1H), 8.25 (d, 2H), 8.09-8.01 (m, 4H), 7.75-7.78 (m, 2H), 7.70-7.64 (m, 6H), 7.58-7.51 (m, 6H), 7.24 (d, 1H), 6.61 (d, 1H), 6.34 (d, 1H), 5.91 (s, 1H), 4.66-4.58 (m, 4H), 4.38 (t, 2H), 4.06 (q, 2H), 3.94 (s, 3H), 2.80-2.75 (m, 6H), 1.87 (s, 12H), 1.28 (s, 6H), 1.17 (t, 3H) |
| Synthesis Example 18 (CDCl$_3$) | 7.94 (d, 1H), 7.55 (d, 1H), 7.48-7.38 (m, 3H), 7.11 (d, 1H), 6.87 (d, 1H), 5.28 (d, 1H), 4.93 (s, 2H), 3.83 (s, 2H), 3.76 (t, 2H), 3.02 (s, 2H), 1.75-1.60 (m, 9H), 1.32 (s, 6H), 1.07 (d, 6H) |
| Synthesis Example 19 (CDCl$_3$) | 8.37 (s, 1H), 8.27 (s, 1H), 8.20 (s, 1H), 7.93 (d, 2H), 7.70 (d, 1H), 7.62 (d, 2H), 6.69 (d, 2H), 5.08 (t, 2H), 4.06 (q, 2H), 3.46 (q, 4H), 3.14 (t, 2H), 3.10 (s, 3H), 1.62 (s, 6H), 1.26-1.19 (m, 9H) |
| Synthesis Example 20 (CDCl$_3$) | 10.43 (s, 1H), 8.14 (s, 1H), 7.90 (d, 1H), 7.73 (m, 2H), 7.51 (d, 2H), 7.05 (m, 2H), 6.82 (m, 2H), 5.22 (s, 2H), 4.04 (q, 2H), 3.75 (m, 4H), 3.14 (t, 2H), 2.99 (s, 3H), 1.63 (s, 6H), 1.47-1.44 (m, 9H), 1.19 (t, 3H), 1.05 (s, 6H) |

TABLE 3

| | |
|---|---|
| Synthesis Example 21 (DMSO-d6) | 7.74 (d, 2H), 7.44-7.39 (m, 2H), 7.28-7.24 (m, 2H), 7.09-7.01 (m, 3H), 6.59 (d, 1H), 5.42 (d, 2H), 4.20-4.14 (m, 4H), 3.98 (q, 2H), 2.69-2.66 (m, 5H), 1.56-1.50 (m, 14H), 1.10-1.04 (m, 5H), 0.87 (t, 3H) |
| Synthesis Example 22 (CDCl$_3$) | 8.11 (s, 1H), 8.09 (d, 1H), 7.65-7.57 (m, 2H), 7.48-7.36 (m, 4H), 7.15-7.08 (m, 2H), 6.86-6.84 (m, 2H), 5.11 (s, 2H), 4.02 (q, 2H), 3.75 (m, 4H), 2.63 (s, 2H), 2.45 (t, 2H), 1.73-1.52 (m, 12H), 1.22-1.12 (m, 6H), 1.06-0.90 (m, 6H) |
| Synthesis Example 23 (CDCl$_3$) | 7.63 (d, 1H), 7.53 (s,1H), 7.41 (d, 2H), 7.19 (d, 1H), 6.63 (d, 2H), 6.54 (d, 1H), 6.25 (d, 1H), 4.09 (t, 4H), 3.9-3.83 (m, 5H), 3.4-3.32 (m, 8H), 2.56 (t, 2H), 1.22-1.14 (m, 9H) |
| Synthesis Example 24 (CD$_3$OD) | 7.83 (d, 1H), 7.65-7.10 (m, 6H), 6.93 (t, 1H), 6.65-6.40 (m, 3H), 4.10 (m, 2H), 3.90 (t, 2H), 3.10-2.97 (m, 9H), 2.27 (t, 2H), 1.38-1.20 (m, 9H) |
| Synthesis Example 25 (DMSO-d6) | 10.75 (s, 1H), 7.90 (d, 2H), 7.83-7.73 (m, 5H), 7.47 (m, 3H), 7.22 (d, 1H), 7.07 (d, 2H), 6.81 (d, 2H), 3.88 (s, 3H), 3.07 (s, 6H), 2.66 (s, 3H), 2.27 (s, 3H), 1.43 (s, 6H) |
| Synthesis Example 26 (DMSO-d6) | 10.29 (s, 1H), 7.88 (d, 2H), 7.78-7.72 (m, 8H), 6.92 (d, 2H), 6.83-6.80 (m, 4H), 3.86 (s, 3H), 3.61 (d, 1H), 3.53 (d, 1H), 3.03 (s, 6H), 2.96 (s, 3H), 1.67 (s, 3H) |
| Synthesis Example 27 (DMSO-d6) | 10.81 (s, 1H), 8.13 (s, 1H), 7.92 (d, 1H), 7.75 (d, 1H), 7.73 (d, 1H), 7.48 (d, 1H), 7.21 (d, 1H), 6.97 (d, 1H), 4.64 (t, 2H), 4.05 (q, 2H), 3.05 (t, 2H), 2.82 (s, 3H), 1.52 (s, 6H), 1.15 (t, 3H) |
| Synthesis Example 28 (DMSO-d6) | 11.03 (s, 1H), 8.05 (s, 1H), 7.96 (d, 1H), 7.87 (s, 1H), 7.67-7.62 (m, 3H), 7.42 (d, 2H), 4.99 (s, 2H), 4.64 (t, 2H), 4.09-4.03 (m, 4H), 3.04 (t, 2H), 2.82 (s, 3H), 2.50 (d, 2H), 1.90 (sep, 1H), 1.49 (s, 6H), 1.83-1.65 (m, 6H), 0.89 (d, 6H) |
| Synthesis Example 29 (CDCl$_3$) | 9.08 (s, 1H), 7.95 (d, 2H), 7.65-7.57 (m, 4H), 7.51-7.43 (m, 4H), 7.37-7.31 (m, 3H), 6.34 (d, 1H), 4.67 (t, 3H), 4.06 (q, 2H) 3.79 (t, 2H), 3.71 (t, 2H), 3.11 (t, 2H), 2.88 (s, 3H), 2.51 (t, 2H), 2.09 (s, 6H), 1.19 (s, 6H), 1.18 (t, 3H) |

TABLE 4

| Synthesis Example | Yield/% | λmax MeOH/nm |
|---|---|---|
| 1 | 29 | 582 |
| 2 | 27 | 648 |
| 3 | 1 | 590 |
| 4 | 16 | 654 |
| 5 | 5 | 584 |
| 6 | 8 | 650 |
| 7 | 2 | 582 |
| 8 | 3 | 587 |
| 9 | 6 | 592, |
| 10 | 1 | 588 |
| 11 | 2 | 578 |
| 12 | 6 | 639 |
| 13 | 6 | 656 |
| 14 | 3 | 650 |
| 15 | 1 | 650 |
| 16 | 6 | 649 |
| 17 | 22 | 650 |
| 18 | 35 | — |
| 19 | 63 | — |
| 20 | 26 | — |
| 21 | 47 | — |
| 22 | 5 | — |
| 26 | 52 | — |
| 27 | 33 | — |
| 28 | 10 | — |
| 29 | 48 | — |

It was confirmed that compounds having structures of dyes (1) to (17) and intermediates (a-1) to (a-12) were synthesized in Synthesis Examples 1 to 29, respectively, as shown in Tables 1 to 3 and Table 4.

Next, the dye-sensitized solar cells 100 described in the above embodiments were produced by the following procedures.

Example 1

By using dye (1) obtained in Synthesis Example 1, a dye-sensitized solar cell 100 equivalent to that described in the above embodiments was produced by the following procedure.

First, a working electrode 11 was produced by the following procedure.

First, as a base 12 having a conductive surface 12a, a conductive glass substrate (F—SnO$_2$) having a transparent conductive film of fluorine-doped SnO and having a size of 2.0 cm in length×1.5 cm in width×1.1 mm in thickness was prepared. Next, masking tape having a thickness of 70 μm was placed on the conductive surface 12a so as to surround a square portion having a size of 0.5 cm in length×0.5 cm in width, and then, 3 cm$^3$ of a metal oxide slurry was applied on the portion with a constant thickness and dried. As the metal oxide slurry, one prepared by suspending a zinc oxide powder (average particle size 20 nm; FINEX-50 manufactured by Sakai Chemical Industry Co., Ltd.) in water so that the amount of the zinc oxide powder was 10% by weight was used, the water having one drop of a non-ionic surfactant, Triton X-100 (Triton is registered trademark), added therein. Next, the masking tape on the conductive surface 12a was peeled off, and then, the base 12 was burned at 450° C. using an electric furnace, thus forming a zinc oxide film having a thickness of about 5 μm serving as a metal oxide layer 13. Next, a dye-containing solution was prepared by dissolving dye (1) and deoxycholic acid in dehydrated ethanol so that their concentrations were $3 \times 10^{-4}$ mol/dm$^3$ and $1 \times 10^{-2}$ mol/dm$^3$, respectively. Then, the base 12 having the metal oxide layer 13 formed thereon was immersed in the dye-containing solution to allow dye (1) to be supported on the metal oxide layer 13 to form a dye-supported metal oxide electrode 14, and thus, a working electrode 11 of Example 1 was obtained.

Next, a counter electrode 21 was produced by the following procedure.

First, as a base 22 having a conductive surface 22a, a conductive glass substrate (F—SnO$_2$) having a transparent conductive film of fluorine-doped SnO and having a size of 2.0 cm in length×1.5 cm in width×1.1 mm in thickness was prepared. Next, a Pt layer having a thickness of 100 nm was formed on the conductive surface 22a by sputtering, and thus, a counter electrode 21 was obtained. It is noted that, in this case, two holes (ϕ1 mm) for injecting an electrolyte solution were preliminarily formed in the base 22 having the conductive surface 22a.

Next, the electrolyte solution was prepared by adding dimethylhexyl imidazolium iodide (0.6 mol/dm$^3$), lithium iodide (0.1 mol/dm$^3$), and iodine (0.05 mol/dm$^3$) to acetonitrile at the prescribed concentrations and performing mixing.

After that, the dye-sensitized solar cell 100 was produced by using the working electrode 11, the counter electrode 21, and the electrolyte solution by the following procedure.

First, spacers having a thickness of 50 μm were placed so as to surround the metal oxide layer 13, and after that, the dye-supported metal oxide electrode 14 of the working electrode 11 and the Pt layer of the counter electrode 21 were placed with facing each other, and bonded via the spacers. After that, the electrolyte solution was injected through the injecting holes formed in the counter electrode 21, to form an electrolyte 31. Finally, all around the cell and the injecting holes were sealed, and thus, the dye-sensitized solar cell 100 of Example 1 was obtained.

Example 2

A working electrode 11 and a dye-sensitized solar cell 100 of Example 2 were produced by the same process as that in Example 1 except that a metal oxide slurry containing a titanium oxide (TiO$_2$) powder described below was used instead of the metal oxide slurry containing a zinc oxide powder, Triton X-100, and water, to form a titanium oxide film, in the formation of the metal oxide layer 13 by burning.

The metal oxide slurry containing a titanium oxide powder was prepared as follows. First, 125 cm$^3$ of titanium isopropoxide was added to 750 cm$^3$ of 0.1 mol/dm$^3$ nitric acid aqueous solution with performing stirring, and stirring was carried out vigorously at 80° C. for 8 hours. The resulting liquid was poured into a teflon (registered trademark) pressure container, and the pressure container was treated in an autoclave at 230° C. for 16 hours. After that, the liquid (sol liquid) after the autoclave treatment containing precipitates was stirred to be resuspended. Next, the resulting suspension was filtered under vacuum to remove non-resuspended precipitates, and sol filtrate was concentrated so as to have a titanium oxide concentration of 11% by mass using an evaporator. After that, in order to improve wettability of the concentrated solution to the substrate, a drop of Triton X-100 was added. Next, a titanium oxide powder having an average particle size of 30 nm (P-25 manufactured by Nippon Aerosil Co., Ltd.) was added to the concentrated solution so that the entire content of titanium oxide was 33% by mass, and dispersed for 1 hour by centrifugal mixing using rotation and revolution, thus preparing the metal oxide slurry containing the titanium oxide powder.

Examples 3 and 4

Working electrodes 11 and dye-sensitized solar cells 100 of Examples 3 and 4 were obtained by the same process as those in Examples 1 and 2 except that dye (5) was used instead of dye (1), respectively.

Examples 5 and 6

Working electrodes 11 and dye-sensitized solar cells 100 of Examples 5 and 6 were obtained by the same process as those in Examples 1 and 2 except that dye (8) was used instead of dye (1), respectively.

Examples 7 and 8

Working electrodes 11 and dye-sensitized solar cells 100 of Examples 7 and 8 were obtained by the same process as those in Examples 1 and 2 except that dye (3) was used instead of dye (1), respectively.

Examples 9 and 10

Working electrodes 11 and dye-sensitized solar cells 100 of Examples 9 and 10 were obtained by the same process as those in Examples 1 and 2 except that dye (9) was used instead of dye (1), respectively.

Examples 11 and 12

Working electrodes 11 and dye-sensitized solar cells 100 of Examples 11 and 12 were obtained by the same process as those in Examples 1 and 2 except that dye (10) was used instead of dye (1), respectively.

Examples 13 and 14

Working electrodes 11 and dye-sensitized solar cells 100 of Examples 13 and 14 were obtained by the same process as those in Examples 1 and 2 except that dye (2) was used instead of dye (1), respectively.

Examples 15 and 16

Working electrodes 11 and dye-sensitized solar cells 100 of Examples 15 and 16 were obtained by the same process as those in Examples 1 and 2 except that dye (6) was used instead of dye (1), respectively.

Examples 17 and 18

Working electrodes 11 and dye-sensitized solar cells 100 of Examples 17 and 18 were obtained by the same process as those in Examples 1 and 2 except that dye (14) was used instead of dye (1), respectively.

Examples 19 and 20

Working electrodes 11 and dye-sensitized solar cells 100 of Examples 19 and 20 were obtained by the same process as those in Examples 1 and 2 except that dye (16) was used instead of dye (1), respectively.

Examples 21 and 22

Working electrodes 11 and dye-sensitized solar cells 100 of Examples 21 and 22 were obtained by the same process as those in Examples 1 and 2 except that dye (4) was used instead of dye (1), respectively.

Examples 23 and 24

Working electrodes 11 and dye-sensitized solar cells 100 of Examples 23 and 24 were obtained by the same process as those in Examples 1 and 2 except that dye (13) was used instead of dye (1), respectively.

Examples 25 and 26

Working electrodes 11 and dye-sensitized solar cells 100 of Examples 25 and 26 were obtained by the same process as those in Examples 1 and 2 except that dye (17) was used instead of dye (1), respectively.

Comparative Examples 1 and 2

Working electrodes 11 and dye-sensitized solar cells 100 of Comparative Examples 1 and 2 were obtained by the same process as those in Examples 1 and 2 except that $3.0 \times 10^{-4}$ mol/dm$^3$ of dye (C1) and $3.0 \times 10^{-4}$ mol/dm$^3$ of dye (C2) were used instead of dye (1), respectively.

Comparative Examples 3 and 4

Working electrodes 11 and dye-sensitized solar cells 100 of Comparative Examples 3 and 4 were obtained by the same process as those in Examples 3 and 4 except that $3.0 \times 10^{-4}$ mol/dm$^3$ of a dye (C3) and $3.0 \times 10^{-4}$ mol/dm$^3$ of a dye (C4) were used instead of dye (5), respectively.

Comparative Examples 5 and 6

Working electrodes 11 and dye-sensitized solar cells 100 of Comparative Examples 5 and 6 were obtained by the same process as those in Examples 5 and 6 except that $3.0 \times 10^{-4}$ mol/dm$^3$ of a dye (C3) and $3.0 \times 10^{-4}$ mol/dm$^3$ of a dye (C2) were used instead of dye (8), respectively.

Comparative Examples 7 and 8

Working electrodes 11 and dye-sensitized solar cells 100 of Comparative Examples 7 and 8 were obtained by the same process as those in Examples 19 and 20 except that $3.0 \times 10^{-4}$ mol/dm$^3$ of dye (C5) was used instead of dye (16), respectively.

Comparative Examples 9 and 10

Working electrodes 11 and dye-sensitized solar cells 100 of Comparative Examples 9 and 10 were obtained by the same process as those in Examples 7 and 8 except that $3.0 \times 10^{-4}$ mol/dm$^3$ of a dye (C6) and $3.0 \times 10^{-4}$ mol/dm$^3$ of a dye (C4) were used instead of dye (3), respectively.

Comparative Examples 11 and 12

Working electrodes 11 and dye-sensitized solar cells 100 of Comparative Examples 11 and 12 were obtained by the same process as those in Examples 11 and 12 except that $3.0 \times 10^{-4}$ mol/dm³ of a dye (C8) and 3.0×10⁻⁴ mol/dm³ of a dye (C4) were used instead of dye (10), respectively.

Comparative Examples 13 and 14

Working electrodes 11 and dye-sensitized solar cells 100 of Comparative Examples 13 and 14 were obtained by the same process as those in Examples 13 and 14 except that 3.0×10⁻⁴ mol/dm³ of dye (C1) and 3.0×10⁻⁴ mol/dm³ of dye (C8) were used instead of dye (2), respectively.

Comparative Examples 15 and 16

Working electrodes 11 and dye-sensitized solar cells 100 of Comparative Examples 15 and 16 were obtained by the same process as those in Examples 15 and 16 except that 3.0×10⁻⁴ mol/dm³ of a dye (C9) was used instead of dye (6), respectively.

Comparative Examples 17 and 18

Working electrodes 11 and dye-sensitized solar cells 100 of Comparative Examples 17 and 18 were obtained by the same process as those in Examples 17 and 18 except that 3.0×10⁻⁴ mol/dm³ of a dye (C10) was used instead of dye (14), respectively.

Comparative Examples 19 and 20

Working electrodes 11 and dye-sensitized solar cells 100 of Comparative Examples 19 and 20 were obtained by the same process as those in Examples 19 and 20 except that 3.0×10⁻⁴ mol/dm³ of a dye (C10) and 6.0×10⁻⁴ mol/dm³ of a dye (C3) were used instead of dye (16), respectively.

Comparative Examples 21 and 22

Working electrodes 11 and dye-sensitized solar cells 100 of Comparative Examples 21 and 22 were obtained by the same process as those in Examples 21 and 22 except that 3.0×10⁻⁴ mol/dm³ of a dye (C10) and 3.0×10⁻⁴ mol/dm³ of a dye (C6) were used instead of dye (4), respectively.

Comparative Examples 23 and 24

Working electrodes 11 and dye-sensitized solar cells 100 of Comparative Examples 23 and 24 were obtained by the same process as those in Examples 23 and 24 except that 3.0×10⁻⁴ mol/dm³ of a dye (C10) and 3.0×10⁻⁴ mol/dm³ of a dye (C11) were used instead of dye (13), respectively.

Comparative Examples 25 and 26

Working electrodes 11 and dye-sensitized solar cells 100 of Comparative Examples 25 and 26 were obtained by the same process as those in Examples 25 and 26 except that 3.0×10⁻⁴ mol/dm³ of a dye (C10) and 3.0×10⁻⁴ mol/dm³ of a dye (C12) were used instead of dye (17), respectively.

Dyes (C1) to (C12) used in Comparative Examples are shown below.

[Formula 71]

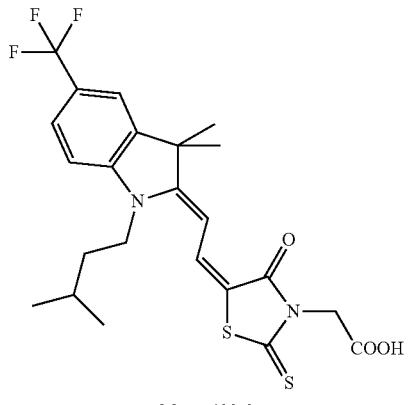

(C1)

Mw = 498.6

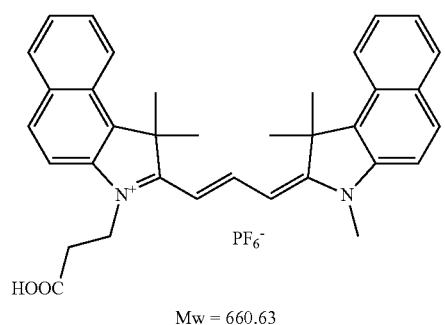

(C2)

Mw = 660.63

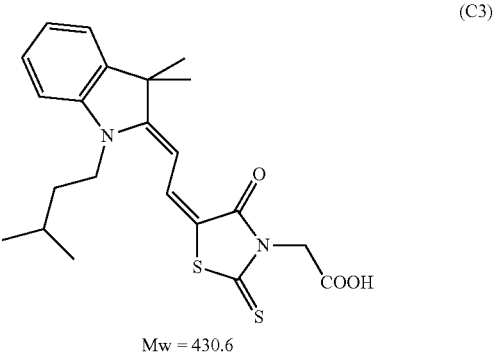

(C3)

Mw = 430.6

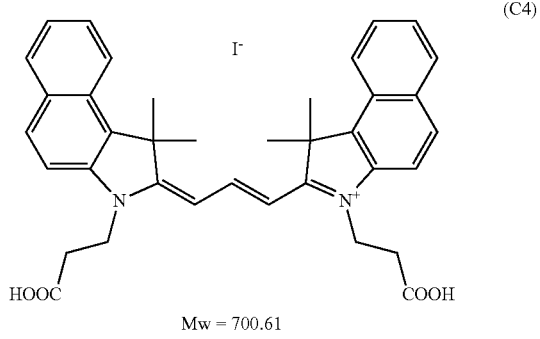

(C4)

Mw = 700.61

-continued

[Formula 72]

(C5)
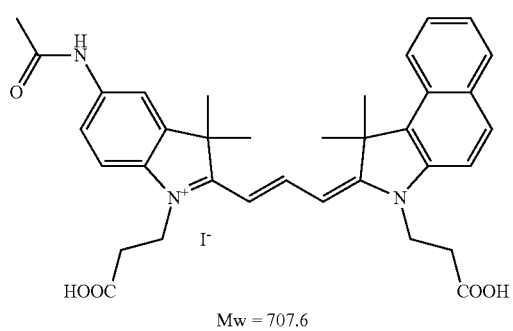
Mw = 707.6

(C6)
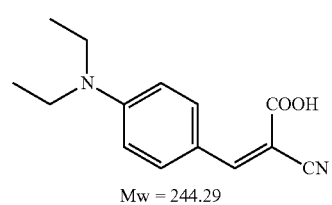
Mw = 244.29

(C7)
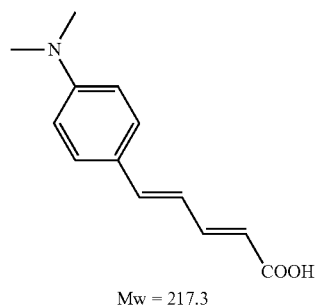
Mw = 217.3

(C8)
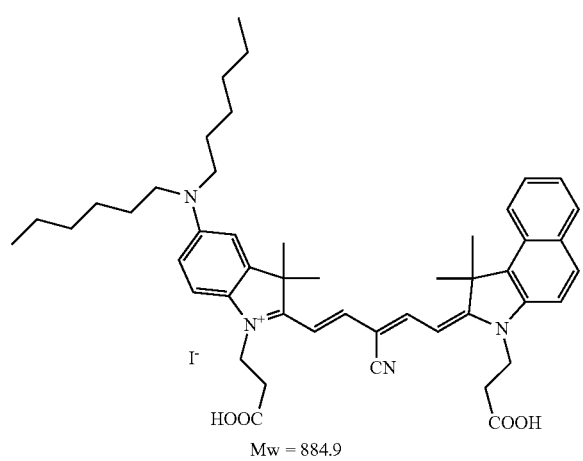
Mw = 884.9

-continued

[Formula 73]

(C9)
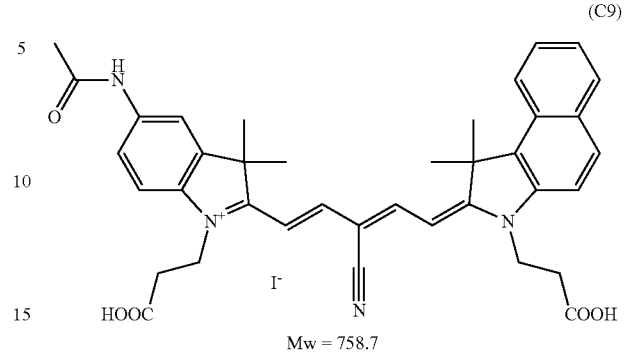
Mw = 758.7

(C10)

(C11)

(C12)
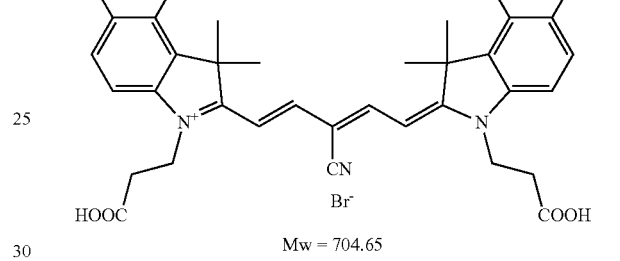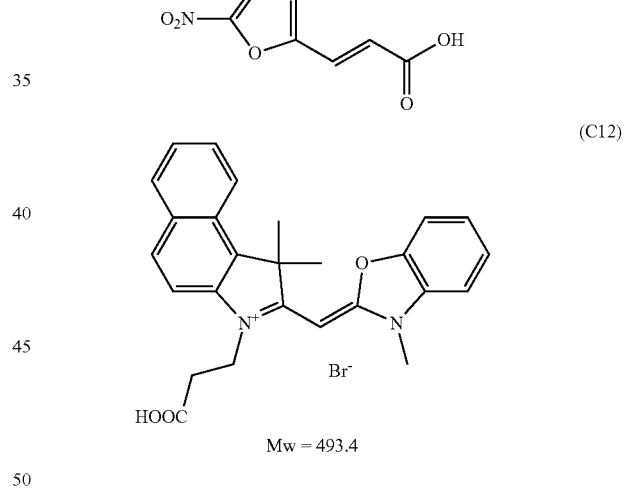
Mw = 704.65

Mw = 493.4

<Measurement of Energy Conversion Efficiency>

Battery properties of the dye-sensitized solar cells 100 obtained in Examples 1 to 26 and Comparative Examples 1 to 26 were measured by using a solar simulator under AM-1.5 (1000 W/m$^2$). The results are shown in Tables 5 and 6.

It is noted that the energy conversion efficiency ($\eta$:%) is a value obtained by sweeping voltage of the dye-sensitized solar cell 100 using a source meter and measuring response current, and then, calculating a value of a maximum output divided by light intensity per 1 cm$^2$, the maximum output being the product of the voltage and the current, and multiplying the calculated value by 100 to represent the value by percent. That is, the energy conversion efficiency ($\eta$:%) is represented by (maximum output/light intensity per 1 cm$^2$)× 100.

<Peeling Test>

For evaluating the adsorptive properties (adhesion) of the dye, a peeling test was performed. The results are shown in Tables 5 and 6.

The peeling test was performed by the following procedure. First, for each of the working electrodes 11, an absorption spectrum of a surface of the dye-supported metal oxide layer 14 was measured using a UV spectrometer (measured wavelength was in the range of 350 nm to 950 nm), and initial absorbance at peak wavelength was obtained. Next, the working electrode 11 was immersed into 100 cm$^3$ of acetonitrile mixture containing 10% by weight of water for 2 hours, and then, measurement of absorption spectrum was performed by the same manner and absorbance at peak wavelength after immersed in 10 wt % water-containing acetonitrile for 2 hours was obtained. Finally, based on the initial absorbance and the absorbance after immersed in 10 wt % water-containing acetonitrile for 2 hours at peak wavelength, dye residual rate (%)=(absorbance after immersed in 10 wt % water-containing acetonitrile for 2 hours/initial absorbance)×100 was calculated. It is noted that the series of measurement of absorption spectrum were carried out using UV-3101PC manufactured by SHIMADZU CORPORATION with 5 nm of slit width.

TABLE 5

| | Dye | Metal oxide layer | Conversion efficiency | Peeling test |
|---|---|---|---|---|
| Example 1 | Dye (1) | ZnO | 2.63 | 22% |
| Example 2 | | TiO$_2$ | 1.55 | 25% |
| Example 3 | Dye (5) | ZnO | 3.22 | 90% |
| Example 4 | | TiO$_2$ | 1.97 | 83% |
| Example 5 | Dye (8) | ZnO | 1.75 | 26% |
| Example 6 | | TiO$_2$ | 1.35 | 23% |
| Example 7 | Dye (3) | ZnO | 2.75 | 90% |
| Example 8 | | TiO$_2$ | 1.77 | 91% |
| Example 9 | Dye (9) | ZnO | 3.52 | 90% |
| Example 10 | | TiO$_2$ | 2.11 | 88% |
| Example 11 | Dye (10) | ZnO | 3.84 | 89% |
| Example 12 | | TiO$_2$ | 1.94 | 84% |
| Comparative Example 1 | Dye (C1) Dye (C2) | ZnO | 1.14 | 18% |
| Comparative Example 2 | | TiO$_2$ | 0.97 | 13% |
| Comparative Example 3 | Dye (C3) Dye (C4) | ZnO | 1.37 | 80% |
| Comparative Example 4 | | TiO$_2$ | 1.05 | 73% |
| Comparative Example 5 | Dye (C3) Dye (C2) | ZnO | 1.25 | 15% |
| Comparative Example 6 | | TiO$_2$ | 1.11 | 17% |
| Comparative Example 7 | Dye (C5) | ZnO | 1.15 | 65% |
| Comparative Example 8 | | TiO$_2$ | 1.01 | 67% |
| Comparative Example 9 | Dye (C6) Dye (C4) | ZnO | 1.31 | 83% |
| Comparative Example 10 | | TiO$_2$ | 1.23 | 85% |
| Comparative Example 11 | Dye (C8) Dye (C4) | ZnO | 1.32 | 82% |
| Comparative Example 12 | | TiO$_2$ | 1.00 | 80% |

Table 5 reveals that the dye-sensitized solar cells 100 of Examples 1 and 2 have higher energy conversion efficiencies and higher dye residual rates than the dye-sensitized solar cells 100 of Comparative Examples 1 and 2. This indicates that, in the case of simply mixing the two types of dyes, adsorption sites of the metal oxide (sites to which the dye can be adsorbed) are shared between the 2 types of dyes, which results in decreased adsorption amounts. Moreover, it is indicated that balance control of the adsorption amounts are significantly difficult because the two types of dyes have different adsorption strengths, and therefore, a high conversion efficiency cannot be obtained. Furthermore, it is indicated that the dyes cannot withstand the peeling test because the dyes each have only one carboxylic acid.

Table 5 reveals that the dye-sensitized solar cells 100 of Examples 3 and 4 have higher energy conversion efficiencies and higher dye residual rates than the dye-sensitized solar cells 100 of Comparative Examples 3 and 4. This indicates that the dyes cannot withstand the peeling test because one dye has only one carboxylic acid and therefore is very liable to be peeled off.

Table 5 reveals that the dye-sensitized solar cells 100 of Examples 5 and 6 have higher energy conversion efficiencies and higher dye residual rates than the dye-sensitized solar cells 100 of Comparative Examples 5 and 6.

Table 5 reveals that the dye-sensitized solar cells 100 of Examples 7 and 8 have higher energy conversion efficiencies and higher dye residual rates than the dye-sensitized solar cells 100 of Comparative Examples 7 and 8. This indicates that, in the case of using dye (C5) in which a methyl group is introduced instead of the yellow unit A, high values can be obtained neither in the conversion efficiency measurement nor in the peeling test.

Table 5 reveals that the dye-sensitized solar cells 100 of Examples 9 and 10 have higher energy conversion efficiencies and higher dye residual rates than the dye-sensitized solar cells 100 of Comparative Examples 9 and 10.

Table 5 reveals that the dye-sensitized solar cells 100 of Examples 11 and 12 have higher energy conversion efficiencies and higher dye residual rates than the dye-sensitized solar cells 100 of Comparative Examples 11 and 12.

TABLE 6

| | Dye | Metal oxide layer | Conversion efficiency | Peeling test |
|---|---|---|---|---|
| Example 13 | Dye (2) | ZnO | 1.65 | 23% |
| Example 14 | | TiO$_2$ | 1.52 | 27% |
| Example 15 | Dye (6) | ZnO | 1.79 | 71% |
| Example 16 | | TiO$_2$ | 1.51 | 65% |
| Example 17 | Dye (14) | ZnO | 1.67 | 77% |
| Example 18 | | TiO$_2$ | 1.49 | 72% |
| Example 19 | Dye (16) | ZnO | 1.55 | 66% |
| Example 20 | | TiO$_2$ | 1.55 | 66% |
| Example 21 | Dye (4) | ZnO | 1.79 | 90% |
| Example 22 | | TiO$_2$ | 1.58 | 83% |
| Example 23 | Dye (13) | ZnO | 1.58 | 89% |
| Example 24 | | TiO$_2$ | 1.51 | 85% |
| Example 25 | Dye (17) | ZnO | 1.61 | 33% |
| Example 26 | | TiO$_2$ | 1.52 | 31% |
| Comparative Example 13 | Dye (C1) Dye (C8) | ZnO | 0.56 | 55% |
| Comparative Example 14 | | TiO$_2$ | 0.33 | 60% |
| Comparative Example 15 | Dye (C9) | ZnO | 0.30 | 39% |
| Comparative Example 16 | | TiO$_2$ | 0.28 | 33% |
| Comparative Example 17 | Dye (C10) | ZnO | 0.37 | 68% |
| Comparative Example 18 | | TiO$_2$ | 0.31 | 58% |
| Comparative Example 19 | Dye (C10) Dye (C3) | ZnO | 0.45 | 61% |
| Comparative Example 20 | | TiO$_2$ | 0.40 | 52% |
| Comparative Example 21 | Dye (C10) Dye (C6) | ZnO | 0.61 | 59% |

TABLE 6-continued

| Dye | | Metal oxide layer | Conversion efficiency | Peeling test |
|---|---|---|---|---|
| Comparative Example 22 | | TiO$_2$ | 0.34 | 53% |
| Comparative Example 23 | Dye (C10) | ZnO | 0.51 | 51% |
| Comparative Example 24 | Dye (C11) | TiO$_2$ | 0.27 | 44% |
| Comparative Example 25 | Dye (C10) Dye (C12) | ZnO | 0.47 | 52% |
| Comparative Example 26 | | TiO$_2$ | 0.25 | 49% |

Table 6 reveals that the dye-sensitized solar cells 100 of Examples 13 and 14 have higher energy conversion efficiencies than the dye-sensitized solar cells 100 of Comparative Examples 13 and 14. Especially, it is confirmed that the dye-sensitized solar cells 100 of Comparative Examples 13 and 14 have extremely low photoelectric conversion efficiencies and have little practicability.

Table 6 reveals that the dye-sensitized solar cells 100 of Examples 15 and 16 have higher energy conversion efficiencies and higher dye residual rates than the dye-sensitized solar cells 100 of Comparative Examples 15 and 16. On the other hand, in the case of using dye (C9) in which a methyl group is introduced instead of the yellow unit A, high values can be obtained neither in the conversion efficiency measurement nor in the peeling test. Especially, it is confirmed that the dye-sensitized solar cells 100 of Comparative Examples 15 and 16 have extremely low photoelectric conversion efficiencies and have little practicability.

Table 6 reveals that the dye-sensitized solar cells 100 of Examples 17 and 18 have higher energy conversion efficiencies and higher dye residual rates than the dye-sensitized solar cells 100 of Comparative Examples 17 and 18. On the other hand, in the case of using dye (C10) not including an amide bond as a linking group, a high conversion efficiency cannot be obtained. Especially, it is confirmed that the dye-sensitized solar cells 100 of Comparative Examples 17 and 18 have extremely low photoelectric conversion efficiencies and have little practicability.

Table 6 reveals that the dye-sensitized solar cells 100 of Examples 19 and 20 have higher energy conversion efficiencies and higher dye residual rates than the dye-sensitized solar cells 100 of Comparative Examples 19 and 20.

Table 6 reveals that the dye-sensitized solar cells 100 of Examples 21 and 22 have higher energy conversion efficiencies and higher dye residual rates than the dye-sensitized solar cells 100 of Comparative Examples 21 and 22.

Table 6 reveals that the dye-sensitized solar cells 100 of Examples 23 and 24 have higher energy conversion efficiencies and higher dye residual rates than the dye-sensitized solar cells 100 of Comparative Examples 23 and 24.

Table 6 reveals that the dye-sensitized solar cells 100 of Examples 25 and 26 have higher energy conversion efficiencies and higher dye residual rates than the dye-sensitized solar cells 100 of Comparative Examples 25 and 26.

Moreover, the above results reveal that the (combined) dyes used in Examples 1 to 26, in which a structure having a maximum absorption wavelength λmax of 350 to 500 nm in a methanol solution and a cyanine skeleton having a maximum absorption wavelength λmax of 500 to 700 nm in a methanol solution are bonded via a linking group, have higher dye residual rates and are excellent in energy conversion efficiency in comparison with the cases of using the (uncombined) dyes in combination. These facts indicates that, in the case of the (combined) dye having such structure, adsorption to the surface of the metal oxide is promoted, and/or, the adsorption condition of the dye is such that the dye is hard to peel off, which results from steric hindrance of the dye structure, and also indicates that electron injection properties to the metal oxide (semiconductor material) are improved.

Furthermore, the above results reveal that the (combined) dye having such structure exhibit comparable dye residual rate but significantly excellent energy conversion efficiency in the case of the dye-sensitized solar cell 100 having the metal oxide layer 13 substantially composed of zinc oxide in comparison with the case of the dye-sensitized solar cell 100 having the metal oxide layer 13 substantially composed of titanium oxide.

<Measurement of Ultraviolet-Visible Absorption Spectrum>

An Ultraviolet-visible absorption spectrum was measured for dye (5), dye (C3), dye (C4), and a mixture of dye (C3) and dye (C4) at a ratio of 1:1. The measurement was performed by using a UV spectrometer (U-3010) manufactured by Hitachi, Ltd., and using a sample prepared by adding each of the dyes to methanol (CH$_3$OH; solvent) so that the absorbance is in the range of 0.5 to 1.0. The results are shown in FIGS. 3 to 6.

It should be noted that the present invention is in no way limited to the above described embodiments and Examples, but various modifications may be arbitrarily made within the spirit of the present invention, as described above.

INDUSTRIAL APPLICABILITY

As described above, the present invention can be widely and effectively utilized in electronic and electric materials associated with photoelectric conversion devices such as dye-sensitized solar cells; electronic and electric devices; and equipment, facilities, systems, and the like provided with the materials or the devices.

REFERENCE SIGNS LIST

11 . . . working electrode, 12 . . . substrate, 12$a$ . . . conductive surface, 13 . . . metal oxide layer, 14 . . . dye-supported metal oxide electrode, 21 . . . counter electrode, 22$a$ . . . conductive surface, 22 . . . substrate, 31 . . . electrolyte, 41 . . . spacer, 100 . . . photoelectric conversion device.

The invention claimed is:

1. A photoelectric conversion device dye, the dye being a compound of the structure represented by the following general formula (I):

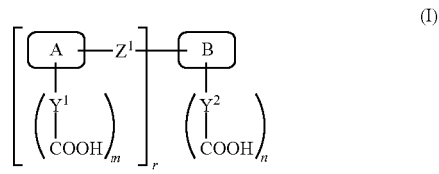

wherein:

A is selected from the group consisting of the following formulas (IV) to (VII):

109

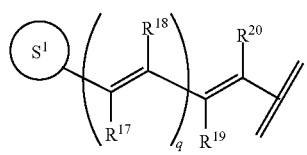
(IV)

wherein:
S¹ is an aromatic ring which may have a substituent, or a heterocyclic ring which may have a substituent;
$R^{17}$ to $R^{20}$ are each independently a hydrogen atom, an alkyl group having 1 to 8 carbon atoms, a halogen atom, or a cyano group;
q is 0 or 1, and the substituent —Y¹—COOH substitutes S¹;

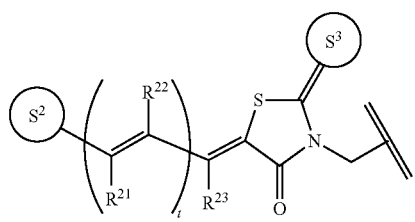
(V)

wherein:
S² is an aromatic ring which may have a substituent, or a heterocyclic ring which may have a substituent;
S³ is a sulfur atom or a structure represented by the following formula (Va);
$R^{21}$ to $R^{23}$ are each independently a hydrogen atom, an alkyl group having 1 to 8 carbon atoms, a halogen atom, or a cyano group;
$R^{24}$ is a hydrogen atom, an alkyl group having 1 to 20 carbon atoms, an aryl group having 6 to 30 carbon atoms, an arylalkyl group having 7 to 30 carbon atoms, or an anchor group;
u is 0 or 1; and
the substituent —Y¹—COOH substitutes S² and/or S³:

(Va)

(VI)

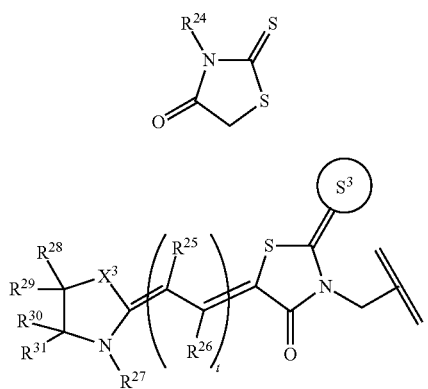

110 wherein:
$R^{25}$ to $R^{26}$ are each independently a hydrogen atom, an alkyl group having 1 to 8 carbon atoms, a halogen atom, or a cyano group;
$R^{27}$ is a hydrogen atom, an alkyl group having 1 to 20 carbon atoms, an aryl group having 6 to 30 carbon atoms, an arylalkyl group having 7 to 30 carbon atoms, or an anchor group;
$R^{28}$ to $R^{31}$ are each independently a hydrogen atom, a halogen atom, an alkyl group having 1 to 20 carbon atoms, or an aryl group having 6 to 12 carbon atoms, where $R^{28}$ and $R^{30}$ may each be eliminated to form an unsaturated bond, or $R^{29}$ and $R^{31}$ may be linked to form a benzene ring which may have a substituent, a naphthalene ring which may have a substituent, or a phenanthrene ring which may have a substituent;
t is 0 or 1; and
the substituent —Y¹—COOH substitutes S³; and

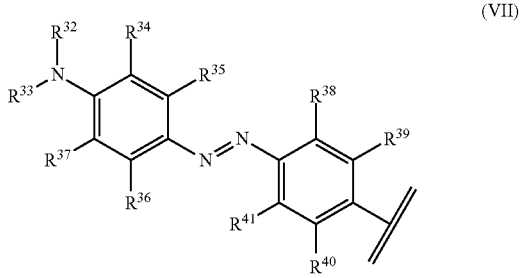
(VII)

wherein:
$R^{32}$ to $R^{33}$ are each independently a hydrogen atom, an alkyl group having 1 to 20 carbon atoms, or an arylalkyl group having 7 to 30 carbon atoms; and
$R^{34}$ to $R^{41}$ are each independently a hydrogen atom, a halogen atom, a hydroxyl group, a cyano group, a nitro group, an alkyl group having 1 to 20 carbon atoms, an aryl group having 6 to 30 carbon atoms, or an arylalkyl group having 7 to 30 carbon atoms, B comprises a cyanine skeleton having a maximum absorption wavelength λmax of 500 to 700 nm in a methanol solution;

Z¹ is any one divalent linking group selected from —CONR—, —NRCO—, —SO₂NR—, and —NRSO₂—;

R in Z¹ is a hydrogen atom, an alkyl group having 1 to 8 carbon atoms, or an arylalkyl group having 7 to 20 carbon atoms;

Y¹ and Y² are each independently an alkylene group having 1 to 8 carbon atoms, or a single bond;

r is 1 or 2;

m and n are each independently an integer of 0 to 2; and (m+n) is 1 or more.

2. The photoelectric conversion device dye according to claim 1, wherein the dye is a compound of the structure represented by the following general formula (II):

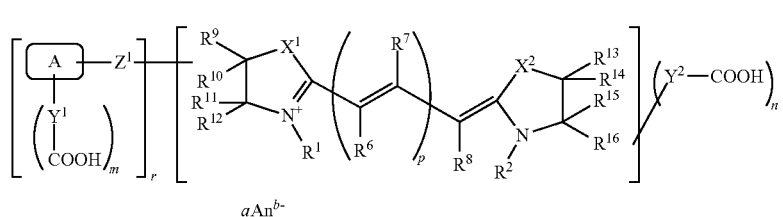

wherein:
X$^1$ and X$^2$ are each independently an oxygen atom, a sulfur atom, a selenium atom, CR$^3$R$^4$, or NR$^5$;
R$^1$ to R$^5$ are each independently a hydrogen atom, an alkyl group having 1 to 20 carbon atoms, an alkenyl group having 2 to 8 carbon atoms, or an alkynyl group having 2 to 8 carbon atoms, where R$^1$ to R$^5$ may each be independently substituted by a halogen atom, a nitro group, a cyano group, an amino group, a hydroxyl group, an ether group, a carbonyl group, an aromatic ring, a heterocyclic ring, or a metallocenyl group, and R$^3$ and R$^4$ may be linked to form an alicyclic group having a 3- to 6-membered ring;
R$^6$ to R$^8$ are each independently a hydrogen atom, an alkyl group having 1 to 8 carbon atoms, an aryl group having 6 to 12 carbon atoms, a halogen atom, or a cyano group;
R$^9$ to R$^{16}$ are each independently a hydrogen atom, a halogen atom, an alkyl group having 1 to 20 carbon atoms, or an aryl group having 6 to 12 carbon atoms;
in R$^9$ to R$^{16}$, R$^9$ and R$^{11}$ may be eliminated or R$^{13}$ and R$^{15}$ may be eliminated to each form an unsaturated bond, or R$^{10}$ and R$^{12}$ may be linked or R$^{14}$ and R$^{16}$ may be linked to each form a benzene ring which may have a substituent, a naphthalene ring which may have a substituent, or a phenanthrene ring which may have a substituent;
p is 1 or 2;
Z$^1$ in the formula replaces R$^1$ to R$^{16}$ or a hydrogen atom contained in R$^1$ to R$^{16}$;
a substituent —Y$^2$—COOH in the formula replaces R$^1$ to R$^{16}$ or a hydrogen atom contained in R$^1$ to R$^{16}$;
An$^{b-}$ is a b-valent anion;
a is 1 or 2, and is a coefficient for keeping a charge of the entire dye neutral;
b is 1 or 2; and
m, n, r, Z$^1$, A, Y$^1$, and Y$^2$ are the same as described in the general formula (I).

3. The photoelectric conversion device dye according to claim 2, wherein the dye is a compound of the structure represented by the following general formula (III):

wherein:
D$^1$ and D$^2$ are each independently a benzene ring which may have a substituent, a naphthalene ring which may have a substituent, or a phenanthrene ring which may have a substituent;
two substituents —Y$^2$—COOH in the formula each replace R$^1$ to R$^8$ or a hydrogen atom contained in R$^1$ to R$^8$, or substitute the benzene ring, the naphthalene ring, or the phenanthrene ring represented by D$^1$ and D$^2$; and
the other variables are the same as described in formula (II).

4. A compound of the structure represented by the following formula (IX):

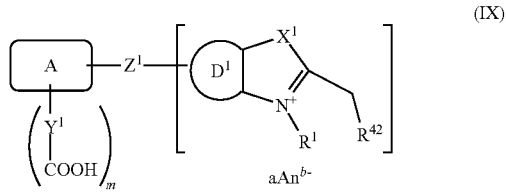

wherein:
A is selected from the group consisting of the following formulas (IV) to (VII):

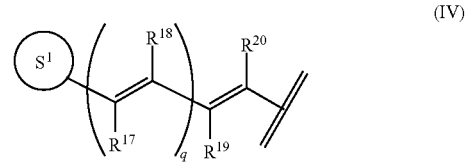

wherein:
S$^1$ is an aromatic ring which may have a substituent, or a heterocyclic ring which may have a substituent;

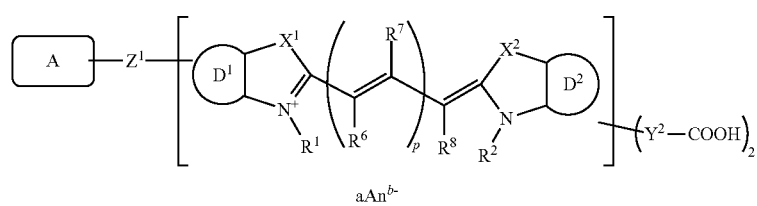

$R^{17}$ to $R^{20}$ are each independently a hydrogen atom, an alkyl group having 1 to 8 carbon atoms, a halogen atom, or a cyano group;

q is 0 or 1, and the substituent —$Y^1$—COOH substitutes $S^1$;

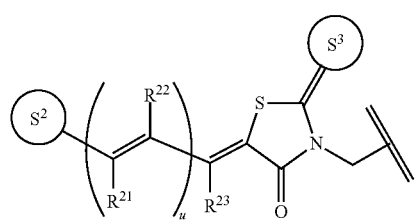

(V)

wherein:
$S^2$ is an aromatic ring which may have a substituent, or a heterocyclic ring which may have a substituent;
$S^3$ is a sulfur atom or a structure represented by the following formula (Va);
$R^{21}$ to $R^{23}$ are each independently a hydrogen atom, an alkyl group having 1 to 8 carbon atoms, a halogen atom, or a cyano group;
$R^{24}$ is a hydrogen atom, an alkyl group having 1 to 20 carbon atoms, an aryl group having 6 to 30 carbon atoms, an arylalkyl group having 7 to 30 carbon atoms, or an anchor group;
u is 0 or 1; and
the substituent —$Y^1$—COOH substitutes $S^2$ and/or $S^3$:

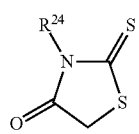

(Va)

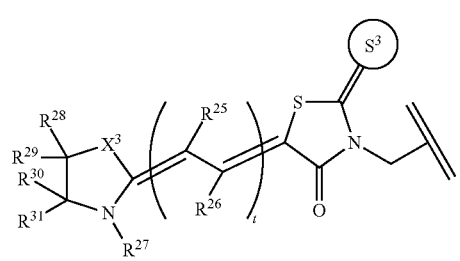

(VI)

wherein:
$R^{25}$ to $R^{26}$ are each independently a hydrogen atom, an alkyl group having 1 to 8 carbon atoms, a halogen atom, or a cyano group;
$R^{27}$ is a hydrogen atom, an alkyl group having 1 to 20 carbon atoms, an aryl group having 6 to 30 carbon atoms, an arylalkyl group having 7 to 30 carbon atoms, or an anchor group;
$R^{28}$ to $R^{31}$ are each independently a hydrogen atom, a halogen atom, an alkyl group having 1 to 20 carbon atoms, or an aryl group having 6 to 12 carbon atoms, where $R^{28}$ and $R^{30}$ may each be eliminated to form an unsaturated bond, or $R^{29}$ and $R^{31}$ may be linked to form a benzene ring which may have a substituent, a naphthalene ring which may have a substituent, or a phenanthrene ring which may have a substituent;

t is 0 or 1; and
the substituent —$Y^1$—COOH substitutes $S^3$; and

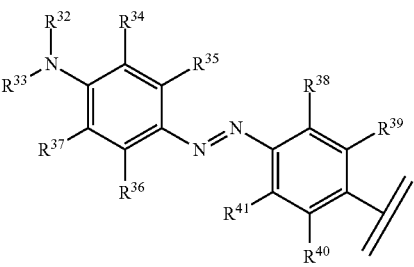

(VII)

wherein:
$R^{32}$ to $R^{33}$ are each independently a hydrogen atom, an alkyl group having 1 to 20 carbon atoms, or an arylalkyl group having 7 to 30 carbon atoms; and
$R^{34}$ to $R^{41}$ are each independently a hydrogen atom, a halogen atom, a hydroxyl group, a cyano group, a nitro group, an alkyl group having 1 to 20 carbon atoms, an aryl group having 6 to 30 carbon atoms, or an arylalkyl group having 7 to 30 carbon atoms;
$Z^1$ is any one divalent linking group selected from —CONR—, —NRCO—, —$SO_2$NR—, and —NR$SO_2$—;
R in $Z^1$ is a hydrogen atom, an alkyl group having 1 to 8 carbon atoms, or an arylalkyl group having 7 to 20 carbon atoms;
$D^1$ is a benzene ring which may have a substituent, a naphthalene ring which may have a substituent, or a phenanthrene ring which may have a substituent;
$R^1$ is a hydrogen atom, an alkyl group having 1 to 20 carbon atoms, an alkenyl group having 2 to 8 carbon atoms, or an alkynyl group having 2 to 8 carbon atoms, each of which may be substituted by a halogen atom, a nitro group, a cyano group, an amino group, a hydroxyl group, an ether group, a carbonyl group, an aromatic ring, a heterocyclic ring, or a metallocenyl group;
$R^{42}$ are each independently a hydrogen atom, an alkyl group having 1 to 8 carbon atoms, an aryl group having 6 to 12 carbon atoms, a halogen atom, or a cyano group;
$X^1$ is an oxygen atom, a sulfur atom, a selenium atom, $CR^3R^4$, or $NR^5$;
$R^3$ to $R^5$ are each independently a hydrogen atom, an alkyl group having 1 to 20 carbon atoms, an alkenyl group having 2 to 8 carbon atoms, or an alkynyl group having 2 to 8 carbon atoms;
$R^3$ to $R^5$ may each be independently substituted by a halogen atom, a nitro group, a cyano group, an amino group, a hydroxyl group, an ether group, a carbonyl group, an aromatic ring, a heterocyclic ring, or a metallocenyl group, and $R^3$ and $R^4$ may be linked to form an alicyclic group having a 3- to 6-membered ring;
$Y^1$ is an alkylene group having 1 to 8 carbon atoms, or a single bond;
m is 0 to 2;
$An^{b-}$ is a b-valent anion;
a is 1 or 2, and is a coefficient for keeping a charge of the entire dye neutral; and
b is 1 or 2.

5. The compound according to claim 4, wherein the dye is a compound of the structure represented by the following formula (X):

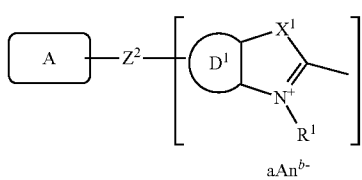

(X)

wherein:
A is selected from the group consisting of the following formulas (IV) to (VII):

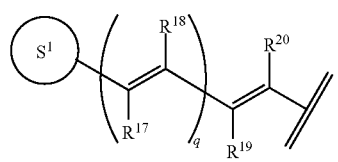

(IV)

wherein:
S$^1$ is an aromatic ring which may have a substituent, or a heterocyclic ring which may have a substituent;
R$^{17}$ to R$^{20}$ are each independently a hydrogen atom, an alkyl group having 1 to 8 carbon atoms, a halogen atom, or a cyano group;
q is 0 or 1, and the substituent —Y$^1$—COOH substitutes S$^1$;

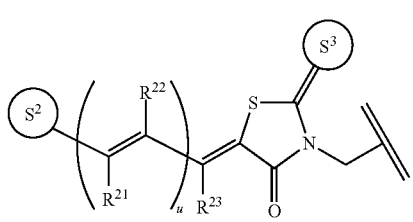

(V)

wherein:
S$^2$ is an aromatic ring which may have a substituent, or a heterocyclic ring which may have a substituent;
S$^3$ is a sulfur atom or a structure represented by the following formula (Va);
R$^{21}$ to R$^{23}$ are each independently a hydrogen atom, an alkyl group having 1 to 8 carbon atoms, a halogen atom, or a cyano group;
R$^{24}$ is a hydrogen atom, an alkyl group having 1 to 20 carbon atoms, an aryl group having 6 to 30 carbon atoms, an arylalkyl group having 7 to 30 carbon atoms, or an anchor group;
u is 0 or 1; and
the substituent —Y$^1$—COOH substitutes S$^2$ and/or S$^3$:

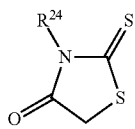

(Va)

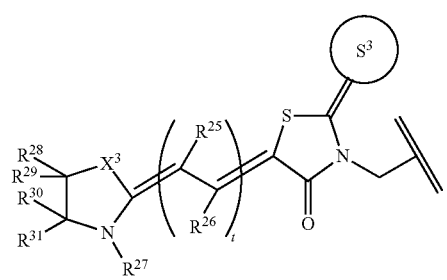

(VI)

wherein:
R$^{25}$ to R$^{26}$ are each independently a hydrogen atom, an alkyl group having 1 to 8 carbon atoms, a halogen atom, or a cyano group;
R$^{27}$ is a hydrogen atom, an alkyl group having 1 to 20 carbon atoms, an aryl group having 6 to 30 carbon atoms, an arylalkyl group having 7 to 30 carbon atoms, or an anchor group;
R$^{28}$ to R$^{31}$ are each independently a hydrogen atom, a halogen atom, an alkyl group having 1 to 20 carbon atoms, or an aryl group having 6 to 12 carbon atoms, where R$^{28}$ and R$^{30}$ may each be eliminated to form an unsaturated bond, or R$^{29}$ and R$^{31}$ may be linked to form a benzene ring which may have a substituent, a naphthalene ring which may have a substituent, or a phenanthrene ring which may have a substituent;
t is 0 or 1; and
the substituent —Y$^1$—COOH substitutes S$^3$; and

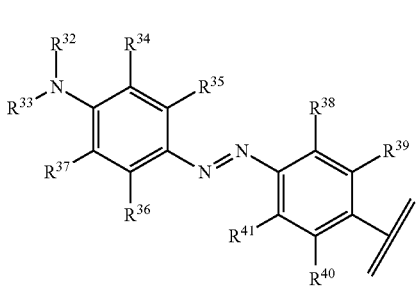

(VII)

wherein:
R$^{32}$ to R$^{33}$ are each independently a hydrogen atom, an alkyl group having 1 to 20 carbon atoms, or an arylalkyl group having 7 to 30 carbon atoms; and
R$^{34}$ to R$^{41}$ are each independently a hydrogen atom, a halogen atom, a hydroxyl group, a cyano group, a nitro group, an alkyl group having 1 to 20 carbon atoms, an aryl group having 6 to 30 carbon atoms, or an arylalkyl group having 7 to 30 carbon atoms;
Z$^2$ is any one divalent linking group selected from —CONR—, —NRCO, —SO$_2$NR—, and —NRSO$_2$—,
R in Z$^2$ is a hydrogen atom, an alkyl group having 1 to 8 carbon atoms, or an arylalkyl group having 7 to 20 carbon atoms;
D$^1$ is a benzene ring which may have a substituent, a naphthalene ring which may have a substituent, or a phenanthrene ring which may have a substituent;
R$^1$ is a hydrogen atom, an alkyl group having 1 to 20 carbon atoms, an alkenyl group having 2 to 8 carbon atoms, or an alkynyl group having 2 to 8 carbon atoms, each of which may be substituted by a halogen atom, a nitro group, a cyano group, an amino group, a hydroxyl group, an ether group, a carbonyl group, an aromatic ring, a heterocyclic ring, or a metallocenyl group, $X^1$ is an oxygen atom, a sulfur atom, a selenium atom, $CR^3R^4$, or $NR^5$;

$R^3$ to $R^5$ are each independently a hydrogen atom, an alkyl group having 1 to 20 carbon atoms, an alkenyl group having 2 to 8 carbon atoms, or an alkynyl group having 2 to 8 carbon atoms, where $R^3$ to $R^5$ may each be independently substituted by a halogen atom, a nitro group, a cyano group, an amino group, a hydroxyl group, an ether group, a carbonyl group, an aromatic ring, a heterocyclic ring, or a metallocenyl group, and $R^3$ and $R^4$ may be linked to form an alicyclic group having a 3- to 6-membered ring;

$An^{b-}$ is a b-valent anion;

a is 1 or 2, and is a coefficient for keeping the charge of the entire dye neutral; and b is 1 or 2.

6. A photoelectric conversion device comprising a working electrode comprising a dye supported on a metal oxide layer, the dye being a compound of the structure represented by the following general formula (I):

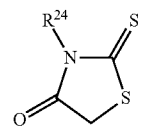
(I)

wherein:

A is selected from the group consisting of the following formulas (IV) to (VII):

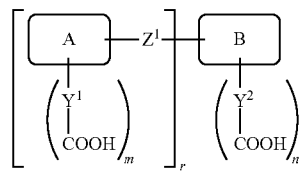
(IV)

wherein:

$S^1$ is an aromatic ring which may have a substituent, or a heterocyclic ring which may have a substituent;

$R^{17}$ to $R^{20}$ are each independently a hydrogen atom, an alkyl group having 1 to 8 carbon atoms, a halogen atom, or a cyano group;

q is 0 or 1, and the substituent —$Y^1$—COOH substitutes $S^1$;

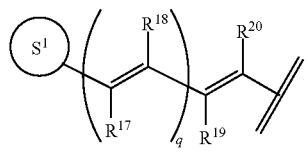
(V)

wherein:

$S^2$ is an aromatic ring which may have a substituent, or a heterocyclic ring which may have a substituent;

$S^3$ is a sulfur atom or a structure represented by the following formula (Va);

$R^{21}$ to $R^{23}$ are each independently a hydrogen atom, an alkyl group having 1 to 8 carbon atoms, a halogen atom, or a cyano group;

$R^{24}$ is a hydrogen atom, an alkyl group having 1 to 20 carbon atoms, an aryl group having 6 to 30 carbon atoms, an arylalkyl group having 7 to 30 carbon atoms, or an anchor group;

u is 0 or 1; and the substituent —$Y^1$—COOH substitutes $S^2$ and/or $S^3$:

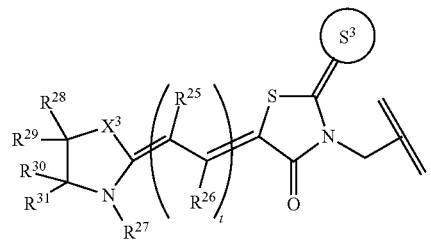
(Va)

(VI)

wherein:

$R^{25}$ to $R^{26}$ are each independently a hydrogen atom, an alkyl group having 1 to 8 carbon atoms, a halogen atom, or a cyano group;

$R^{27}$ is a hydrogen atom, an alkyl group having 1 to 20 carbon atoms, an aryl group having 6 to 30 carbon atoms, an arylalkyl group having 7 to 30 carbon atoms, or an anchor group;

$R^{28}$ to $R^{31}$ are each independently a hydrogen atom, a halogen atom, an alkyl group having 1 to 20 carbon atoms, or an aryl group having 6 to 12 carbon atoms, where $R^{28}$ and $R^{30}$ may each be eliminated to form an unsaturated bond, or $R^{29}$ and $R^{31}$ may be linked to form a benzene ring which may have a substituent, a naphthalene ring which may have a substituent, or a phenanthrene ring which may have a substituent;

t is 0 or 1; and the substituent —$Y^1$—COOH substitutes $S^3$; and

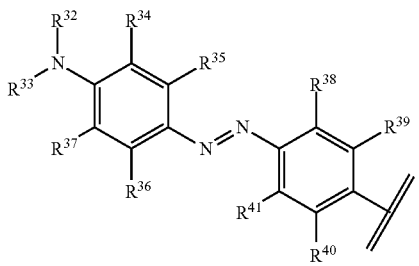
(VII)

wherein:
R$^{32}$ to R$^{33}$ are each independently a hydrogen atom, an alkyl group having 1 to 20 carbon atoms, or an arylalkyl group having 7 to 30 carbon atoms; and
R$^{34}$ to R$^{41}$ are each independently a hydrogen atom, a halogen atom, a hydroxyl group, a cyano group, a nitro group, an alkyl group having 1 to 20 carbon atoms, an aryl group having 6 to 30 carbon atoms, or an arylalkyl group having 7 to 30 carbon atoms;
B comprises a cyanine skeleton having a maximum absorption wavelength λmax of 500 to 700 nm in a methanol solution;
Z$^1$ is a divalent linking group selected from —CONR—, —NRCO—, —SO$_2$NR—, and —NRSO$_2$—;
R in Z$^1$ is a hydrogen atom, an alkyl group having 1 to 8 carbon atoms, or an arylalkyl group having 7 to 20 carbon atoms;
Y$^1$ and Y$^2$ are each independently an alkylene group having 1 to 8 carbon atoms, or a single bond;
r is 1 or 2;
m and n are each independently an integer of 0 to 2; and
(m+n) is 1 or more.

7. The photoelectric conversion device according to claim 6, wherein the dye is a compound of the structure represented by the following general formula (II):

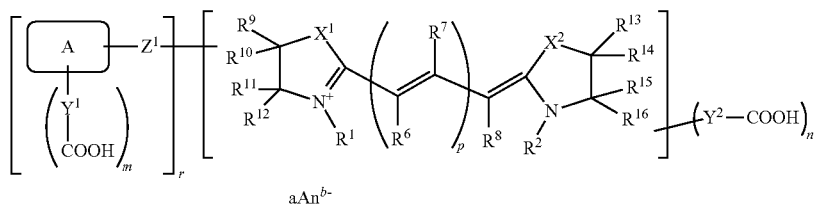

(II)

wherein:
X$^1$ and X$^2$ are each independently an oxygen atom, a sulfur atom, a selenium atom, CR$^3$R$^4$, or NR$^5$;
R$^1$ to R$^5$ are each independently a hydrogen atom, an alkyl group having 1 to 20 carbon atoms, an alkenyl group having 2 to 8 carbon atoms, or an alkynyl group having 2 to 8 carbon atoms, where R$^1$ to R$^5$ may each be independently substituted by a halogen atom, a nitro group, a cyano group, an amino group, a hydroxyl group, an ether group, a carbonyl group, an aromatic ring, a heterocyclic ring, or a metallocenyl group, and R$^3$ and R$^4$ may be linked to form an alicyclic group having a 3- to 6-membered ring;
R$^6$ to R$^8$ are each independently a hydrogen atom, an alkyl group having 1 to 8 carbon atoms, an aryl group having 6 to 12 carbon atoms, a halogen atom, or a cyano group;

R$^9$ to R$^{16}$ are each independently a hydrogen atom, a halogen atom, an alkyl group having 1 to 20 carbon atoms, or an aryl group having 6 to 12 carbon atoms;

in R$^9$ to R$^{16}$, R$^9$ and R$^{11}$ may be eliminated or R$^{13}$ and R$^{15}$ may be eliminated to each form an unsaturated bond, or R$^{10}$ and R$^{12}$ may be linked or R$^{14}$ and R$^{16}$ may be linked to each form a benzene ring which may have a substituent, a naphthalene ring which may have a substituent, or a phenanthrene ring which may have a substituent;

p is 1 or 2;
Z$^1$ in the formula replaces R$^1$ to R$^{16}$ or a hydrogen atom contained in R$^1$ to R$^{16}$;
the substituent —Y$^2$—COOH in the formula replaces R$^1$ to R$^{16}$ or a hydrogen atom contained in R$^1$ to R$^{16}$;
An$^{b-}$ is a b-valent anion;
a is 1 or 2, and is a coefficient for keeping a charge of the entire dye neutral;
b is 1 or 2; and
m, n, r, Z$^1$, A, Y$^1$, and Y$^2$ are the same as described in formula (I).

8. The photoelectric conversion device according to claim 7, wherein the dye is a compound of the structure represented by the following general formula (III):

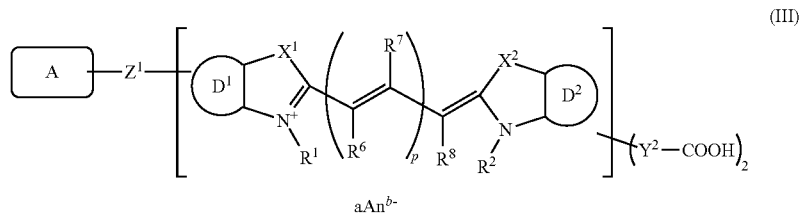

(III)

wherein:
D$^1$ and D$^2$ are each independently a benzene ring which may have a substituent, a naphthalene ring which may have a substituent, or a phenanthrene ring which may have a substituent;
two substituents —Y$^2$—COOH in the formula each replace R$^1$ to R$^8$ or a hydrogen atom contained in R$^1$ to R$^8$, or substitute the benzene ring, the naphthalene ring, or the phenanthrene ring represented by D$^1$ and D$^2$; and
the other variables are the same as described in formula (II).

* * * * *